United States Patent
Knoblauch et al.

(10) Patent No.: US 12,215,160 B2
(45) Date of Patent: Feb. 4, 2025

(54) TREATMENT OF PATIENTS HAVING C-MET EXON 14 SKIPPING MUTATIONS

(71) Applicant: Janssen Biotech, Inc., Horsham, PA (US)

(72) Inventors: Roland Knoblauch, Doylestown, PA (US); Sylvie Laquerre, Chesterbrook, PA (US); Sheri Moores, Wayne, PA (US)

(73) Assignee: Janssen Biotech, Inc., Horsham, PA (US)

( * ) Notice: Subject to any disclaimer, the term of this patent is extended or adjusted under 35 U.S.C. 154(b) by 140 days.

(21) Appl. No.: 17/174,386

(22) Filed: Feb. 12, 2021

(65) Prior Publication Data

US 2021/0253717 A1  Aug. 19, 2021

Related U.S. Application Data

(60) Provisional application No. 62/975,406, filed on Feb. 12, 2020.

(51) Int. Cl.
| | | |
|---|---|---|
| *A61P 35/00* | (2006.01) | |
| *A61K 31/53* | (2006.01) | |
| *A61K 45/06* | (2006.01) | |
| *C07K 16/28* | (2006.01) | |
| *A61K 39/00* | (2006.01) | |

(52) U.S. Cl.
CPC .......... *C07K 16/2863* (2013.01); *A61K 31/53* (2013.01); *A61K 45/06* (2013.01); *A61P 35/00* (2018.01); *A61K 2039/505* (2013.01); *A61K 2039/545* (2013.01); *C07K 2317/31* (2013.01)

(58) Field of Classification Search
CPC .................................................. C07K 16/2863
USPC ...................................................... 424/136.1
See application file for complete search history.

(56) References Cited

U.S. PATENT DOCUMENTS

| | | | |
|---|---|---|---|
| 7,615,529 B2 | 11/2009 | Kong-Beltran et al. | |
| 7,767,792 B2 | 8/2010 | Johns et al. | |
| 7,892,770 B2 | 2/2011 | Cao et al. | |
| 7,981,605 B2 | 7/2011 | Freeman et al. | |
| 8,067,175 B2 | 11/2011 | Varmus et al. | |
| 8,242,247 B2 | 8/2012 | Klein et al. | |
| 8,323,962 B2 | 12/2012 | Dall'Acqua et al. | |
| 8,501,171 B2 | 8/2013 | Bourel et al. | |
| 8,536,118 B2 | 9/2013 | Kong-Beltran et al. | |
| 8,562,985 B2 | 10/2013 | Michaud et al. | |
| 8,652,473 B2 | 2/2014 | Johns et al. | |
| 8,715,665 B2 | 5/2014 | Janne et al. | |
| 8,821,869 B2 | 9/2014 | Michaud et al. | |
| 8,962,808 B2 | 2/2015 | Chan et al. | |
| 9,394,367 B2 | 7/2016 | Cheong et al. | |
| 9,580,508 B2 * | 2/2017 | Chiu | A61K 31/437 |
| 9,593,098 B2 | 3/2017 | Suh et al. | |
| 9,593,164 B2 | 3/2017 | Chiu et al. | |
| 9,683,052 B2 | 6/2017 | Blein et al. | |
| 9,683,053 B2 | 6/2017 | Blein et al. | |
| 10,626,189 B2 | 4/2020 | Giese et al. | |
| 10,813,933 B2 | 10/2020 | Katayama et al. | |
| 11,459,391 B2 | 10/2022 | Moores et al. | |
| 11,850,248 B2 | 12/2023 | Oh et al. | |
| 2003/0194403 A1 | 10/2003 | van de Winkel et al. | |
| 2005/0272083 A1 | 12/2005 | Seshagiri | |
| 2007/0287170 A1 | 12/2007 | Davis et al. | |
| 2009/0182127 A1 | 7/2009 | Kjaergaard et al. | |
| 2010/0015133 A1 | 1/2010 | Igawa et al. | |
| 2011/0123532 A1 | 5/2011 | Gurney et al. | |
| 2012/0149876 A1 | 6/2012 | Von Kreudenstein et al. | |
| 2013/0195849 A1 | 8/2013 | Von Kreudenstein et al. | |
| 2014/0141000 A1 * | 5/2014 | Chiu | A61K 39/3955 435/375 |
| 2017/0073414 A1 | 3/2017 | Weiskopf et al. | |
| 2017/0101475 A1 | 4/2017 | Chiu et al. | |
| 2017/0233497 A1 | 8/2017 | Labrijn et al. | |
| 2017/0275367 A1 | 9/2017 | Chiu et al. | |
| 2018/0057595 A1 * | 3/2018 | Yang | A61K 45/06 |
| 2018/0312604 A1 | 11/2018 | Throsby et al. | |
| 2019/0248907 A1 | 8/2019 | Doerner et al. | |
| 2019/0315873 A1 | 10/2019 | Michieli | |
| 2019/0046641 A1 | 12/2019 | Patel et al. | |
| 2019/0371432 A1 | 12/2019 | Sikora et al. | |
| 2020/0087405 A1 | 3/2020 | Sidhu et al. | |
| 2020/0239595 A1 | 7/2020 | Allison et al. | |
| 2020/0270351 A1 | 8/2020 | Moores et al. | |
| 2020/0316071 A1 | 10/2020 | Robichaux et al. | |
| 2020/0317792 A1 | 10/2020 | Griswold et al. | |
| 2020/0325243 A1 | 10/2020 | Tikhomirov et al. | |
| 2020/0360394 A1 | 11/2020 | Oh et al. | |
| 2021/0017285 A1 | 1/2021 | Laquerre et al. | |
| 2023/0130600 A1 | 4/2023 | Moores et al. | |

FOREIGN PATENT DOCUMENTS

| | | |
|---|---|---|
| EP | 1868648 B1 | 4/2015 |
| EP | 1851339 B1 | 5/2016 |
| EP | 3611273 A1 | 2/2020 |

(Continued)

OTHER PUBLICATIONS

Tong et al (Clin Cancer Res, 2016, 22(12): 3048-3056).*
Wolf et al (Journal of Clinical Oncology, 2019, 37(No. 15 suppl): Abstract 9004).*
Schuler et al (Journal of Clinical Oncology, 2016, 34(No. 15 suppl): Abstract 9067).*
Castoldi et al (Oncogene, 2013, 32: 5593-5601).*
Frampton et al (Cancer Discovery, 2015, 850-859).*
Liu et al (Clinical Cancer Research, 2011, 17(22): 7127-7138).*
Hu et al (Cell, 2018, 175: 1665-1678).*

(Continued)

*Primary Examiner* — Sean E Aeder
(74) *Attorney, Agent, or Firm* — BakerHostetler

(57) ABSTRACT

The present invention relates to treatment of subjects having a cancer that is positive for c-Met exon 14 skipping mutations.

47 Claims, 8 Drawing Sheets

Specification includes a Sequence Listing.

(56) References Cited

FOREIGN PATENT DOCUMENTS

| WO | WO 1988001649 A1 | 3/1988 |
|---|---|---|
| WO | WO 1992001047 A1 | 1/1992 |
| WO | WO 1994013804 A1 | 6/1994 |
| WO | WO 1998044001 A1 | 10/1998 |
| WO | WO 2006028936 A2 | 3/2006 |
| WO | WO 2006028936 A3 | 3/2006 |
| WO | WO 2008077546 A1 | 7/2008 |
| WO | WO 2009018386 A1 | 2/2009 |
| WO | WO 2009080251 A1 | 7/2009 |
| WO | WO 2009080252 A1 | 7/2009 |
| WO | WO 2009080254 A1 | 7/2009 |
| WO | WO 2009085462 A1 | 7/2009 |
| WO | WO 2011131746 A2 | 10/2011 |
| WO | WO 2011131746 A3 | 10/2011 |
| WO | WO 2015043614 A1 | 4/2015 |
| WO | WO 2015188777 A1 | 12/2015 |
| WO | WO 2016060443 A2 | 4/2016 |
| WO | WO 2016060443 A3 | 4/2016 |
| WO | WO 2016081423 A1 | 5/2016 |
| WO | WO 2018094225 A1 | 5/2018 |
| WO | WO 2018194356 A1 | 10/2018 |
| WO | WO 2019022485 A1 | 1/2019 |
| WO | WO 2019022486 A1 | 1/2019 |
| WO | WO 2019022487 A1 | 1/2019 |
| WO | WO 2020055643 A2 | 3/2020 |
| WO | WO 2020055643 A3 | 3/2020 |
| WO | WO 2020079637 A1 | 4/2020 |
| WO | WO 2020174370 A2 | 9/2020 |
| WO | WO 2020174370 A3 | 9/2020 |
| WO | WO 2020205521 A1 | 10/2020 |
| WO | WO 2020214824 A1 | 10/2020 |
| WO | WO 2020214831 A1 | 10/2020 |
| WO | WO 2020230091 A1 | 11/2020 |
| WO | WO 2021161262 A1 | 8/2021 |

OTHER PUBLICATIONS

Almatroodi et al., 2016, "Characterization of M1/M2 Tumour-Associated Macrophages (TAMs) and Th1/Th2 Cytokine Profiles in Patients with NSCLC," Cancer Microenviron, 9(1):1-11 (Epub 2015).

Arenberg et al., 2000, "Macrophage infiltration in human non-small-cell lung cancer: the role of CC chemokines," Cancer Immunol. Immunother., 49(2):63-70.

Arend et al., 2000, "Biological role of interleukin 1 receptor antagonist isoforms," Ann. Rheum. Dis., 59 Suppl 1(Suppl 1):160-64.

Awad et al., 2016, "MET Exon 14 Mutations in Non-Small-Cell Lung Cancer Are Associated With Advanced Age and Stage-Dependent MET Genomic Amplification and c-Met Overexpression," J. Clin. Oncol., 34(7):721-730.

Balkwill, 2004, "Cancer and the chemokine network," Nat. Rev. Cancer, 4(7):540-550.

Bean et al., 2007, "MET amplification occurs with or without T790M mutations in EGFR mutant lung tumors with acquired resistance to gefitinib or erlotinib," Proc. Natl. Acad. Sci. USA, 104(52):20932-20937.

Cappuzzo et al., 2005, "Epidermal growth factor receptor gene and protein and gefitinib sensitivity in non-small-cell lung cancer," J. Natl. Cancer Inst., 97(9):643-655.

Chen et al., 2009, "Clinicopathologic and molecular features of epidermal growth factor receptor T790M mutation and c-MET amplification in tyrosine kinase inhibitor-resistant Chinese non-small cell lung cancer," Pathol. Oncol. Res., 15(4):651-658.

Cho et al., 2018 "Abstract MA26.09: Lazertinib, a 3rd Generation EGFR-TKI, in Patients with EGFR-TKI-Resistant NSCLC: Updated Results of a Phase I/II Study," Journal of Thoracic Oncology, 13(10S):S453.

Cho et al., 2018, "Poster #356: YH25448, a 3rd generation EGFR-TKI, in patients with EGFR-TK1-resistant NSCLC: Phase I/II study results," American Society of Clinical Oncology (ASCO) Annual Meeting, Jun. 1-5, 2018 (5 pages).

Cho et al., 2018, "YH25448, a 3rd generation EGFR-TKI, in patients with EGFR-TK1-resistant NSCLC: Phase I/II study results," American Society of Clinical Oncology (ASCO) Annual Meeting, Jun. 3, 2018, Abstract (2 pages).

Chothia et al., 1987, "Canonical structures for the hypervariable regions of immunoglobulins," J. Mol. Biol., 196(4):901-917.

ClinicalTrials.gov Identifier: NCT02609776 (v49), "Study of JNJ-61186372, a Human Bispecific EGFR and cMet Antibody, in Subjects With Advanced Non-Small Cell Lung Cancer," first posted: Nov. 20, 2015, last update posted: Aug. 14, 2020 (14 pages).

ClinicalTrials.gov Identifier: NCT02609776 (v81), "Study of Amivantamab, a Human Bispecific EGFR and cMet Antibody, in Participants With Advanced Non-Small Cell Lung Cancer (CHRYSA-LIS)," first posted: Nov. 20, 2015, last update posted May 31, 2023 (14 pages).

ClinicalTrials.gov Identifier: NCT03046992 (v1), "A Phase I/II, Open-Label, Multicenter Study to Evaluate the Safety, Tolerability, Pharmacokinetics and Anti-Tumor Activity of YH25448 in Patients With EGFR Mutation Positive Advanced Non-Small Cell Lung Cancer (NSCLC)," submitted on Feb. 7, 2017, first submitted Jan. 26, 2017 (5 pages).

ClinicalTrials.gov Identifier: NCT03046992 (v2), "A Phase I/II, Open-Label, Multicenter Study to Evaluate the Safety, Tolerability, Pharmacokinetics and Anti-Tumor Activity of YH25448 in Patients With EGFR Mutation Positive Advanced Non-Small Cell Lung Cancer (NSCLC)," submitted on Apr. 14, 2017, first submitted Jan. 26, 2017 (5 pages).

ClinicalTrials.gov Identifier: NCT03046992 (v3), "A Phase I/II, Open-Label, Multicenter Study to Evaluate the Safety, Tolerability, Pharmacokinetics and Anti-Tumor Activity of YH25448 in Patients With EGFR Mutation Positive Advanced Non-Small Cell Lung Cancer (NSCLC)," submitted on Jul. 1, 2017, first submitted Jan. 26, 2017 (5 pages).

ClinicalTrials.gov Identifier: NCT03046992 (v4), "A Phase I/II, Open-Label, Multicenter Study to Evaluate the Safety, Tolerability, Pharmacokinetics and Anti-Tumor Activity of YH25448 in Patients With EGFR Mutation Positive Advanced Non-Small Cell Lung Cancer (NSCLC)," submitted on May 29, 2018, first submitted Jan. 26, 2017 (5 pages).

ClinicalTrials.gov Identifier: NCT03046992 (v5), "A Phase I/II, Open-Label, Multicenter Study to Evaluate the Safety, Tolerability, Pharmacokinetics and Anti-Tumor Activity of YH25448 in Patients With EGFR Mutation Positive Advanced Non-Small Cell Lung Cancer (NSCLC)," submitted on Jan. 14, 2019, first submitted Jan. 26, 2017 (5 pages).

Cortot et al., 2017, "Exon 14 Deleted MET Receptor as a New Biomarker and Target in Cancers," J. Natl. Cancer Inst., 109(5). 109(5):djw262 (12 pages).

Descarpentries et al., 2018, "Optimization of Routine Testing for MET Exon 14 Splice Site Mutations in NSCLC Patients," Journal of Thoracic Oncology, 13:1873-1883.

Dhanasekharan et al., 2014, "Transcriptome meta-analysis of lung cancer reveals recurrent aberrations in NRG1 and Hippo pathway genes," Nat. Commun., 5:5893 (12 pages).

Eisenhauer et al., 2009, "New response evaluation criteria in solid tumours: revised RECIST guideline (version 1.1)," Eur. J. Cancer, 45(2):228-247.

Engelman et al., 2007, "MET amplification leads to gefitinib resistance in lung cancer by activating ERBB3 signaling," Science, 316(5827):1039-1043.

Ferrara et al., 2006, "Modulation of therapeutic antibody effector functions by glycosylation engineering: influence of Golgi enzyme localization domain and co-expression of heterologous betal, 4-N-acetylglucosaminyltransferase III and Golgi alpha-mannosidase II," Biotechnol. Bioeng., 93(5):851-861.

Ferrara et al., 2006, "The carbohydrate at FcgammaRIIIa Asn-162. An element required for high affinity binding to non-fucosylated IgG glycoforms" J. Biol. Chem., 281(8):5032-5036 (Epub 2005).

Fujino et al., 2021, "Lung Cancer with MET exon 14 Skipping Mutation: Genetic Feature, Current Treatments, and Future Challenges," Lung Cancer (Auckl), 12:35-50.

(56) References Cited

OTHER PUBLICATIONS

GenBank Accession No. NM_000245.4, "*Homo sapiens* MET proto-oncogene, receptor tyrosine kinase (MET), transcript variant 2, mRNA," Jun. 11, 2023 (7 pages).

GenBank Accession No. NP_000236.2, "hepatocyte growth factor receptor isoform b preproprotein [*Homo sapiens*]," Jun. 11, 2023 (5 pages).

GenBank Accession No. NP_001120972.1, "hepatocyte growth factor receptor isoform a preproprotein [*Homo sapiens*]," Mar. 17, 2022 (4 pages).

GenBank Accession No. NP_005219.2, "epidermal growth factor receptor isoform a precursor [*Homo sapiens*]," Feb. 20, 2022 (7 pages).

Genosco, 2018, "Abstract 9033: Genosco/Yuhan Announce Results from Phase 1/2 Study of Lazertinib (YH25448, GNS-1480), a 3rd-Generation EGFR-TKI, in Advanced NSCLC," American Society of Clinical Oncology (ASCO) Annual Meeting, Jun. 3, 2018 (5 pages).

Graves et al., 1995, "Chemokines, a family of chemotactic cytokines," Crit. Rev. Oral Biol. Med., 6(2):109-118.

Grugan et al., 2017, "Fc-mediated activity of EGFR x c-Met bispecific antibody JNJ-61186372 enhanced killing of lung cancer cells," MAbs, 9(1):114-126 (Epub 2016).

Guo et al., 2021, "MET Exon 14-altered Lung Cancers and MET Inhibitor Resistance," Clin. Cancer Res., 27(3):799-806.

Hardbower et al., 2017, "EGFR-mediated macrophage activation promotes colitis-associated tumorigenesis," Oncogene., 36(27):3807-3819.

Honegger et al., 2001, "Yet another numbering scheme for immunoglobulin variable domains: an automatic modeling and analysis tool," J. Mol. Biol., 309(3):657-670.

Hong et al., 2017, "P3.02b-119: YH25448, a Highly Selective 3rd Generation EGFR TKI, Exhibits Superior Survival over Osimertinib in Animal Model with Brain Metastases from NSCLC," Journal of Thoracic Oncology, 12(1S):S1265-S1266.

Hynes et al., 2005, "ERBB receptors and cancer: the complexity of targeted inhibitors," Nat. Rev. Cancer, 5(5):341-354.

International Search Report and Written Opinion for International Patent Application No. PCT/IB2020/051559 (Pub No. WO 2020174370) mailed Oct. 6, 2020 (16 pages).

International Search Report and Written Opinion for International Patent Application No. PCT/IB2020/054594 (Pub No. WO 2020230091) mailed Sep. 4, 2020 (11 pages).

International Search Report and Written Opinion for International Patent Application No. PCT/IB2021/051203 (Pub No. WO 2021161262) mailed Sep. 4, 2020 (10 pages).

Janne et al., 2006, "Effect of epidermal growth factor receptor tyrosine kinase domain mutations on the outcome of patients with non-small cell lung cancer treated with epidermal growth factor receptor tyrosine kinase inhibitors," Clin. Cancer Res., 12(14 Pt 2):4416s-4420s.

Janson et al., 1991, "Production of IL-1 receptor antagonist by human in vitro-derived macrophages. Effects of lipopolysaccharide and granulocyte-macrophage colony-stimulating factor," J. Immunol., 147(12):4218-4223.

Jeffers et al., 1996, "Hepatocyte growth factor/scatter factor-Met signaling in tumorigenicity and invasion/metastasis," J. Mol. Med. (Berl), 74(9):505-513.

Jia et al., 2008, "Additive roles for MCP-1 and MCP-3 in CCR2-mediated recruitment of inflammatory monocytes during Listeria monocytogenes infection," J. Immunol., 180(10):6846-6853.

Kinder et al., 2015, "An Fc engineering approach that modulates antibody-dependent cytokine release without altering cell-killing functions," MAbs, 7(3):494-504.

Knappik et al., 2000, "Fully synthetic human combinatorial antibody libraries (HuCAL) based on modular consensus frameworks and CDRs randomized with trinucleotides," J. Mol. Biol., 296(1):57-86.

Kobayashi et al., 2005, "EGFR mutation and resistance of non-small-cell lung cancer to gefitinib," N. Engl. J. Med., 352(8):786-792.

Kong-Beltran et al. 2006, "Somatic mutations lead to an oncogenic deletion of met in lung cancer," Cancer Res., 66(1):283-289.

Konno et al., 2012, "Fucose content of monoclonal antibodies can be controlled by culture medium osmolality for high antibody-dependent cellular cytotoxicity," Cytotechnology, 64(3):249-265 (Epub 2011).

Lefranc et al., 2003, "IMGT unique numbering for immunoglobulin and T cell receptor variable domains and Ig superfamily V-like domains," Dev. Comp. Immunol., 27(1):55-77.

Loetscher et al., 1994, "Monocyte chemotactic proteins MCP-1, MCP-2, and MCP-3 are major attractants for human CD4+ and CD8+ T lymphocytes," FASEB J., 8(13):1055-1060.

Martin et al., 1996, "Structural families in loops of homologous proteins: automatic classification, modelling and application to antibodies," J. Mol. Biol., 263(5):800-815.

Martinelli et al., 2009, "Anti-epidermal growth factor receptor monoclonal antibodies in cancer therapy," Clin. Exp. Immunol., 158(1):1-9.

Metlung et al., 2018, "Neutrophils Kill Antibody-Opsonized Cancer Cells by Trogoptosis," Cell Rep., 23(13):3946-3959.e1-e6.

Moores et al., 2016, "A Novel Bispecific Antibody Targeting EGFR and cMet Is Effective against EGFR Inhibitor-Resistant Lung Tumors," Cancer Res., 76(13):3942-3953.

Mori et al., 2004, "Engineering Chinese hamster ovary cells to maximize effector function of produced antibodies using FUT8 siRNA," Biotechnol. Bioeng., 88(7):901-908.

Nakata et al., 2012, "Recent understanding of the molecular mechanisms for the efficacy and resistance of EGF receptor-specific tyrosine kinase inhibitors in non-small cell lung cancer," Expert Opin. Ther. Targets, 16(8):771-781.

Olivier et al., 2010, "EB66 cell line, a duck embryonic stem cell-derived substrate for the industrial production of therapeutic monoclonal antibodies with enhanced ADCC activity, " MAbs, 2(4):405-415.

Pao et al., 2005, "Acquired resistance of lung adenocarcinomas to gefitinib or erlotinib is associated with a second mutation in the EGFR kinase domain," PLoS Med., 2(3):e73 (11 pages).

Perez-Soler et al., 2004, "Determinants of tumor response and survival with erlotinib in patients with non—small-cell lung cancer," J. Clin. Oncol., 22(16):3238-3247.

Pham et al., 2011, "Dynamics of macrophage trogocytosis of rituximab-coated B cells," PLoS One, 6(1):e14498 (11 pages).

PubChem. CID 121269225, Aug. 6, 2016, pp. 1-19; retreived from the internet <URL:https://pubchem.ncbi.nim.nih.gov/compound/121269225>; p. 2, formula (19 pages).

Recondo et al., 2020, "Molecular Mechanisms of Acquired Resistance to MET Tyrosine Kinase Inhibitors in Patients with MET Exon 14-Mutant NSCLC," Clin. Cancer Res., 26(11):2615-2625.

Sequist et al., 2011, "Genotypic and histological evolution of lung cancers acquiring resistance to EGFR inhibitors," Sci. Transl. Med., 3(75):75ra26 (13 pages).

Shi et al., 2010, "De novo selection of high-affinity antibodies from synthetic fab libraries displayed on phage as pIX fusion proteins," J. Mol. Biol., 397(2):385-396.

Shields et al., 2001, "High resolution mapping of the binding site on human IgGl for Fc gamma RI, Fc gamma RII, Fc gamma RIII, and FcRn and design of IgG1 variants with improved binding to the Fc gamma R," J. Biol. Chem., 276(9):6591-6604 (Epub 2000).

Shields et al., 2002, "Lack of fucose on human IgG1 N-linked oligosaccharide improves binding to human Fcgamma RIII and antibody-dependent cellular toxicity," J. Biol. Chem., 277(30):26733-26740.

Shinkawa et al., 2003, "The absence of fucose but not the presence of galactose or bisecting N-acetylglucosamine of human IgG1 complex-type oligosaccharides shows the critical role of enhancing antibody-dependent cellular cytotoxicity," J. Biol. Chem., 278(5):3466-3473 (Epub 2002).

Taylor et al., 2015, "Fcγ-receptor-mediated trogocytosis impacts mAb-based therapies: historical precedence and recent developments," Blood, 125(5):762-766 (Epub 2014).

(56) References Cited

OTHER PUBLICATIONS

Turke et al., 2010, "Preexistence and clonal selection of MET amplification in EGFR mutant NSCLC," Cancer Cell, 17(1):77-88.
Uguccioni et al., 1995, "Actions of the chemotactic cytokines MCP-1, MCP-2, MCP-3, RANTES, MIP-1 alpha and MIP-1 beta on human monocytes," Eur. J. Immunol., 25(1):64-68.
Ullrich et al., 1984, "Human epidermal growth factor receptor cDNA sequence and aberrant expression of the amplified gene in A431 epidermoid carcinoma cells," Nature, 309(5967):418-425.
Velmurugan et al., 2016, "Macrophage-Mediated Trogocytosis Leads to Death of Antibody-Opsonized Tumor Cells," Mol. Cancer Ther., 15(8):1879-1889.
Vijayaraghavan et al., 2020, "Amivantamab (JNJ-61186372), an Fc Enhanced EGFR/cMet Bispecific Antibody, Induces Receptor Downmodulation and Antitumor Activity by Monocyte/Macrophage Trogocytosis," Mol. Cancer Ther., 19(10):2044-2056.
Weiskopf et al., 2015, "Macrophages are critical effectors of antibody therapies for cancer," MAbs, 7(2):303-310.
Wu et al., 1970, "An analysis of the sequences of the variable regions of Bence Jones proteins and myeloma light chains and their implications for antibody complementarity," J. Exp. Med., 132(2):211-250.
Yano et al., 2008, "Hepatocyte growth factor induces gefitinib resistance of lung adenocarcinoma with epidermal growth factor receptor-activating mutations," Cancer Res., 68(22):9479-9487.
Yun et al., 2008, "The T790M mutation in EGFR kinase causes drug resistance by increasing the affinity for ATP," Proc. Natl. Acad. Sci. USA, 105(6):2070-2075.
Yun et al., 2019, "YH25448, an Irreversible EGFR-TKI with Potent Intracranial Activity in EGFR Mutant Non-Small Cell Lung Cancer," Clin. Cancer Res., 25(8):2575-2587.
Zhou et al., 2008, "Development of a simple and rapid method for producing non-fucosylated oligomannose containing antibodies with increased effector function," Biotechnol. Bioeng., 99(3):652-665.
ClinicalTrials.gov Identifier: NCT02609776 (v12), "A Phase 1, First-in-Human, Open-Label, Dose Escalation Study of JNJ-61186372, a Human Bispecific EGFR and cMet Antibody, in Subjects With Advanced Non-Small Cell Lung Cancer," first posted: Nov. 20, 2015, last update posted: Mar. 31, 2017 (7 pages).
Emdal et al., 2017, "Characterization of In Vivo Resistance to Osimertinib and JNJ-61186372, an EGFR/Met Bispecific Antibody, Reveals Unique and Consensus Mechanisms of Resistance," Mol. Cancer Ther., 16(11):2572-2585.
U.S. Appl. No. 16/798,662, filed Feb. 24, 2020, 20200270351 (Aug. 27, 2020), Combination Therapies and Patient Stratification with Bispecific Anti-EGFR/c-Met Antibodies, now U.S. Pat. No. 11,459,391 (Oct. 4, 2022), Ruixiang Li.
U.S. Appl. No. 17/817,295, filed Aug. 3, 2022, 20230130600 (Apr. 27, 2023), Combination Therapies and Patient Stratification with Bispecific Anti-EGFR/c-Met Antibodies.
U.S. Appl. No. 15/931,726, filed May 14, 2020, 20210017285 (Jan. 21, 2021), Combination Therapies with Bispecific Anti-EGFR/c-Met Antibodies and Third Generation EGFR Tyrosine Kinase Inhibitors, Sarah Abdoalatif Alsomairy.
U.S. Appl. No. 18/510,412, filed Nov. 15, 2023, Combination Therapies with Bispecific Anti-EGFR/c-Met Antibodies and Third Generation EGFR Tyrosine Kinase Inhibitors.
Baltschukat S., et al., "Capmatinib (INC280) Is Active Against Models of Non-Small Cell Lung Cancer and Other Cancer Types with Defined Mechanisms of MET Activation", Clin Cancer Res., May 15, 2019, vol. 25. No. 10, pp. 3164-3175.
Highlights of Prescribing Information for TABRECTA. TABRECTA™ (capmatinib) tablets, for oral use, May 2020, 14 pages.
Kabat et al., Sequences of proteins of immunological interest, 5th Ed., Public Health Service, National Institutes of Health, Bethesda MD, 1991.
Yang et al., "Overcoming erlotinib resistance with tailored treatment regimen in patient-derived xenografts from naïve Asian NSCLC patients", International Journal of Cancer, 2013, 132, E74-E84.
Anonymous: "Study of JNJ-61186372, a Human Bispecific EGFR and cMet Antibody, in Participants With Advanced Non-Small Cell Lung Cancer", NCT02609776 , V43, Jan. 20, 2020, pp. 24.
Dhillon S., "Capmatinib: First Approval", Biosis, Jul. 2020, vol. 80, No. 11, pp. 2.
Rotow et al., "Co-occurring Alterations 4, 12 in the RAS-MAPK Pathway Limit Response to MET Inhibitor Treatment in MET Exon 14 Skipping Mutation-Positive Lung Cancer", Clin Cancer Res., 2020, vol. 26, No. 2, pp. 439-449.

\* cited by examiner

SEQUENCE LISTING

<160> NUMBER OF SEQ ID NOS: 21

<210> SEQ ID NO 1
<211> LENGTH: 5
<212> TYPE: PRT
<213> ORGANISM: Artificial Sequence
<220> FEATURE:
<223> OTHER INFORMATION: HCDR1, EGFR binding arm

<400> SEQUENCE: 1

Thr Tyr Gly Met His
1               5

<210> SEQ ID NO 2
<211> LENGTH: 17
<212> TYPE: PRT
<213> ORGANISM: Artificial Sequence
<220> FEATURE:
<223> OTHER INFORMATION: HCDR2, EGFR binding arm

<400> SEQUENCE: 2

Val Ile Trp Asp Asp Gly Ser Tyr Lys Tyr Tyr Gly Asp Ser Val Lys
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: HCDR3, EGFR binding arm

<400> SEQUENCE: 3

Asp Gly Ile Thr Met Val Arg Gly Val Met Lys Asp Tyr Phe Asp Tyr
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: LCDR1, EGFR binding arm

<400> SEQUENCE: 4

Arg Ala Ser Gln Asp Ile Ser Ser Ala Leu Val
1               5                   10

<210> SEQ ID NO 5
<211> LENGTH: 7
<212> TYPE: PRT
<213> ORGANISM: Artificial Sequence
<220> FEATURE:
<223> OTHER INFORMATION: LCDR2, EGFR binding arm

<400> SEQUENCE: 5

Asp Ala Ser Ser Leu Glu Ser

```
1               5
```

```
<210> SEQ ID NO 6
<211> LENGTH: 9
<212> TYPE: PRT
<213> ORGANISM: Artificial Sequence
<220> FEATURE:
<223> OTHER INFORMATION: LCDR3, EGFR binding arm

<400> SEQUENCE: 6

Gln Gln Phe Asn Ser Tyr Pro Leu Thr
1               5

<210> SEQ ID NO 7
<211> LENGTH: 5
<212> TYPE: PRT
<213> ORGANISM: Artificial Sequence
<220> FEATURE:
<223> OTHER INFORMATION: HCDR1, c-Met binding arm

<400> SEQUENCE: 7

Ser Tyr Gly Ile Ser
1               5

<210> SEQ ID NO 8
<211> LENGTH: 17
<212> TYPE: PRT
<213> ORGANISM: Artificial Sequence
<220> FEATURE:
<223> OTHER INFORMATION: HCDR2, c-Met binding arm

<400> SEQUENCE: 8

Trp Ile Ser Ala Tyr Asn Gly Tyr Thr Asn Tyr Ala Gln Lys Leu Gln
1               5                   10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: HCDR3, c-Met binding arm

<400> SEQUENCE: 9

Asp Leu Arg Gly Thr Asn Tyr Phe Asp Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: LCDR1, c-Met binding arm

<400> SEQUENCE: 10

Arg Ala Ser Gln Gly Ile Ser Asn Trp Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: LCDR2, c-Met binding arm

<400> SEQUENCE: 11
```

Ala Ala Ser Ser Leu Leu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: LCDR3, c-Met binding arm

<400> SEQUENCE: 12

Gln Gln Ala Asn Ser Phe Pro Ile Thr
1               5

<210> SEQ ID NO 13
<211> LENGTH: 125
<212> TYPE: PRT
<213> ORGANISM: Artificial Sequence
<220> FEATURE:
<223> OTHER INFORMATION: VH, EGFR binding arm

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
        115                 120                 125

<210> SEQ ID NO 14
<211> LENGTH: 107
<212> TYPE: PRT
<213> ORGANISM: Artificial Sequence
<220> FEATURE:
<223> OTHER INFORMATION: VL, EGFR binding arm

<400> SEQUENCE: 14

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys

<210> SEQ ID NO 15
<211> LENGTH: 119
<212> TYPE: PRT
<213> ORGANISM: Artificial Sequence
<220> FEATURE:
<223> OTHER INFORMATION: VH, c-Met binding arm

<400> SEQUENCE: 15

```
Gln Val Gln Leu Val Gln Ser Gly Ala Glu Val Lys Lys Pro Gly Ala
1               5                   10                  15
Ser Val Lys Val Ser Cys Glu Thr Ser Gly Tyr Thr Phe Thr Ser Tyr
            20                  25                  30
Gly Ile Ser Trp Val Arg Gln Ala Pro Gly His Gly Leu Glu Trp Met
        35                  40                  45
Gly Trp Ile Ser Ala Tyr Asn Gly Tyr Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Leu Arg Gly Thr Asn Tyr Phe Asp Tyr Trp Gly Gln Gly
            100                 105                 110
Thr Leu Val Thr Val Ser Ser
        115
```

<210> SEQ ID NO 16
<211> LENGTH: 107
<212> TYPE: PRT
<213> ORGANISM: Artificial Sequence
<220> FEATURE:
<223> OTHER INFORMATION: VL, c-Met binding arm

<400> SEQUENCE: 16

```
Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Asn Trp
            20                  25                  30
Leu Ala Trp Phe Gln His Lys Pro Gly Lys Ala Pro Lys Leu Leu Ile
        35                  40                  45
Tyr Ala Ala Ser Ser Leu Leu Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Phe Pro Ile
                85                  90                  95
Thr Phe Gly Gln Gly Thr Arg Leu Glu Ile Lys
            100                 105
```

<210> SEQ ID NO 17
<211> LENGTH: 455
<212> TYPE: PRT
<213> ORGANISM: Artificial Sequence
<220> FEATURE:
<223> OTHER INFORMATION: Heavy chain 1

<400> SEQUENCE: 17

```
Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
            35                  40                  45

Ala Val Ile Trp Asp Asp Gly Ser Tyr Lys Tyr Tyr Gly Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Arg Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
            405                 410                 415

Lys Leu Thr Val Asp Lys Ser Arg Trp Gln Gln Gly Asn Val Phe Ser
            420                 425                 430
```

-continued

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 18
<211> LENGTH: 214
<212> TYPE: PRT
<213> ORGANISM: Artificial Sequence
<220> FEATURE:
<223> OTHER INFORMATION: Light chain 1

<400> SEQUENCE: 18

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 449
<212> TYPE: PRT
<213> ORGANISM: Artificial Sequence
<220> FEATURE:
<223> OTHER INFORMATION: Heavy chain 2

<400> SEQUENCE: 19

Gln Val Gln Leu Val Gln Ser Gly Ala Glu Val Lys Lys Pro Gly Ala
1               5                   10                  15

Ser Val Lys Val Ser Cys Glu Thr Ser Gly Tyr Thr Phe Thr Ser Tyr
            20                  25                  30

Gly Ile Ser Trp Val Arg Gln Ala Pro Gly His Gly Leu Glu Trp Met
        35                  40                  45

Gly Trp Ile Ser Ala Tyr Asn Gly Tyr Thr Asn Tyr Ala Gln Lys Leu
    50                  55                  60

```
Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Leu Arg Gly Thr Asn Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 20
<211> LENGTH: 214
<212> TYPE: PRT
```

<213> ORGANISM: Artificial Sequence
<220> FEATURE:
<223> OTHER INFORMATION: Light chain 2

<400> SEQUENCE: 20

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Phe Gln His Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 21
<211> LENGTH: 47
<212> TYPE: PRT
<213> ORGANISM: Homo sapiens

<400> SEQUENCE: 21

Asp Leu Gly Ser Glu Leu Val Arg Tyr Asp Ala Arg Val His Thr Pro
1               5                   10                  15

His Leu Asp Arg Leu Val Ser Ala Arg Ser Val Ser Pro Thr Thr Glu
            20                  25                  30

Met Val Ser Asn Glu Ser Val Asp Tyr Arg Ala Thr Phe Pro Glu
        35                  40                  45

TREATMENT OF PATIENTS HAVING C-MET EXON 14 SKIPPING MUTATIONS

CROSS REFERENCE TO RELATED APPLICATIONS

This application claims priority to U.S. Provisional Application Ser. No. 62/975,406, filed Feb. 12, 2020. The disclosure of the aforementioned application is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "JBI6242USNP1SEQLIST.TXT" and a creation date of Jan. 19, 2021 and having a size of 19 kb. The sequence listing submitted via EFS-Web is part of the specification and is herein incorporated by reference in its entirety.

FIELD

The present invention relates to treatment of subjects having c-Met exon 14 skipping mutations.

BACKGROUND

The individual roles of both EGFR and c-Met in cancer is well established, making these targets attractive for combination therapy. Both receptors signal through the same survival and anti-apoptotic pathways (ERK and AKT); thus, inhibiting the pair in combination may limit the potential for compensatory pathway activation thereby improving overall efficacy.

Mutations in c-Met are associated with a number of cancers, including renal, gastric, nervous system, sarcomas, and lung cancer. Mutations that result in higher activity or expression, or deletion of negative regulation sites are often implicated in these cancers. For example, deletion of exon 14 and the negative regulation site at Tyr 1003 is associated with a significant percentage of non-small cell lung cancers (NSCLC) and adenocarcinomas.

Relapse or resistance to existing therapeutics is common Hence, there is a need for improved therapeutics or combination of therapeutics and patient stratification biomarkers to develop more effective treatment of a disease, such as EGFR or c-Met positive cancer

SUMMARY

The disclosure provides a method of treating a subject having cancer that is positive for a c-Met exon 14 skipping mutation, comprising administering a therapeutically effective amount of an isolated bispecific anti-epidermal growth factor receptor (EGFR)/hepatocyte growth factor receptor (c-Met) antibody to the subject having cancer that is positive for c-Met exon 14 skipping mutation.

The disclosure also provides a method treating a subject having cancer with a bispecific anti-EGFR/c-Met antibody, comprising:
providing a biological sample from the subject;
determining presence or absence of a c-Met exon 14 skipping mutation in the sample;
administering or providing for administration the bispecific anti-EGFR/c-Met antibody to the subject determined to have c-Met exon 14 skipping mutation.

The disclosure also provides a method of treating a subject having cancer that is positive for a c-Met exon 14 skipping mutation, comprising administering a therapeutically effective amount of an isolated bispecific anti-epidermal growth factor receptor (EGFR)/hepatocyte growth factor receptor (c-Met) antibody to the subject having cancer that is positive for c-Met exon 14 skipping mutation.

In one embodiment the disclosure provides a method for treating a subject having cancer with a bispecific anti-EGFR/c-Met antibody, comprising:
a) providing a biological sample from the subject;
b) determining presence or absence of a c-Met exon 14 skipping mutation in the sample;
c) administering or providing for administration the bispecific anti-EGFR/c-Met antibody to the subject determined to have c-Met exon 14 skipping mutation.

In one embodiment the bispecific anti-EGFR/c-Met antibody comprises a first domain that specifically binds EGFR and a second domain that specifically binds c-Met, wherein the first domain comprises a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 a second domain that binds c-Met, wherein the second domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

In one embodiment the first domain that specifically binds EGFR comprises a heavy chain variable region (VH) of SEQ ID NO: 13 and a light chain variable region (VL) of SEQ ID NO: 14, and the second domain that specifically binds c-Met comprises the VH of SEQ ID NO: 15 and the VL of SEQ ID NO: 16.

In one embodiment the bispecific anti-EGFR/c-Met antibody is an IgG1 isotype.

In one embodiment the bispecific anti-EGFR/c-Met antibody comprises a first heavy chain (HC1) of SEQ ID NO: 17, a first light chain (LC1) of SEQ ID NO: 18, a second heavy chain (HC2) of SEQ ID NO: 19 and a second light chain (LC2) of SEQ ID NO: 20.

In one embodiment the bispecific anti-EGFR/c-Met antibody comprises a biantennary glycan structure with a fucose content of about between 1% to about 15%.

In one embodiment the subject is relapsed or resistant to treatment with one or more prior anti-cancer therapies.

In one embodiment the one or more prior anti-cancer therapies comprises one or more chemotherapeutic agents, checkpoint inhibitors, targeted anti-cancer therapies or kinase inhibitors, or any combination thereof.

In one embodiment the one or more prior anti-cancer thearpies comprises carboplatin, paclitaxel, gemcitabine, cisplatin, vinorelbine, docetaxel, palbociclib, crizotinib, PD-(L)1 axis inhibitor, an inhibitor of EGFR, an inhibitor of c-Met, an inhibitor of HER2, an inhibitor of HER3, an inhibitor of HER4, an inhibitor of VEGFR, an inhibitor of AXL, erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib, or any combination thereof.

In one embodiment the subject is treatment naïve.

In one embodiment cancer that is positive for c-Met exon 14 skipping mutation is positive for CDK4 amplification, EGFR amplification, KRAS amplification, MDM2 amplification, TERT amplification, NF1 R2450*; RAD50 L597Vfs*5, MET c.3082+3A>G, EGFR, wild-type EGFR, an EGFR activating mutation, increased levels of circulating HGF, c-MET amplification or a mutant KRAS, or any combination thereof.

In one embodiment the EGFR activating mutation comprises L718Q, G719A, G719X (X being any amino acid), L861X (X being any amino acid), L858R, E746K, L747S, E749Q, A750P, A755V, V765M, C797S, L858P or T790M substitution, deletion of E746-A750, deletion of R748-P753, insertion of Ala (A) between M766 and A767, insertion of Ser, Val and Ala (SVA) between S768 and V769, insertion of Asn and Ser (NS) between P772 and H773, insertion of one or more amino acids between D761 and E762, A763 and Y764, Y764 and Y765, M766 and A767, A767 and V768, S768 and V769, V769 and D770, D770 and N771, N771 and P772, P772 and H773, H773 and V774, V774 and C775, one or more deletions in EGFR exon 20, or one or more insertions in EGFR exon 20, or any combination thereof.

In one embodiment the mutant KRAS comprises a G12V, G12C, G12A or G12D substitution, or any combination thereof.

In one embodiment the cancer is lung cancer, gastric cancer, colorectal cancer, brain cancer, cancer derived from epithelial cells, breast cancer, ovarian cancer, colorectal cancer, anal cancer, prostate cancer, kidney cancer, bladder cancer, head and neck cancer, pharynx cancer, cancer of the nose, pancreatic cancer, skin cancer, oral cancer, cancer of the tongue, esophageal cancer, vaginal cancer, cervical cancer, cancer of the spleen, testicular cancer, gastric cancer, cancer of the thymus, colon cancer, thyroid cancer, liver cancer, hepatocellular carcinoma (HCC) or sporadic or hereditary papillary renal cell carcinoma (PRCC), or any combination thereof.

In one embodiment the lung cancer is non-small cell lung cancer (NSCLC), small cell lung cancer (SCLC) or lung adenocarcinoma, pulmonary sarcomatoid carcinoma or any combination thereof.

In one embodiment the method comprises further administering one or more anti-cancer therapies to the subject.

In one embodiment the one or more anti-cancer therapies comprise chemotherapy, radiation therapy, surgery, a targeted anti-cancer therapy or a kinase inhibitor, or any combination thereof.

In one embodiment the kinase inhibitor is an inhibitor of EGFR, an inhibitor of c-Met, an inhibitor of HER2, an inhibitor of HER3, an inhibitor of HER4, an inhibitor of VEGFR or an inhibitor of AXL.

In one embodiment the kinase inhibitor is erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib.

In one embodiment the c-Met exon 14 skipping mutation is a de novo mutation.

In one embodiment the c-Met exon 14 skipping mutation is an acquired mutation.

In one embodiment the bispecific anti-EGFR/c-Met antibody is administered at a dose of between about 140 mg to about 1750 mg.

In one embodiment the bispecific anti-EGFR/c-Met antibody is administered at a dose of about 700 mg, about 750 mg, about 800 mg, about 850 mg, 900 mg, 950 mg, 1000 mg, 1050 mg, 1100 mg, 1150 mg, 1200 mg, 1250 mg, 1300 mg, 1350 mg or 1400 mg.

In one embodiment the bispecific anti-EGFR/c-Met antibody is administered twice a week, once a week, once in two weeks, once in three weeks or once in four weeks.

An embodiment of the disclosure provides a method of treating a subject having cancer that is positive for a c-Met exon 14 skipping mutation, comprising administering to the subject a combination therapy, wherein the combination therapy comprises a therapeutically effective amount of an isolated bispecific anti-epidermal growth factor receptor (EGFR)/hepatocyte growth factor receptor (c-Met) antibody and a therapeutically effective amount of a compound of formula (II)

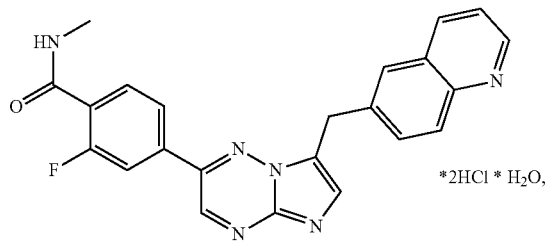

or solvate, hydrate, tautomer, or a pharmaceutically acceptable salt thereof.

In one embodiment the bispecific anti-EGFR/c-Met antibody comprises a first domain that binds EGFR comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 and a second domain that binds c-Met comprising the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

In one embodiment the first domain that binds EGFR comprises a heavy chain variable region (VH) of SEQ ID NO: 13 and a light chain variable region (VL) of SEQ ID NO: 14 and the second domain that binds c-Met comprises the VH of SEQ ID NO: 15 and the VL of SEQ ID NO: 16.

In one embodiment the bispecific anti-EGFR/c-Met antibody is an IgG1 isotype.

In one embodiment the bispecific anti-EGFR/c-Met antibody comprises a first heavy chain (HC1) of SEQ ID NO: 17, a first light chain (LC1) of SEQ ID NO: 18, a second heavy chain (HC2) of SEQ ID NO: 19 and a second light chain (LC2) of SEQ ID NO: 20.

In one embodiment the bispecific anti-EGFR/c-Met antibody has a biantennary glycan structure with a fucose content of between about 1% to about 15%.

In one embodiment the compound of formula (II) or solvate, hydrate, tautomer, or a pharmaceutically acceptable salt thereof is 2-Fluoro-N-methyl-4-[7-(quinolin-6-ylmethyl)imidazo[1,2-b][1,2,4]triazin-2-yl]benzamide-hydrogen chloride-water (1/2/1).

In one embodiment the subject is relapsed or resistant to treatment with one or more prior anti-cancer therapies.

In one embodiment the one or more prior anti-cancer therapies comprises one or more chemotherapeutic agents, checkpoint inhibitors, targeted anti-cancer therapies or kinase inhibitors, or any combination thereof.

In one embodiment the one or more prior anti-cancer thearpies comprises carboplatin, paclitaxel, gemcitabine, cisplatin, vinorelbine, docetaxel, palbociclib, crizotinib, PD-(L)1 axis inhibitor, an inhibitor of EGFR, an inhibitor of c-Met, an inhibitor of HER2, an inhibitor of HER3, an inhibitor of HER4, an inhibitor of VEGFR, an inhibitor of AXL, erlotinib, gefitinib, lapatinib, vandetanib, afatinib, osimertinib, lazertinib, poziotinib, criotinib, cabozantinib, axitinib, lenvatinib, nintedanib, regorafenib, pazopanib, sorafenib or sunitinib, or any combination thereof.

In one embodiment the subject is treatment naïve.

In one embodiment cancer that is positive for c-Met exon 14 skipping mutation is positive for CDK4 amplification, EGFR amplification, KRAS amplification, MDM2 amplification, TERT amplification, NF1 R2450*; RAD50 L597Vfs*5, MET c.3082+3A>G, EGFR, wild-type EGFR, an EGFR activating mutation, increased levels of circulating HGF, c-MET amplification or a mutant KRAS, or any combination thereof.

In one embodiment the EGFR activating mutation comprises L718Q, G719A, G719X (X being any amino acid), L861X (X being any amino acid), L858R, E746K, L747S, E749Q, A750P, A755V, V765M, C797S, L858P or T790M substitution, deletion of E746-A750, deletion of R748-P753, insertion of Ala (A) between M766 and A767, insertion of Ser, Val and Ala (SVA) between 5768 and V769, insertion of Asn and Ser (NS) between P772 and H773, insertion of one or more amino acids between D761 and E762, A763 and Y764, Y764 and Y765, M766 and A767, A767 and V768, S768 and V769, V769 and D770, D770 and N771, N771 and P772, P772 and H773, H773 and V774, V774 and C775, one or more deletions in EGFR exon 20, or one or more insertions in EGFR exon 20, or any combination thereof.

In one embodiment the mutant KRAS comprises a G12V, G12C, G12A or G12D substitution, or any combination thereof.

In one embodiment the cancer is lung cancer, gastric cancer, colorectal cancer, brain cancer, cancer derived from epithelial cells, breast cancer, ovarian cancer, colorectal cancer, anal cancer, prostate cancer, kidney cancer, bladder cancer, head and neck cancer, pharynx cancer, cancer of the nose, pancreatic cancer, skin cancer, oral cancer, cancer of the tongue, esophageal cancer, vaginal cancer, cervical cancer, cancer of the spleen, testicular cancer, gastric cancer, cancer of the thymus, colon cancer, thyroid cancer, liver cancer, hepatocellular carcinoma (HCC) or sporadic or hereditary papillary renal cell carcinoma (PRCC), or any combination thereof.

In one embodiment lung cancer is non-small cell lung cancer (NSCLC), small cell lung cancer (SCLC) or lung adenocarcinoma, pulmonary sarcomatoid carcinoma or any combination thereof.

In one embodiment the method comprises further administering one or more anti-cancer therapies to the subject.

In one embodiment the one or more anti-cancer therapies comprises chemotherapy, radiation therapy, surgery, a targeted anti-cancer therapy or a kinase inhibitor, or any combination thereof.

In one embodiment the kinase inhibitor is an inhibitor of EGFR, an inhibitor of c-Met, an inhibitor of HER2, an inhibitor of HER3, an inhibitor of HER4, an inhibitor of VEGFR or an inhibitor of AXL.

In one embodiment the kinase inhibitor is erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib.

In one embodiment the c-Met exon 14 skipping mutation is a de novo mutation.

In one embodiment the c-Met exon 14 skipping mutation is an acquired mutation.

In one embodiment the bispecific anti-EGFR/c-Met antibody is administered at a dose of between about 140 mg to about 1750 mg.

In one embodiment the bispecific anti-EGFR/c-Met antibody is administered at a dose of about 700 mg, about 750 mg, about 800 mg, about 850 mg, 900 mg, 950 mg, 1000 mg, 1050 mg, 1100 mg, 1150 mg, 1200 mg, 1250 mg, 1300 mg, 1350 mg or 1400 mg.

In one embodiment the bispecific anti-EGFR/c-Met antibody is administered twice a week, once a week, once in two weeks, once in three weeks or once in four weeks.

DETAILED DESCRIPTION

Definitions

Figure 1:
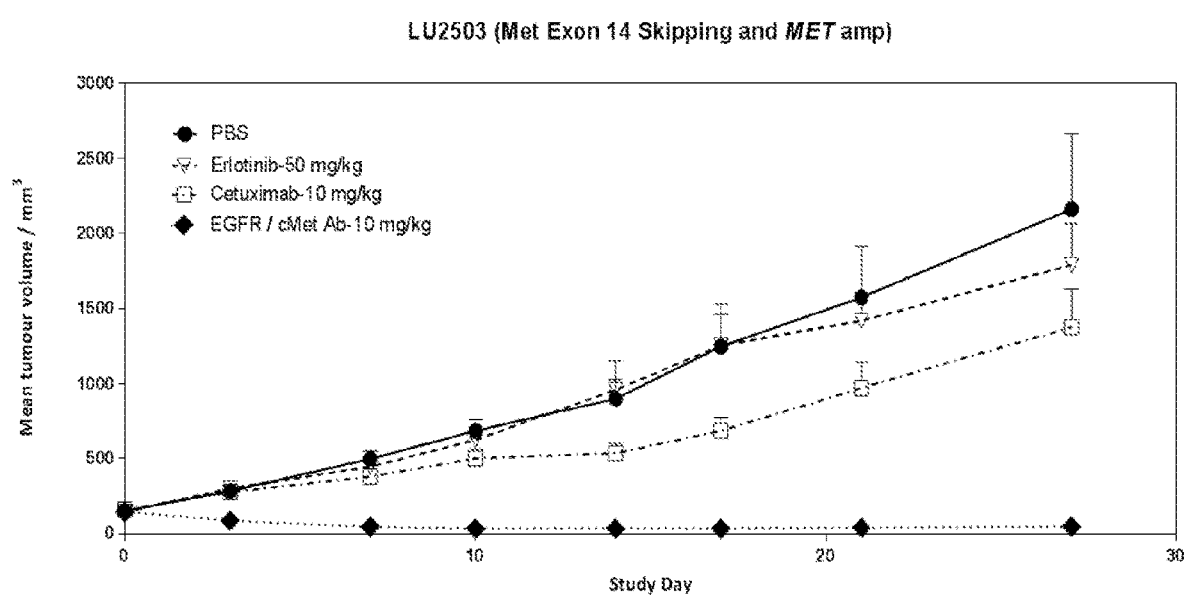
FIG. 1 shows efficacy of EGFR/c-Met antibody (JNJ-372) in a tumor model harboring c-Met exon 14 skipping mutation. Shrinkage of tumors were evident in JNJ-372 treated mice whereas tumors expanded in erlotinib or cetuximab treated animals.

All publications, including but not limited to patents and patent applications, cited in this specification are herein incorporated by reference as though fully set forth.

It is to be understood that the terminology used herein is for describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

As used in this specification and the appended claims, the singular forms "a," "an," and "the" include plural referents unless the content clearly dictates otherwise. Thus, for example, reference to "a cell" includes a combination of two or more cells, and the like.

The conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of."

"Co-administration," "administration with," "administration in combination with," "in combination with" or the like, encompass administration of the selected therapeutics or drugs to a single patient, and are intended to include treatment regimens in which the therapeutics or drugs are administered by the same or different route of administration or at the same or different time.

"Isolated" refers to a homogenous population of molecules (such as synthetic polynucleotides, polypeptides vectors or viruses) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Treat", "treating" or "treatment" of a disease or disorder such as cancer refers to accomplishing one or more of the following: reducing the severity and/or duration of the disorder, inhibiting worsening of symptoms characteristic of the disorder being treated, limiting or preventing recurrence of the disorder in subjects that have previously had the disorder, or limiting or preventing recurrence of symptoms in subjects that were previously symptomatic for the disorder.

"Prevent", "preventing", "prevention", or "prophylaxis" of a disease or disorder means preventing that a disorder occurs in subject.

"Diagnosing" or "diagnosis" refers to methods to determine if a subject is suffering from a given disease or condition or may develop a given disease or condition in the future or is likely to respond to treatment for a prior diagnosed disease or condition, i.e., stratifying a patient population on likelihood to respond to treatment. Diagnosis is typically performed by a physician based on the general guidelines for the disease to be diagnosed or other criteria that indicate a subject is likely to respond to a particular treatment.

"Responsive", "responsiveness" or "likely to respond" refers to any kind of improvement or positive response, such as alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable.

"Newly diagnosed" refers to a subject who has been diagnosed with EGFR or c-Met expressing cancer but has not yet received treatment for multiple myeloma.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

"Refractory" refers to a disease that does not respond to a treatment. A refractory disease can be resistant to a treatment before or at the beginning of the treatment, or a refractory disease can become resistant during a treatment.

"Relapsed" refers to the return of a disease or the signs and symptoms of a disease after a period of improvement after prior treatment with a therapeutic.

"Subject" includes any human or nonhuman animal "Nonhuman animal" includes all vertebrates, e.g., mammals and non-mammals, such as nonhuman primates, sheep, dogs, cats, horses, cows, chickens, amphibians, reptiles, etc. The terms "subject" and "patient" are used interchangeably herein.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Cancer" refers to an abnormal growth of cells which tend to proliferate in an uncontrolled way and, in some cases, to metastasize (spread) to other areas of a patient's body.

"EGFR or c-Met expressing cancer" refers to cancer that has detectable expression of EGFR or c-Met or has EGFR or c-Met mutation or amplification. EGFR or c-Met expression, amplification and mutation status can be detected using know methods, such as sequencing, fluorescent in situ hybridization, immunohistochemistry, flow cytometry or western blotting using tumor biopsies or blood samples. Expression can also be detected by sequening from circulating tumor DNA (ctDNA).

"Epidermal growth factor receptor" or "EGFR" refers to the human EGFR (also known as HER1 or ErbB1 (Ullrich et al., Nature 309:418-425, 1984) having the amino acid sequence shown in GenBank accession number NP_005219, as well as naturally-occurring variants thereof.

"Hepatocyte growth factor receptor" or "c-Met" or "MET" as used herein refers to the human c-Met having the amino acid sequence shown in GenBank Accession No: NP_001120972 and natural variants thereof.

"Bispecific anti-EGFR/c-Met antibody" or "bispecific EGFR/c-Met antibody" refers to a bispecific antibody having a first domain that specifically binds EGFR and a second domain that specifically binds c-Met. The domains specifically binding EGFR and c-Met are typically VH/VL pairs, and the bispecific anti-EGFR/c-Met antibody is monovalent in terms of binding to EGFR and c-Met.

"Specific binding" or "specifically binds" or "specifically binding" or "binds" refer to an antibody binding to an antigen or an epitope within the antigen with greater affinity than for other antigens. Typically, the antibody binds to the antigen or the epitope within the antigen with an equilibrium dissociation constant ($K_D$) of about $5\times10^{-8}$M or less, for example about $1\times10^{-9}$ M or less, about $1\times10^{-10}$ M or less, about $1\times10^{-11}$ M or less, or about $1\times10^{-12}$ M or less, typically with the $K_D$ that is at least one hundred-fold less than its $K_D$ for binding to a non-specific antigen (e.g., BSA, casein). The dissociation constant may be measured using known protocols. Antibodies that bind to the antigen or the epitope within the antigen may, however, have cross-reactivity to other related antigens, for example to the same antigen from other species (homologs), such as human or monkey, for example *Macaca fascicularis* (cynomolgus, cyno) or *Pan troglodytes* (chimpanzee, chimp). While a monospecific antibody binds one antigen or one epitope, a bispecific antibody binds two distinct antigens or two distinct epitopes.

"Antibodies" is meant in a broad sense and includes immunoglobulin molecules including monoclonal antibodies including murine, human, humanized and chimeric monoclonal antibodies, antigen binding fragments, multispecific antibodies, such as bispecific, trispecific, tetraspecific etc., dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Complementarity determining regions" (CDR) are antibody regions that bind an antigen. CDRs may be defined using various delineations such as Kabat (Wu et al. (1970) *J Exp Med* 132: 211-50) (Kabat et al., Sequences of Proteins of Immunological Interest, 5th Ed. Public Health Service, National Institutes of Health, Bethesda, Md., 1991), Chothia (Chothia et al. (1987) *J Mol Biol* 196: 901-17), IMGT (Lefranc et al. (2003) *Dev Comp Immunol* 27: 55-77) and AbM (Martin and Thornton (1996) *J Bmol Biol* 263: 800-15). The correspondence between the various delineations and variable region numbering are described (see e.g. Lefranc et al. (2003) *Dev Comp Immunol* 27: 55-77; Honegger and Pluckthun, (2001) *J Mol Biol* 309:657-70; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains.

"Antigen binding fragment" refers to a portion of an immunoglobulin molecule that binds an antigen. Antigen binding fragments may be synthetic, enzymatically obtainable or genetically engineered polypeptides and include the VH, the VL, the VH and the VL, Fab, F(ab')2, Fd and Fv fragments, domain antibodies (dAb) consisting of one VH domain or one VL domain, shark variable IgNAR domains, camelized VH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Recombinant" refers to DNA, antibodies and other proteins that are prepared, expressed, created or isolated by recombinant means when segments from different sources are joined to produce recombinant DNA, antibodies or proteins.

"Bispecific" refers to an antibody that specifically binds two distinct antigens or two distinct epitopes within the same antigen. The bispecific antibody may have cross-reactivity to other related antigens, for example to the same antigen from other species (homologs), such as human or monkey, for example *Macaca cynomolgus* (cynomolgus, cyno) or *Pan troglodytes*, or may bind an epitope that is shared between two or more distinct antigens.

"Antagonist" or "inhibitor" refers to a molecule that, when bound to a cellular protein, suppresses at least one reaction or activity that is induced by a natural ligand of the protein. A molecule is an antagonist when the at least one reaction or activity is suppressed by at least about 20%, 30%, 40%, 45%, 50%, 55%, 60%, 65%, 70%, 75%, 80%, 85%, 90%, 95%, or 100% more than the at least one reaction or activity suppressed in the absence of the antagonist (e.g., negative control), or when the suppression is statistically significant when compared to the suppression in the absence of the antagonist.

"PD-(L)1 axis inhibitor" refers to a molecule that inhibits PD-1 downstream signaling. PD-(L)1 axis inhibitor may be a molecule that binds PD-1, PD-L1 or PD-L2.

"Biological sample" refers to a collection of similar fluids, cells, or tissues isolated from a subject, as well as fluids, cells, or tissues present within a subject. Exemplary samples are biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium, lavage fluids and the like, tissue biopsies, tumor tissue biopsies, tumor tissue samples, fine needle aspirations, surgically resected tissue, organ cultures or cell cultures.

"Low fucose" or "low fucose content" as used in the application refers to antibodies with fucose content of about between 1%-15%.

"Normal fucose" or 'normal fucose content" as used herein refers to antibodies with fucose content of about over 50%, typically about over 80% or over 85%.

"c-Met exon 14 deletion" or "c-Met exon 14 skipping mutation" refers to a c-Met gene that is mutated to remove at least a portion of exon 14 of c-Met, or a c-Met transcript that is spliced to remove at least a portion of exon 14 of c-Met. The portion deleted may include a portion that encodes the negative regulation site Tyr 1003 in the juxtamembrane region of the c-Met protein. The exon 14 region of c-Met gene encompasses nucleotides 3284 to 3424 in the full-length nucleotide sequences of GenBank Accession No. NM_000245, or residues 964 to 1009 in the full-length c-Met amino acid sequences of GenBank Accession No. NP_000236. Various mutations at the DNA level can result in exon 14 skipping (see, e.g., Kong-Beltran et al. (2006) Cancer Res. 66; Dhanasekharan et al. (2014) Nature Communication 10:1038; Awad et al., J Clin Oncology 34: 721, 2016). Exon 14 of c-Met encodes 47 amino acids.

"Pharmaceutical composition" refers to a composition comprising an active ingredient such as the bispecific EGFR/c-Met antibody and one or more pharmaceutically acceptable carriers, or such as the EGFR TK inhibitor capmatinib, or solvate, hydrate, tautomer, or a pharmaceutically acceptable salt thereof, and one or more pharmaceutically acceptable carriers.

"Pharmaceutically acceptable carrier" or "excipient" refers to an ingredient in a pharmaceutical composition, other than the active ingredient, which is nontoxic to a subject. A pharmaceutically acceptable carrier includes, but is not limited to, a buffer, stabilizer or preservative. A pharmaceutically acceptable carrier includes, but is not limited to, a diluent, disintegrant, or glidant; or a diluent, disintegrant, wetting agent, glidant or lubricant.

"Solvates" and "hydrates" are solvent addition forms which the compounds of the present invention are able to form, whereby the multicomponent compound comprises both the host molecule (e.g., compound of Formula (I) or salt thereof) and guest molecule (water ("hydrate") or another solvent ("solvate")) incorporated in the structure.

"Tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganization of some of the bonding electrons.

Methods of the Disclosure

JNJ-61186372 (JNJ-372) is an IgG1 anti-EGFR/c-Met bispecific antibody, also known as Amivantamab, described in U.S. Pat. No. 9,593,164.

The disclosure is based, at least in part, on the finding that JNJ-372 is effective in treating subjects having c-Met exon skipping mutation.

c-Met exon 14 skipping mutations comprise point mutations, insertions, deletions and complex mutations such as combinations of insertions and deletions which affect splice acceptor or donor sites and induce in-frame exon 14 skipping, resulting in deletion of the juxtamembrane domain of c-Met, a known c-Met negative regulatory domain (see e.g. Descarentries et al., J Thoracic oncology 13: 1873-1883, 2018), resulting in constitutively active c-Met. Over 160 mutations affecting c-Met exon 14 has been described (see e.g. Cortot et al., J Natl Cancer Insti 109: djw262, 2017). C-Met exon 14 skipping mutations can be identified using next-generation sequencing (NGS) of patient samples. Exon 14 skipping mutations may arise de novo or as resistance mutations to prior treatment, such as to $3^{rd}$ generation TKIs. c-Met exon 14 encodes an amino acid sequence of

DLGSELVRYDARVHTPHL-
DRLVSARSVSPTTEMVSNESVDYRATFPE (SEQ ID NO: 21).

The disclosure provides a method of treating a subject having cancer that is positive for a c-Met exon 14 skipping mutation, comprising administering a therapeutically effective amount of an isolated bispecific anti-epidermal growth factor receptor (EGFR)/hepatocyte growth factor receptor (c-Met) antibody to the subject having cancer that is positive for c-Met exon 14 skipping mutation.

Cancers in which c-Met exon 14 skipping mutations have been identified include lung cancer, gastric cancer, colorectal cancer, and brain cancers, such as non-small cell lung cancer (NSCLC), small cell lung cancer (SCLC), lung adenocarcinoma, and pulmonary sarcomatoid carcinoma (PSC). Any other cancer harboring the c-Met exon skipping mutation may also be treated with the bispecific EGFR/c-Met antibody of the disclosure.

The disclosure also provides a method of treating a subject having lung cancer that is positive for a c-Met exon 14 skipping mutation, comprising administering a therapeutically effective amount of an isolated bispecific anti-EGFR/c-Met antibody to the subject having lung cancer that is positive for c-Met exon 14 skipping mutation.

The disclosure also provides a method of treating a subject having NSCLC that is positive for a c-Met exon 14 skipping mutation, comprising administering a therapeutically effective amount of an isolated bispecific anti-EGFR/c-Met antibody to the subject having NSCLC that is positive for c-Met exon 14 skipping mutation.

The disclosure also provides a method of treating a subject having SCLC that is positive for a c-Met exon 14 skipping mutation, comprising administering a therapeutically effective amount of an isolated bispecific anti-EGFR/c-Met antibody to the subject having SCLC that is positive for c-Met exon 14 skipping mutation.

The disclosure also provides a method of treating a subject having lung adenocarcinoma that is positive for a c-Met exon 14 skipping mutation, comprising administering a therapeutically effective amount of an isolated bispecific anti-EGFR/c-Met antibody to the subject having lung adenocarcinoma that is positive for c-Met exon 14 skipping mutation.

The disclosure also provides a method of treating a subject having PSC that is positive for a c-Met exon 14 skipping mutation, comprising administering a therapeutically effective amount of an isolated bispecific anti-EGFR/c-Met antibody to the subject having PSC that is positive for c-Met exon 14 skipping mutation.

The disclosure also provides a method of treating a subject having gastric cancer that is positive for a c-Met exon 14 skipping mutation, comprising administering a therapeutically effective amount of an isolated bispecific anti-EGFR/c-Met antibody to the subject having gastric cancer that is positive for c-Met exon 14 skipping mutation.

The disclosure also provides a method of treating a subject having colorectal cancer that is positive for a c-Met exon 14 skipping mutation, comprising administering a therapeutically effective amount of an isolated bispecific anti-EGFR/c-Met antibody to the subject having colorectal cancer that is positive for c-Met exon 14 skipping mutation.

The disclosure also provides a method of treating a subject having brain cancer that is positive for a c-Met exon 14 skipping mutation, comprising administering a therapeutically effective amount of an isolated bispecific anti-EGFR/c-Met antibody to the subject having brain cancer that is positive for c-Met exon 14 skipping mutation.

The disclosure also provides a method treating a subject having cancer with a bispecific anti-EGFR/c-Met antibody, comprising:
  providing a biological sample from the subject;
  determining presence or absence of a c-Met exon 14 skipping mutation in the sample;
  administering or providing for administration the bispecific anti-EGFR/c-Met antibody to the subject determined to have c-Met exon 14 skipping mutation.

In some embodiments, the biological sample is a blood sample.

In some embodiments, the biological sample is a tumor tissue biopsy

In some embodiments, the bispecific anti-EGFR/c-Met antibody comprises a first domain that specifically binds EGFR and a second domain that specifically binds c-Met, wherein the first domain comprises a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6; and the second domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

In some embodiments, the first domain that specifically binds EGFR comprises a heavy chain variable region (VH) of SEQ ID NO: 13 and a light chain variable region (VL) of SEQ ID NO: 14; and the second domain that specifically binds c-Met comprises the VH of SEQ ID NO: 15 and the VL of SEQ ID NO: 16.

In some embodiments, the bispecific anti-EGFR/c-Met antibody is an IgG1 isotype.

In some embodiments, the bispecific anti-EGFR/c-Met antibody comprises a first heavy chain (HC1) of SEQ ID NO: 17, a first light chain (LC1) of SEQ ID NO: 18, a second heavy chain (HC2) of SEQ ID NO: 19 and a second light chain (LC2) of SEQ ID NO: 20.

In some embodiments, the bispecific anti-EGFR/c-Met antibody comprises a biantennary glycan structure with a fucose content of about between 1% to about 15%.

Antibodies with reduced fucose content can be made using different methods reported to lead to the successful expression of relatively high defucosylated antibodies bearing the biantennary complex-type of Fc oligosaccharides such as control of culture osmolality (Konno et al., Cytotechnology 64(:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the cc 1,6-fucosyltrasferase (FUT8) gene (Mori et al., Biotechnol Bioeng 88:901-908, 2004), or coexpression of β-1,4-N-acetylglucosaminyltransferase III and Golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008). In general, lowering fucose content in the glycan of the antibodies potentiates antibody-meidated cellular cytotoxicity (ADCC).

The disclosure also provides a method of treating a subject having cancer that is positive for a c-Met exon 14 skipping mutation, comprising administering a therapeutically effective amount of an isolated bispecific anti-EGFR/c-Met antibody to the subject having cancer that is positive for c-Met exon 14 skipping mutation, wherein the bispecific anti-EGFR/c-Met antibody comprises a first domain that specifically binds EGFR and a second domain that specifically binds c-Met, wherein the first domain comprises a HCDR1 of SEQ ID NO: 1, a HCDR2 of SEQ ID NO: 2, a HCDR3 of SEQ ID NO: 3, a LCDR1 of SEQ ID NO: 4, a LCDR2 of SEQ ID NO: 5 and a LCDR3 of SEQ ID NO: 6;

and the second domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

The disclosure also provides a method of treating a subject having lung cancer that is positive for a c-Met exon 14 skipping mutation, comprising administering a therapeutically effective amount of an isolated bispecific anti-EGFR/c-Met antibody to the subject having lung cancer that is positive for c-Met exon 14 skipping mutation, wherein the bispecific anti-EGFR/c-Met antibody comprises a first domain that specifically binds EGFR and a second domain that specifically binds c-Met, wherein the first domain comprises a HCDR1 of SEQ ID NO: 1, a HCDR2 of SEQ ID NO: 2, a HCDR3 of SEQ ID NO: 3, a LCDR1 of SEQ ID NO: 4, a LCDR2 of SEQ ID NO: 5 and a LCDR3 of SEQ ID NO: 6; and the second domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

The disclosure also provides a method of treating a subject having NSCLC that is positive for a c-Met exon 14 skipping mutation, comprising administering a therapeutically effective amount of an isolated bispecific anti-EGFR/c-Met antibody to the subject having NSCLC that is positive for c-Met exon 14 skipping mutation, wherein the bispecific anti-EGFR/c-Met antibody comprises a first domain that specifically binds EGFR and a second domain that specifically binds c-Met, wherein the first domain comprises a HCDR1 of SEQ ID NO: 1, a HCDR2 of SEQ ID NO: 2, a HCDR3 of SEQ ID NO: 3, a LCDR1 of SEQ ID NO: 4, a LCDR2 of SEQ ID NO: 5 and a LCDR3 of SEQ ID NO: 6; and the second domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

The disclosure also provides a method of treating a subject having SCLC that is positive for a c-Met exon 14 skipping mutation, comprising administering a therapeutically effective amount of an isolated bispecific anti-EGFR/c-Met antibody to the subject having SCLC that is positive for c-Met exon 14 skipping mutation, wherein the bispecific anti-EGFR/c-Met antibody comprises a first domain that specifically binds EGFR and a second domain that specifically binds c-Met, wherein the first domain comprises a HCDR1 of SEQ ID NO: 1, a HCDR2 of SEQ ID NO: 2, a HCDR3 of SEQ ID NO: 3, a LCDR1 of SEQ ID NO: 4, a LCDR2 of SEQ ID NO: 5 and a LCDR3 of SEQ ID NO: 6; and the second domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

The disclosure also provides a method of treating a subject having lung adenocarcinoma that is positive for a c-Met exon 14 skipping mutation, comprising administering a therapeutically effective amount of an isolated bispecific anti-EGFR/c-Met antibody to the subject having lung adenocarcinoma that is positive for c-Met exon 14 skipping mutation, wherein the bispecific anti-EGFR/c-Met antibody comprises a first domain that specifically binds EGFR and a second domain that specifically binds c-Met, wherein the first domain comprises a HCDR1 of SEQ ID NO: 1, a HCDR2 of SEQ ID NO: 2, a HCDR3 of SEQ ID NO: 3, a LCDR1 of SEQ ID NO: 4, a LCDR2 of SEQ ID NO: 5 and a LCDR3 of SEQ ID NO: 6; and the second domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

The disclosure also provides a method of treating a subject having PSC that is positive for a c-Met exon 14 skipping mutation, comprising administering a therapeutically effective amount of an isolated bispecific anti-EGFR/c-Met antibody to the subject having PSC that is positive for c-Met exon 14 skipping mutation, wherein the bispecific anti-EGFR/c-Met antibody comprises a first domain that specifically binds EGFR and a second domain that specifically binds c-Met, wherein the first domain comprises a HCDR1 of SEQ ID NO: 1, a HCDR2 of SEQ ID NO: 2, a HCDR3 of SEQ ID NO: 3, a LCDR1 of SEQ ID NO: 4, a LCDR2 of SEQ ID NO: 5 and a LCDR3 of SEQ ID NO: 6; and the second domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

The disclosure also provides a method of treating a subject having gastric cancer that is positive for a c-Met exon 14 skipping mutation, comprising administering a therapeutically effective amount of an isolated bispecific anti-EGFR/c-Met antibody to the subject having gastric cancer that is positive for c-Met exon 14 skipping mutation, wherein the bispecific anti-EGFR/c-Met antibody comprises a first domain that specifically binds EGFR and a second domain that specifically binds c-Met, wherein the first domain comprises a HCDR1 of SEQ ID NO: 1, a HCDR2 of SEQ ID NO: 2, a HCDR3 of SEQ ID NO: 3, a LCDR1 of SEQ ID NO: 4, a LCDR2 of SEQ ID NO: 5 and a LCDR3 of SEQ ID NO: 6; and the second domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

The disclosure also provides a method of treating a subject having colorectal cancer that is positive for a c-Met exon 14 skipping mutation, comprising administering a therapeutically effective amount of an isolated bispecific anti-EGFR/c-Met antibody to the subject having colorectal cancer that is positive for c-Met exon 14 skipping mutation, wherein the bispecific anti-EGFR/c-Met antibody comprises a first domain that specifically binds EGFR and a second domain that specifically binds c-Met, wherein the first domain comprises a HCDR1 of SEQ ID NO: 1, a HCDR2 of SEQ ID NO: 2, a HCDR3 of SEQ ID NO: 3, a LCDR1 of SEQ ID NO: 4, a LCDR2 of SEQ ID NO: 5 and a LCDR3 of SEQ ID NO: 6; and the second domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

The disclosure also provides a method of treating a subject having brain cancer that is positive for a c-Met exon 14 skipping mutation, comprising administering a therapeutically effective amount of an isolated bispecific anti-EGFR/c-Met antibody to the subject having brain cancer that is positive for c-Met exon 14 skipping mutation, wherein the bispecific anti-EGFR/c-Met antibody comprises a first domain that specifically binds EGFR and a second domain that specifically binds c-Met, wherein the first domain comprises a HCDR1 of SEQ ID NO: 1, a HCDR2 of SEQ ID NO: 2, a HCDR3 of SEQ ID NO: 3, a LCDR1 of SEQ ID NO: 4, a LCDR2 of SEQ ID NO: 5 and a LCDR3 of SEQ ID NO: 6; and the second domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

The disclosure provides a method of treating a subject having cancer that is positive for a c-Met exon 14 skipping mutation, comprising administering a therapeutically effective amount of an isolated bispecific anti-EGFR/c-Met antibody to the subject having cancer that is positive for c-Met exon 14 skipping mutation, wherein the bispecific anti-EGFR/c-Met antibody comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having lung cancer that is positive for a c-Met exon 14 skipping mutation, comprising administering a therapeutically effective amount of an isolated bispecific anti-EGFR/c-Met antibody to the subject having lung cancer that is positive for c-Met exon 14 skipping mutation, wherein the bispecific anti-EGFR/c-Met antibody comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having NSCLC that is positive for a c-Met exon 14 skipping mutation, comprising administering a therapeutically effective amount of an isolated bispecific anti-EGFR/c-Met antibody to the subject having NSCLC that is positive for c-Met exon 14 skipping mutation, wherein the bispecific anti-EGFR/c-Met antibody comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having SCLC that is positive for a c-Met exon 14 skipping mutation, comprising administering a therapeutically effective amount of an isolated bispecific anti-EGFR/c-Met antibody to the subject having SCLC that is positive for c-Met exon 14 skipping mutation, wherein the bispecific anti-EGFR/c-Met antibody comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having lung adenocarcinoma that is positive for a c-Met exon 14 skipping mutation, comprising administering a therapeutically effective amount of an isolated bispecific anti-EGFR/c-Met antibody to the subject having lung adenocarcinoma that is positive for c-Met exon 14 skipping mutation, wherein the bispecific anti-EGFR/c-Met antibody comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having PSC that is positive for a c-Met exon 14 skipping mutation, comprising administering a therapeutically effective amount of an isolated bispecific anti-EGFR/c-Met antibody to the subject having PSC that is positive for c-Met exon 14 skipping mutation, wherein the bispecific anti-EGFR/c-Met antibody comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having gastric cancer that is positive for a c-Met exon 14 skipping mutation, comprising administering a therapeutically effective amount of an isolated bispecific anti-EGFR/c-Met antibody to the subject having gastric cancer that is positive for c-Met exon 14 skipping mutation, wherein the bispecific anti-EGFR/c-Met antibody comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having colorectal cancer that is positive for a c-Met exon 14 skipping mutation, comprising administering a therapeutically effective amount of an isolated bispecific anti-EGFR/c-Met antibody to the subject having colorectal cancer that is positive for c-Met exon 14 skipping mutation, wherein the bispecific anti-EGFR/c-Met antibody comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having brain cancer that is positive for a c-Met exon 14 skipping mutation, comprising administering a therapeutically effective amount of an isolated bispecific anti-EGFR/c-Met antibody to the subject having brain cancer that is positive for c-Met exon 14 skipping mutation, wherein the bispecific anti-EGFR/c-Met antibody comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure provides a method of treating a subject having cancer that is positive for a c-Met exon 14 skipping mutation, comprising administering a therapeutically effective amount of an isolated bispecific anti-EGFR/c-Met antibody to the subject having cancer that is positive for c-Met exon 14 skipping mutation, wherein the bispecific anti-EGFR/c-Met antibody is an IgG1 isotype and comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having lung cancer that is positive for a c-Met exon 14 skipping mutation, comprising administering a therapeutically effective amount of an isolated bispecific anti-EGFR/c-Met antibody to the subject having lung cancer that is positive for c-Met exon 14 skipping mutation, wherein the bispecific anti-EGFR/c-Met antibody is an IgG1 isotype and comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having NSCLC that is positive for a c-Met exon 14 skipping mutation, comprising administering a therapeutically effective amount of an isolated bispecific anti-EGFR/c-Met antibody to the subject having NSCLC that is positive for c-Met exon 14 skipping mutation, wherein the bispecific anti-EGFR/c-Met antibody is an IgG1 isotype and comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having SCLC that is positive for a c-Met exon 14 skipping mutation, comprising administering a therapeutically effective amount of an isolated bispecific anti-EGFR/c-Met antibody to the subject having SCLC that is positive for c-Met exon 14 skipping mutation, wherein the bispecific anti-EGFR/c-Met antibody is an IgG1 isotype and comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having lung adenocarcinoma that is positive for a c-Met exon 14 skipping mutation, comprising administering a therapeutically effective amount of an isolated bispecific anti-EGFR/c-Met antibody to the subject having lung adenocarcinoma that is positive for c-Met exon 14 skipping mutation, wherein the bispecific anti-EGFR/c-Met antibody is an IgG1 isotype and comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having gastric cancer that is positive for a c-Met exon 14 skipping mutation, comprising administering a therapeutically effective amount of an isolated bispecific anti-EGFR/c-Met antibody to the subject having gastric cancer that is positive for c-Met exon 14 skipping mutation, wherein the bispecific anti-EGFR/c-Met antibody is an IgG1 isotype and comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having colorectal cancer that is positive for a c-Met exon 14 skipping mutation, comprising administering a therapeutically effective amount of an isolated bispecific anti-EGFR/c-Met antibody to the subject having colorectal cancer that is positive for c-Met exon 14 skipping mutation, wherein the bispecific anti-EGFR/c-Met antibody is an IgG1 isotype and comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

The disclosure also provides a method of treating a subject having brain cancer that is positive for a c-Met exon 14 skipping mutation, comprising administering a therapeutically effective amount of an isolated bispecific anti-EGFR/c-Met antibody to the subject having brain cancer that is positive for c-Met exon 14 skipping mutation, wherein the bispecific anti-EGFR/c-Met antibody is an IgG1 isotype and comprises a first domain that specifically binds EGFR and a second domain that specifically binds c-Met, wherein the first domain comprises a VH of SEQ ID NO: 13 and a VL of SEQ ID NO: 14; and the second domain comprises the VH of SEQ ID NO: 15 and the VL of SEQ ID NO: 16.

In some embodiments, the bispecific anti-EGFR/c-Met antibody is an IgG1 isotype. Some variation exists within the IgG1 constant domain (e.g. well-known allotypes), with variation at positions 214, 356, 358, 422, 431, 435 o 436 (residue numbering according to the EU numbering) (see e.g. IMGT Web resources; IMGT Repertoire (IG and TR); Proteins and alleles; allotypes). The bispecific anti-EGFR/c-Met antibody may be of any IgG1 allotype, such as G1m17, G1m3, Glml, G1m2, G1m27 or Glm28.

The disclosure also provides a method of treating a subject having cancer that is positive for a c-Met exon 14 skipping mutation, comprising administering a therapeutically effective amount of an isolated bispecific anti-EGFR/c-Met antibody to the subject having cancer that is positive for c-Met exon 14 skipping mutation, wherein the bispecific anti-EGFR/c-Met antibody comprises a HC1 of SEQ ID NO: 17, a LC1 of SEQ ID NO: 18, a HC2 of SEQ ID NO: 19 and a LC2 of SEQ ID NO: 20.

The disclosure also provides a method of treating a subject having lung cancer that is positive for a c-Met exon 14 skipping mutation, comprising administering a therapeutically effective amount of an isolated bispecific anti-EGFR/c-Met antibody to the subject having lung cancer that is positive for c-Met exon 14 skipping mutation, wherein the bispecific anti-EGFR/c-Met antibody comprises a HC1 of SEQ ID NO: 17, a LC1 of SEQ ID NO: 18, a HC2 of SEQ ID NO: 19 and a LC2 of SEQ ID NO: 20.

The disclosure also provides a method of treating a subject having NSCLC that is positive for a c-Met exon 14 skipping mutation, comprising administering a therapeutically effective amount of an isolated bispecific anti-EGFR/c-Met antibody to the subject having NSCLC that is positive for c-Met exon 14 skipping mutation, wherein the bispecific anti-EGFR/c-Met antibody comprises a HC1 of SEQ ID NO: 17, a LC1 of SEQ ID NO: 18, a HC2 of SEQ ID NO: 19 and a LC2 of SEQ ID NO: 20.

The disclosure also provides a method of treating a subject having SCLC that is positive for a c-Met exon 14 skipping mutation, comprising administering a therapeutically effective amount of an isolated bispecific anti-EGFR/c-Met antibody to the subject having SCLC that is positive for c-Met exon 14 skipping mutation, wherein the bispecific anti-EGFR/c-Met antibody comprises a HC1 of SEQ ID NO: 17, a LC1 of SEQ ID NO: 18, a HC2 of SEQ ID NO: 19 and a LC2 of SEQ ID NO: 20.

The disclosure also provides a method of treating a subject having lung adenocarcinoma that is positive for a c-Met exon 14 skipping mutation, comprising administering a therapeutically effective amount of an isolated bispecific anti-EGFR/c-Met antibody to the subject having lung adenocarcinoma that is positive for c-Met exon 14 skipping mutation, wherein the bispecific anti-EGFR/c-Met antibody comprises a HC1 of SEQ ID NO: 17, a LC1 of SEQ ID NO: 18, a HC2 of SEQ ID NO: 19 and a LC2 of SEQ ID NO: 20.

The disclosure also provides a method of treating a subject having PSC that is positive for a c-Met exon 14 skipping mutation, comprising administering a therapeutically effective amount of an isolated bispecific anti-EGFR/ c-Met antibody to the subject having PSC that is positive for c-Met exon 14 skipping mutation, wherein the bispecific anti-EGFR/c-Met antibody comprises a HC1 of SEQ ID NO: 17, a LC1 of SEQ ID NO: 18, a HC2 of SEQ ID NO: 19 and a LC2 of SEQ ID NO: 20.

The disclosure also provides a method of treating a subject having gastric cancer that is positive for a c-Met exon 14 skipping mutation, comprising administering a therapeutically effective amount of an isolated bispecific anti-EGFR/c-Met antibody to the subject having gastric cancer that is positive for c-Met exon 14 skipping mutation, wherein the bispecific anti-EGFR/c-Met antibody comprises a HC1 of SEQ ID NO: 17, a LC1 of SEQ ID NO: 18, a HC2 of SEQ ID NO: 19 and a LC2 of SEQ ID NO: 20.

The disclosure also provides a method of treating a subject having colorectal cancer that is positive for a c-Met exon 14 skipping mutation, comprising administering a therapeutically effective amount of an isolated bispecific anti-EGFR/c-Met antibody to the subject having colorectal cancer that is positive for c-Met exon 14 skipping mutation, wherein the bispecific anti-EGFR/c-Met antibody comprises a HC1 of SEQ ID NO: 17, a LC1 of SEQ ID NO: 18, a HC2 of SEQ ID NO: 19 and a LC2 of SEQ ID NO: 20.

The disclosure also provides a method of treating a subject having brain cancer that is positive for a c-Met exon 14 skipping mutation, comprising administering a therapeutically effective amount of an isolated bispecific anti-EGFR/ c-Met antibody to the subject having brain cancer that is positive for c-Met exon 14 skipping mutation, wherein the bispecific anti-EGFR/c-Met antibody comprises a HC1 of SEQ ID NO: 17, a LC1 of SEQ ID NO: 18, a HC2 of SEQ ID NO: 19 and a LC2 of SEQ ID NO: 20.

In some embodiments, the subject is relapsed or resistant to treatment with one or more prior anti-cancer therapies.

In some embodiments, the subject has acquired the c-Met exon 14 skipping mutation as a result of treatment with one or more prior anti-cancer therapies.

In some embodiments, the subject has acquired the c-Met exon 14 skipping mutation as a result of treatment with a kinase inhibitor.

In some embodiments, the subject has acquired the c-Met exon 14 skipping mutation as a result of treatment with an EGFR kinase inhibitor.

In some embodiments, the subject has acquired the c-Met exon 14 skipping mutation as a result of treatment with a c-Met kinase inhibitor.

In some embodiments, the one or more prior anti-cancer therapies comprises one or more chemotherapeutic agents, checkpoint inhibitors, targeted anti-cancer therapies or kinase inhibitors, or any combination thereof.

In some embodiments, the kinase inhibitor is an inhibitor of EGFR, an inhibitor of c-Met, an inhibitor of HER2, an inhibitor of HER3, an inhibitor of HER4, an inhibitor of VEGFR or an inhibitor of AXL.

In some embodiments, the kinase inhibitor is erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib.

In some embodiments, the one or more prior anti-cancer therapies comprises carboplatin, paclitaxel, gemcitabine, cisplatin, vinorelbine, docetaxel, palbociclib, crizotinib, PD-(L)1 axis inhibitor, an inhibitor of EGFR, an inhibitor of c-Met, an inhibitor of HER2, an inhibitor of HER3, an inhibitor of HER4, an inhibitor of VEGFR, an inhibitor of AXL, erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib, or any combination thereof.

In some embodiments, the subject is resistant or has acquired resistance to an EGFR inhibitor. Exemplary EGFR inhibitors for which cancer may acquire resistance are anti-EGFR antibodies cetuximab (ERBITUX®), pantinumumab (VECTIBIX®), matuzumab, nimotuzumab, small molecule EGFR inhibitors erlotinib (TARCEVA®), gefitinib (IRESSA®), EKB-569 (pelitinib, irreversible EGFR TKI), pan-ErbB and other receptor tyrosine kinase inhibitors, lapatinib (EGFR and HER2 inhibitor), pelitinib (EGFR and HER2 inhibitor), vandetanib (ZD6474, ZACTIMA™, EGFR, VEGFR2 and RET TKI), PF00299804 (dacomitinib, irreversible pan-ErbB TKI), CI-1033 (irreversible pan-erbB TKI), afatinib (BIBW2992, irreversible pan-ErbB TKI), AV-412 (dual EGFR and ErbB2 inhibitor), EXEL-7647 (EGFR, ErbB2, GEVGR and EphB4 inhibitor), CO-1686 (irreversible mutant-selective EGFR TKI), AZD9291 (irreversible mutant-selective EGFR TKI), and HKI-272 (neratinib, irreversible EGFR/ErbB2 inhibitor).

Various qualitative and/or quantitative methods may be used to determine if a subject is resistant, has developed or is susceptible to developing a resistance to treatment with an anti-cancer therapy. Symptoms that may be associated with resistance to an anti-cancer therapy include a decline or plateau of the well-being of the patient, an increase in the size of a tumor, arrested or slowed decline in growth of a tumor, and/or the spread of cancerous cells in the body from one location to other organs, tissues or cells. Re-establishment or worsening of various symptoms associated with cancer may also be an indication that a subject has developed or is susceptible to developing resistance to an anti-cancer therapy, such as anorexia, cognitive dysfunction, depression, dyspnea, fatigue, hormonal disturbances, neutropenia, pain, peripheral neuropathy, and sexual dysfunction. The symptoms associated with cancer may vary according to the type of cancer. For example, symptoms associated with cervical cancer may include abnormal bleeding, unusual heavy vaginal discharge, pelvic pain that is not related to the normal menstrual cycle, bladder pain or pain during urination, and bleeding between regular menstrual periods, after sexual intercourse, douching, or pelvic exam Symptoms associated with lung cancer may include persistent cough, coughing up blood, shortness of breath, wheezing chest pain, loss of appetite, losing weight without trying and fatigue. Symptoms for liver cancer may include loss of appetite and weight, abdominal pain, especially in the upper right part of abdomen that may extend into the back and shoulder, nausea and vomiting, general weakness and fatigue, an enlarged liver, abdominal swelling (ascites), and a yellow discoloration of the skin and the whites of eyes (jaundice). One skilled in oncology may readily identify symptoms associated with a particular cancer type.

Exemplary PD-(L)1 axis inhibitors are antibodies that bind PD-1 such as nivolumab (OPDIVO®), pembrolimumab (KEYTRUDA), sintilimab, cemiplimab (LIBTAYO®), tripolibamab, tislelizumab, spartalizumab, camrelizumab, dostralimab, genolimzumab or cetrelimab, or antibodies that bind PD-L1, such as PD-L1 antibodies are envafolimab, atezolizumab (TECENTRIQ), durvalumab (IMFINZI®) and avelumab (BAVENCIO®).

Marketed antibodies may be purchased via authorized distributor or pharmacy. The amino acid sequences structures of the small molecules can be found from USAN and/or INN submissions by the companies of from CAS registry.

In some embodiments, the subject is treatment naïve.

In some embodiments, the c-Met exon 14 skipping mutation is a de novo mutation.

In some embodiments, cancer that is positive for c-Met exon 14 skipping mutation is positive for CDK4 amplification, EGFR amplification, KRAS amplification, MDM2 amplification, TERT amplification, NF1 R2450*; RAD50 L597Vfs*5, MET c.3082+3A>G, EGFR, wild-type EGFR, an EGFR activating mutation, increased levels of circulating HGF, c-MET amplification or a mutant KRAS, or any combination thereof.

EGFR activating mutations that may be associated with cancer include point mutations, deletion mutations, insertion mutations, inversions or gene amplifications that lead to an increase in at least one biological activity of EGFR, such as elevated tyrosine kinase activity, formation of receptor homodimers and heterodimers, enhanced ligand binding etc. Mutations can be located in any portion of an EGFR gene or regulatory region associated with an EGFR gene and include mutations in exon 18, 19, 20 or 21 or mutations in the kinase domain. Other examples of EGFR activating mutations are known in the art (see e.g., U.S. Pat. Publ. No. US2005/0272083). Information about EGFR and other ErbB receptors including receptor homo- and hetero-dimers, receptor ligands, autophosphorylation sites, and signaling molecules involved in ErbB mediated signaling is known in the art (see e.g., Hynes and Lane, Nature Reviews Cancer 5: 341-354, 2005).

In some embodiments, the EGFR activating mutation comprises L718Q, G719A, G719X (X being any amino acid), L861X (X being any amino acid), L858R, E746K, L747S, E749Q, A750P, A755V, V765M, C797S, L858P or T790M substitution, deletion of E746-A750, deletion of R748-P753, insertion of Ala (A) between M766 and A767, insertion of Ser, Val and Ala (SVA) between 5768 and V769, insertion of Asn and Ser (NS) between P772 and H773, insertion of one or more amino acids between D761 and E762, A763 and Y764, Y764 and Y765, M766 and A767, A767 and V768, S768 and V769, V769 and D770, D770 and N771, N771 and P772, P772 and H773, H773 and V774, V774 and C775, one or more deletions in EGFR exon 20, or one or more insertions in EGFR exon 20, or any combination thereof. Subjects with EGFR exon 20 mutations (insertion of one or more amino acids) are generally resistant to EGFR tyrosine kinase inhibitors (TKI) (see. e.g. Int. Pat. Publ. No. WO2018/094225).

Exemplary c-Met activating mutations include point mutations, deletion mutations, insertion mutations, inversions or gene amplifications that lead to an increase in at least one biological activity of a c-Met protein, such as elevated tyrosine kinase activity, formation of receptor homodimers and heterodimers, enhanced ligand binding etc. Mutations can be located in any portion of the c-Met gene or regulatory regions associated with the gene, such as mutations in the kinase domain of c-Met. Exemplary c-Met activating mutations are mutations at residue positions N375, V13, V923, R175, V136, L229, S323, R988, S1058/T1010 and E168. Methods for detecting EGFR and c-Met mutations or gene amplifications are well known.

In some embodiments, the mutant KRAS comprises a G12V, G12C, G12A, or G12D substitution, or any combination thereof.

In some embodiments, cancer that is positive for a c-Met exon 14 skipping mutation comprises lung cancer, gastric cancer, colorectal cancer, brain cancer, derived from epithelial cell cancer, breast cancer, ovarian cancer, colorectal cancer, anal cancer, prostate cancer, kidney cancer, bladder cancer, head and neck cancer, pharynx cancer, cancer of the nose, pancreatic cancer, skin cancer, oral cancer, cancer of the tongue, esophageal cancer, vaginal cancer, cervical cancer, cancer of the spleen, testicular cancer, gastric cancer, cancer of the thymus, colon cancer, thyroid cancer, liver cancer, hepatocellular carcinoma (HCC) or sporadic or hereditary papillary renal cell carcinoma (PRCC), or any combination thereof. In some embodiments, cancer that is positive for a c-Met exon 14 skipping mutation comprises lung cancer. In some embodiments, cancer that is positive for a c-Met exon 14 skipping mutation comprises gastric cancer. In some embodiments, cancer that is positive for a c-Met exon 14 skipping mutation comprises colorectal cancer. In some embodiments, cancer that is positive for a c-Met exon 14 skipping mutation comprises brain cancer. In some embodiments, cancer that is positive for a c-Met exon 14 skipping mutation comprises epithelial cell cancer. In some embodiments, cancer that is positive for a c-Met exon 14 skipping mutation comprises breast cancer. In some embodiments, cancer that is positive for a c-Met exon 14 skipping mutation comprises ovarian cancer. In some embodiments, cancer that is positive for a c-Met exon 14 skipping mutation comprises colorectal cancer. In some embodiments, cancer that is positive for a c-Met exon 14 skipping mutation comprises anal cancer. In some embodiments, cancer that is positive for a c-Met exon 14 skipping mutation comprises prostate cancer. In some embodiments, cancer that is positive for a c-Met exon 14 skipping mutation comprises kidney cancer. In some embodiments, cancer that is positive for a c-Met exon 14 skipping mutation comprises bladder cancer. In some embodiments, cancer that is positive for a c-Met exon 14 skipping mutation comprises head and neck cancer. In some embodiments, cancer that is positive for a c-Met exon 14 skipping mutation comprises pharynx cancer. In some embodiments, cancer that is positive for a c-Met exon 14 skipping mutation comprises cancer of the nose. In some embodiments, cancer that is positive for a c-Met exon 14 skipping mutation comprises pancreatic cancer. In some embodiments, cancer that is positive for a c-Met exon 14 skipping mutation comprises skin cancer. In some embodiments, cancer that is positive for a c-Met exon 14 skipping mutation comprises oral cancer. In some embodiments, cancer that is positive for a c-Met exon 14 skipping mutation comprises cancer of the tongue. In some embodiments, cancer that is positive for a c-Met exon 14 skipping mutation comprises esophageal cancer. In some embodiments, cancer that is positive for a c-Met exon 14 skipping mutation comprises vaginal cancer. In some embodiments, cancer that is positive for a c-Met exon 14 skipping mutation comprises cervical cancer. In some embodiments, cancer that is positive for a c-Met exon 14 skipping mutation comprises cancer of the spleen. In some embodiments, cancer that is positive for a c-Met exon 14 skipping mutation comprises testicular cancer. In some embodiments, cancer that is positive for a c-Met exon 14 skipping mutation comprises gastric cancer. In some embodiments, cancer that is positive for a c-Met exon 14 skipping mutation comprises cancer of the thymus. In some embodiments, cancer that is positive for a c-Met exon 14 skipping mutation comprises colon cancer. In some embodiments, cancer that is positive for a c-Met exon 14 skipping mutation comprises thyroid cancer. In some embodiments, cancer that is positive for a c-Met exon 14 skipping mutation comprises liver cancer. In some embodiments, cancer that is positive for a c-Met exon 14 skipping mutation comprises hepatocellular carcinoma (HCC). In some embodiments, cancer that is positive for a c-Met exon 14 skipping mutation comprises sporadic or hereditary papillary renal cell carcinoma (PRCC).

In some embodiments, NSCLC includes squamous cell carcinoma, adenocarcinoma, and large cell carcinoma. In some embodiments, cells of the NSCLC have an epithelial phenotype. In some embodiments, the NSCLC has acquired resistance to treatment with one or more EGFR inhibitors.

In NSCLC, specific mutations in the EGFR gene are associated with high response rates (70-80%) to EGFR tyrosine kinase inhibitors (EGFR-TKIs). A 5 amino acid deletion in exon 19 or the point mutation L858R in EGFR are associated with EGFR-TKI sensitivity (Nakata and Gotoh, Expert Opin Ther Targets 16:771-781, 2012). These mutations result in a ligand-independent activation of the EGFR kinase activity. Activating EGFR mutations occur in 10-30% of NSCLC patients and are significantly more common in East Asians, women, never smokers, and patients with adenocarcinoma histology (Janne and Johnson Clin Cancer Res 12(14 Suppl): 4416s-4420s, 2006). EGFR gene amplification is also strongly correlated with response after EGFR-TKI treatment (Cappuzzo et al., J Natl Cancer Inst 97:643-55, 2005). EGFR exon 20 insertions have been associated with EGFR TKI resistance.

Although the majority of NSCLC patients with EGFR mutations initially respond to EGFR TKI therapy, virtually all acquire resistance that prevents a durable response. 50-60% of patients acquire resistance due to a second-site point mutation in the kinase domain of EGFR (T790M). Nearly 60% of all tumors that become resistant to EGFR tyrosine kinase inhibitors increase c-Met expression, amplify the c-Met gene, or increase its only known ligand, HGF (Turke et al., Cancer Cell, 17:77-88, 2010).

In some embodiments, the subject is further administering one or more anti-cancer therapies.

In some embodiments, the one or more anti-cancer therapies comprises chemotherapy, radiation therapy, surgery, a targeted anti-cancer therapy or a kinase inhibitor, or any combination thereof.

In some embodiments, the kinase inhibitor is an inhibitor of EGFR, an inhibitor of c-Met, an inhibitor of HER2, an inhibitor of HER3, an inhibitor of HER4, an inhibitor of VEGFR or an inhibitor of AXL. In some embodiments, the kinase inhibitor is an inhibitor of EGFR. In some embodiments, the kinase inhibitor is an inhibitor of c-Met. In some embodiments, the kinase inhibitor is an inhibitor of HER2. In some embodiments, the kinase inhibitor is an inhibitor of HER3. In some embodiments, the kinase inhibitor is an inhibitor of HER4. In some embodiments, the kinase inhibitor is an inhibitor of VEGFR. In some embodiments, the kinase inhibitor is an inhibitor of or AXL.

In some embodiments, the kinase inhibitor is erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib.

In some embodiments, the kinase inhibitor is erlotinib. In some embodiments, the kinase inhibitor is gefitinib. In some embodiments, the kinase inhibitor is lapatinib. In some embodiments, the kinase inhibitor is vandetanib. In some embodiments, the kinase inhibitor is afatinib. In some embodiments, the kinase inhibitor is osimertinib. In some embodiments, the kinase inhibitor is lazertinib. In some embodiments, the kinase inhibitor is poziotinib. In some embodiments, the kinase inhibitor is criotinib. In some embodiments, the kinase inhibitor is cabozantinib. In some embodiments, the kinase inhibitor is capmatinib. In some embodiments, the kinase inhibitor is axitinib. In some embodiments, the kinase inhibitor is lenvatinib. In some embodiments, the kinase inhibitor is nintedanib. In some embodiments, the kinase inhibitor is regorafenib. In some embodiments, the kinase inhibitor is pazopanib. In some embodiments, the kinase inhibitor is sorafenib. In some embodiments, the kinase inhibitor is sunitinib.

Anti-cancer therapies that may be administered in combination with the bispecific anti-EGFR/c-Met antibody in the methods of the disclosure include any one or more of the chemotherapeutic drugs or other anti-cancer therapeutics known to those of skill in the art. Chemotherapeutic agents are chemical compounds useful in the treatment of cancer and include growth inhibitory agents or other cytotoxic agents and include alkylating agents, anti-metabolites, anti-microtubule inhibitors, topoisomerase inhibitors, receptor tyrosine kinase inhibitors, angiogenesis inhibitors and the like. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-FU; folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; members of taxoid or taxane family, such as paclitaxel (TAXOL® docetaxel (TAXOTERE®) and analogues thereof; chlorambucil; gemcitabine; 6-thioguanine; mercaptopurine; methotrexate; platinum analogues such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; inhibitors of receptor tyrosine kinases and/or angiogenesis, including sorafenib (NEXAVAR®), sunitinib (SUTENT®), pazopanib (VOTRIENT™), toceranib (PALLADIA™), vandetanib (ZACTIMA™), cediranib (RECENTIN®), regorafenib (BAY 73-4506), axitinib (AG013736), lestaurtinib (CEP-701), erlotinib (TARCEVA®), gefitinib (IRESSA®), afatinib (BIBW 2992), lapatinib (TYKERB®), neratinib (HKI-272), and the like, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON®); and anti-androgens such as flutamide, nilutamide, bicalutamide, leuprolide, and goserelin; and pharmaceutically acceptable salts, acids or derivatives of any of the above. Other conventional cytotoxic chemical compounds as those disclosed in Wiemann et al., 1985, in Medical Oncology (Calabresi et aL, eds.), Chapter 10, McMillan Publishing, are also applicable to the methods of the present invention.

Administration

The bispecific anti-EGFR/c-Met antibody may be administered in a pharmaceutically acceptable carrier. "Carrier" refers to a diluent, adjuvant, excipient, or vehicle with which the antibody of the invention is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used to formulate the bispecific anti-EGFR/c-Met antibody. These solutions are sterile and generally free of particulate matter. They may be sterilized by conventional, well-known sterilization techniques (e.g., filtration). For parenteral administration, the carrier may comprise sterile water and other excipients may be added to increase solubility or preservation. Injectable suspensions or solutions may also be prepared utilizing aqueous carriers along with appropriate additives. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration may be any suitable route that delivers the bispecific anti-EGFR-c-Met antibody to the host, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intratumoral, intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

In some embodiments, the bispecific anti-EGFR/c-Met antibody is administered at a dose of between about 140 mg to about 1750 mg. In some embodiments, the bispecific anti-EGFR/c-Met antibody is administered at a dose of between about 140 mg to about 1750 mg.

In some embodiments, the bispecific anti-EGFR/c-Met antibody is administered at a dose of about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1000 mg, about 1010 mg, about 1020 mg, about 1030 mg, about 1040 mg, about 1050 mg, about 1060 mg, about 1070 mg, about 1080 mg, about 1090 mg, about 1100 mg, about 1110 mg, about 1120 mg, about 1130 mg, about 1140 mg, about 1150 mg, about 1160 mg, about 1170 mg, about 1180 mg, about 1190 mg, about 1200 mg, about 1210 mg, about 1220 mg, about 1230 mg, about 1240 mg, about 1250 mg, about 1260 mg, about 1270 mg, about 1280 mg, about 1290 mg, about 1300 mg, about 1310 mg, about 1320 mg, about 1330 mg, about 1340 mg, about 1350 mg, about 1360 mg, about 1370 mg, about 1380 mg, about 1390 mg, about 1400 mg, about 1410 mg, about 1420 mg, about 1430 mg, about 1440 mg, about 1450 mg, about 1460 mg, about 1470 mg, about 1480 mg, about 1490 mg, about 1500 mg, about 1510 mg, about 1520 mg, about 1530 mg, about 1540 mg, about 1550 mg, about 1560 mg, about 1570 mg, about 1580 mg, about 1590 mg, about 1600 mg, about 1610 mg, 1620 mg, about 1630 mg, about 1640 mg, about 1650 mg, about 1660 mg, about 1670 mg, about 1680 mg, about 1690 mg, about 1700 mg, about 1710 mg, about 1720 mg, about 1730 mg, about 1740 mg, about 1750 mg, about 1760 mg, about 1770 mg, about 1780 mg, about 1790 mg, about 1800 mg, about 1810 mg, about 1820 mg, about 1830 mg, about 1840 mg, about 1850 mg, about 1860 mg, about 1870 mg, about 1880 mg, 1890 mg, about 1900 mg, about 1910 mg, about 1920 mg, about 1930 mg, about 1940 mg, about 1950 mg, about 1960 mg, about 1970 mg, about 1980 mg, about 1990 mg or about 2000 mg.

In some embodiments, the bispecific anti-EGFR/c-Met antibody is administered at a dose of about 350 mg, about 700 mg, about 1050 mg or about 1400 mg. In some embodiments, the bispecific anti-EGFR/c-Met antibody is administered at a dose of about 350 mg. In some embodiments, the bispecific anti-EGFR/c-Met antibody is administered at a dose of about 700 mg. In some embodiments, the bispecific anti-EGFR/c-Met antibody is administered at a dose of about 750 mg. In some embodiments, the bispecific anti-EGFR/c-Met antibody is administered at a dose of about 800 mg. In some embodiments, the bispecific anti-EGFR/c-Met antibody is administered at a dose of about 850 mg. In some embodiments, the bispecific anti-EGFR/c-Met antibody is administered at a dose of about 900 mg. In some embodiments, the bispecific anti-EGFR/c-Met antibody is administered at a dose of about 950 mg. In some embodiments, the bispecific anti-EGFR/c-Met antibody is administered at a dose of about 1000 mg. In some embodiments, the bispecific anti-EGFR/c-Met antibody is administered at a dose of about 1050 mg. In some embodiments, the bispecific anti-EGFR/c-Met antibody is administered at a dose of about 1100 mg. In some embodiments, the bispecific anti-EGFR/c-Met antibody is administered at a dose of about 1150 mg. In some embodiments, the bispecific anti-EGFR/c-Met antibody is administered at a dose of about 1200 mg. In some embodiments, the bispecific anti-EGFR/c-Met antibody is administered at a dose of about 1250 mg. In some embodiments, the bispecific anti-EGFR/c-Met antibody is administered at a dose of about 1300 mg. In some embodiments, the bispecific anti-EGFR/c-Met antibody is administered at a dose of about 1350 mg. In some embodiments, the bispecific anti-EGFR/c-Met antibody is administered at a dose of about 1400 mg.

In some embodiments, the bispecific anti-EGFR/c-Met antibody is administered once a week. In some embodiments, the bispecific anti-EGFR/c-Met antibody is administered about 1050 mg once a week. In some embodiments, the bispecific anti-EGFR/c-Met antibody is administered about 1400 mg once a week.

In some embodiments, the bispecific anti-EGFR/c-Met antibody is administered once in two weeks. In some embodiments, the bispecific anti-EGFR/c-Met antibody is administered about 1050 mg once in two weeks. In some embodiments, the bispecific anti-EGFR/c-Met antibody is administered about 1400 mg once in two weeks.

In some embodiments, the bispecific anti-EGFR/c-Met antibody is administered twice a week. In some embodiments, the bispecific anti-EGFR/c-Met antibody is administered once a week. In some embodiments, the bispecific anti-EGFR/c-Met antibody is administered once in two weeks. In some embodiments, the bispecific anti-EGFR/c-Met antibody is administered once in three weeks. In some embodiments, the bispecific anti-EGFR/c-Met antibody is administered once in four weeks.

For combination therapies, the one or more anti-cancer agents may be administered using recommended doses and dosages of the anti-cancer agent.

Generation of Bispecific Anti-EGFR/c-Met Antibodies Used in the Methods of the Disclosure An exemplary bispecific anti-EGFR/c-Met antibody that can be used in the methods of the disclosures is JNJ-372. JNJ-372 is characterized by following amino acid sequences:

```
EGFR binding arm
(HCDR1, EGFR binding arm)
                                        SEQ ID NO: 1
TYGMH (HCDR2, EGFR binding arm)
                                        SEQ ID NO: 2
VIWDDGSYKYYGDSVKG (HCDR3, EGFR binding arm)
                                        SEQ ID NO: 3
DGITMVRGVMKDYFDY
```

-continued
```
(LCDR1, EGFR binding arm)
                                        SEQ ID NO: 4
RASQDISSALV (LCDR2, EGFR binding arm)
                                        SEQ ID NO: 5
DASSLES (LCDR3, EGFR binding arm)
                                        SEQ ID NO: 6
QQFNSYPLT (HCDR1, c-Met binding arm)
                                        SEQ ID NO: 7
SYGIS (HCDR2, c-Met binding arm)
                                        SEQ ID NO: 8
WISAYNGYTNYAQKLQG (HCDR3, c-Met binding arm)
                                        SEQ ID NO: 9
DLRGTNYFDY (LCDR1, c-Met binding arm)
                                        SEQ ID NO: 10
RASQGISNWLA (LCDR2, c-Met binding arm)
                                        SEQ ID NO: 11
AASSLLS (LCDR3, c-Met binding arm)
                                        SEQ ID NO: 12
QQANSFPIT (VH, EGFR binding arm)
                                        SEQ ID NO: 13
QVQLVESGGGVVQPGRSLRLSCAASGFTFSTYGMHWVRQAPGKGLEWVA
VIWDDGSYKYYGDSVKGRFTISRDNSKNTLYLQMNSLRAEDTAVYYCAR
DGITMVRGVMKDYFDYWGQGTLVTVSS (VL, EGFR binding arm)
                                        SEQ ID NO: 14
AIQLTQSPSSLSASVGDRVTITCRASQDISSALVWYQQKPGKAPKLLIY
DASSLESGVPSRFSGSESGTDFTLTISSLQPEDFATYYCQQFNSYPLTF
GGGTKVEIK (VH, c-Met binding arm)
                                        SEQ ID NO: 15
QVQLVQSGAEVKKPGASVKVSCETSGYTFTSYGISWVRQAPGHGLEWMG
WISAYNGYTNYAQKLQGRVTMTTDTSTSTAYMELRSLRSDDTAVYYCAR
DLRGTNYFDYWGQGTLVTVSS (VL, c-Met binding arm)
                                        SEQ ID NO: 16
DIQMTQSPSSVSASVGDRVTITCRASQGISNWLAWFQHKPGKAPKLLIY
AASSLLSGVPSRFSGSGSGTDFTLTISSLQPEDFATYYCQQANSFPITF
GQGTRLEIK HC1
                                        SEQ ID NO: 17
QVQLVESGGGVVQPGRSLRLSCAASGFTFSTYGMHWVRQAPGKGLEWVA
VIWDDGSYKYYGDSVKGRFTISRDNSKNTLYLQMNSLRAEDTAVYYCAR
DGITMVRGVMKDYFDYWGQGTLVTVSSASTKGPSVFPLAPSSKSTSGGT
AALGCLVKDYFPEPVTVSWNSGALTSGVHTFPAVLQSSGLYSLSSVVTV
PSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKT
ISKAKGQPREPQVYTLPPSREEMTKNQVSLTCLVKGFYPSDIAVEWESN
GQPENNYKTTPPVLDSDGSFLLYSKLTVDKSRWQQGNVFSCSVMHEALH
NHYTQKSLSLSPGK LC1
                                        SEQ ID NO: 18
AIQLTQSPSSLSASVGDRVTITCRASQDISSALVWYQQKPGKAPKLLIY
DASSLESGVPSRFSGSESGTDFTLTISSLQPEDFATYYCQQFNSYPLTF
GGGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC
```

HC2

SEQ ID NO: 19
QVQLVQSGAEVKKPGASVKVSCETSGYTFTSYGISWVRQAPGHGLEWMG
WISAYNGYTNYAQKLQGRVTMTTDTSTSTAYMELRSLRSDDTAVYYCAR
DLRGTNYFDYWGQGTLVTVSSASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENN
YKTTPPVLDSDGSFFLYSRLTVDKSRWQQGNVFSCSVMHEALHNHYTQK
SLSLSPGK

LC2

SEQ ID NO: 20
DIQMTQSPSSVSASVGDRVTITCRASQGISNWLAWFQHKPGKAPKLLIY
AASSLLSGVPSRFSGSGSGTDFTLTISSLQPEDFATYYCQQANSFPITF
GQGTRLEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC

Other bispecific anti-EGFR/c-Met antibodies publicly available may also be used in the methods of the disclosure as long as they demonstrate similar characteristics when compared to JNJ-372 as described in U.S. Pat. No. 9,593,164. Bispecific anti-EGFR/c-Met antibodies that may be used in the methods of the disclosure may also be generated by combining EGFR binding VH/VL domains and c-Met binding VH/VL domains that are publicly available and testing the resulting bispecific antibodies for their characteristics as described in U.S. Pat. No. 9,593,164.

Bispecific anti-EGFR/c-Met antibodies used in the methods of the disclosure may be generated for example using Fab arm exchange (or half molecule exchange) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy chain disulfide bonds in the hinge regions of the parental monospecific antibodies are reduced. The resulting free cysteines of one of the parental monospecific antibodies form an inter heavy-chain disulfide bond with cysteine residues of a second parental monospecific antibody molecule and simultaneously CH3 domains of the parental antibodies release and reform by dissociation-association. The CH3 domains of the Fab arms may be engineered to favor heterodimerization over homodimerization. The resulting product is a bispecific antibody having two Fab arms or half molecules which each bind a distinct epitope, i.e. an epitope on EGFR and an epitope on c-Met. For example, the bispecific antibodies of the invention may be generated using the technology described in Int. Pat. Publ. No. WO2011/131746. Mutations F405L in one heavy chain and K409R in the other heavy chain may be used in case of IgG1 antibodies. For IgG2 antibodies, a wild-type IgG2 and a IgG2 antibody with F405L and R409K substitutions may be used. For IgG4 antibodies, a wild-type IgG4 and a IgG4 antibody with F405L and R409K substitutions may be used. To generate bispecific antibodies, first monospecific bivalent antibody and the second monospecific bivalent antibody are engineered to have the aforementioned mutation in the Fc region, the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Bispecific anti-EGFR/c-Met antibodies used in the methods of the disclosure may also be generated using designs such as the Knob-in-Hole (Genentech), CrossMAbs (Roche) and the electrostatically-matched (Chugai, Amgen, NovoNordisk, Oncomed), the LUZ-Y (Genentech), the Strand Exchange Engineered Domain body (SEEDbody) (EMD Serono), and the Biclonic (Merus).

In the "knob-in-hole" strategy (see, e.g., Intl. Publ. No. WO 2006/028936) select amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

CrossMAb technology, in addition to utilizing the "knob-in-hole" strategy to promoter Fab arm exchange utilizes CH1/CL domain swaps in one half arm to ensure correct light chain pairing of the resulting bispecific antibody (see e.g. U.S. Pat. No. 8,242,247).

Other cross-over strategies may be used to generate full length bispecific antibodies of the invention by exchanging variable or constant, or both domains between the heavy chain and the light chain or within the heavy chain in the bispecific antibodies, either in one or both arms. These exchanges include for example VH-CH1 with VL-CL, VH with VL, CH3 with CL and CH3 with CH1 as described in Int. Patent Publ. Nos. WO2009/080254, WO2009/080251, WO2009/018386 and WO2009/080252.

Other strategies such as promoting heavy chain heterodimerization using electrostatic interactions by substituting positively charged residues at one CH3 surface and negatively charged residues at a second CH3 surface may be used, as described in US Patent Publ. No. US2010/0015133; US Patent Publ. No. US2009/0182127; US Patent Publ. No. US2010/028637 or US Patent Publ. No. US2011/0123532. In other strategies, heterodimerization may be promoted by following substitutions (expressed as modified positions in the first CH3 domain of the first heavy chain/modified position in the second CH3 domain of the second heavy chain): L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in U.S. Patent Publ. No. US2012/0149876 or U.S. Patent Publ. No. US2013/0195849.

SEEDbody technology may be utilized to generate bispecific antibodies of the invention. SEEDbodies have, in their constant domains, select IgG residues substituted with IgA residues to promote heterodimerization as described in U.S. Patent No. US20070287170.

Mutations are typically made at the DNA level to a molecule such as the constant domain of the antibody using standard methods.

An embodiment of the disclosure provides a method of treating a subject having a cancer, comprising administering to the subject a combination therapy, wherein the combination therapy comprises a therapeutically effective amount of an isolated bispecific anti-epidermal growth factor receptor (EGFR)/hepatocyte growth factor receptor (c-Met) antibody and a therapeutically effective amount of a compound of formula (I)

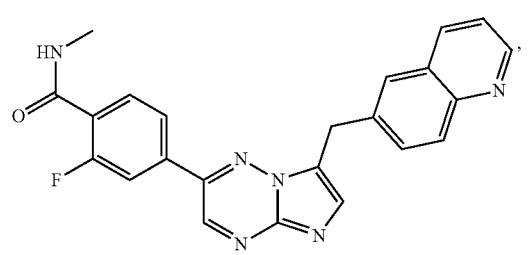

(I)

or solvate, hydrate, tautomer, or a pharmaceutically acceptable salt thereof.

An embodiment of the disclosure also provides a method of treating a subject having EGFR or c-Met expressing cancer, comprising administering to the subject a combination therapy, wherein the combination therapy comprises a therapeutically effective amount of an isolated bispecific anti-EGFR/c-Met antibody and a therapeutically effective amount of a compound of formula (I)

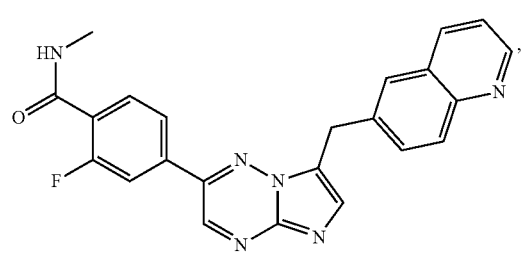

(I)

or solvate, hydrate, tautomer, or a pharmaceutically acceptable salt thereof.

An embodiment of the disclosure provides a pharmaceutical combination comprising a therapeutically effective amount of an isolated bispecific anti-epidermal growth factor receptor (EGFR)/hepatocyte growth factor receptor (c-Met) antibody and a therapeutically effective amount of a compound of formula (I)

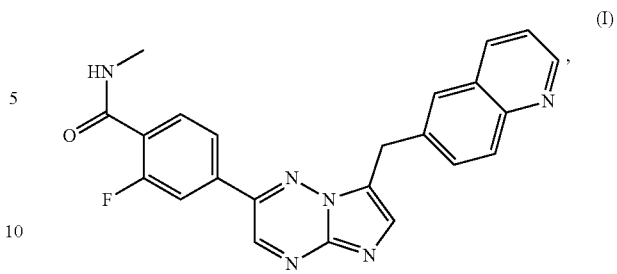

(I)

or solvate, hydrate, tautomer, or a pharmaceutically acceptable salt thereof, for use as a medicament, in particular for use as a medicament in a subject.

An embodiment of the disclosure provides a pharmaceutical combination comprising a therapeutically effective amount of an isolated bispecific anti-epidermal growth factor receptor (EGFR)/hepatocyte growth factor receptor (c-Met) antibody and a therapeutically effective amount of a compound of formula (I)

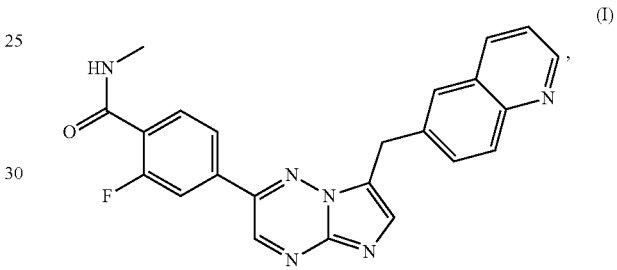

(I)

or solvate, hydrate, tautomer, or a pharmaceutically acceptable salt thereof, for use in the treatment of cancer, in particular for use in the treatment of cancer in a subject.

An embodiment of the disclosure provides a pharmaceutical combination comprising a therapeutically effective amount of an isolated bispecific anti-epidermal growth factor receptor (EGFR)/hepatocyte growth factor receptor (c-Met) antibody and a therapeutically effective amount of a compound of formula (I)

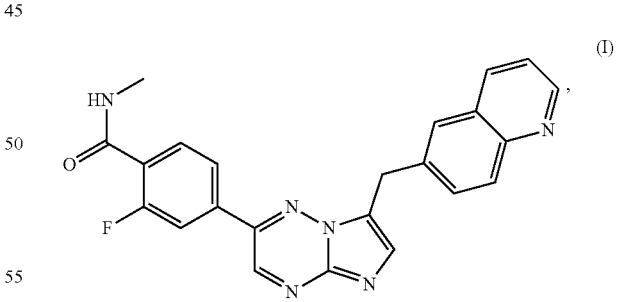

(I)

or solvate, hydrate, tautomer, or a pharmaceutically acceptable salt thereof, for use in the treatment of a subject having a cancer comprising a c-Met exon 14 skipping mutation.

An embodiment of the disclosure provides use of a combination comprising a therapeutically effective amount of an isolated bispecific anti-epidermal growth factor receptor (EGFR)/hepatocyte growth factor receptor (c-Met) antibody and a therapeutically effective amount of a compound of formula (I)

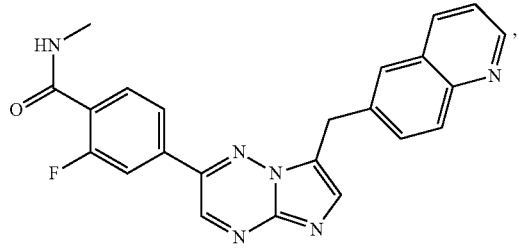
(I)

or solvate, hydrate, tautomer, or a pharmaceutically acceptable salt thereof, for the manufacture of a medicament for the treatment of cancer, in particular for the treatment of cancer in a subject.

An embodiment of the disclosure provides use of a combination comprising a therapeutically effective amount of an isolated bispecific anti-epidermal growth factor receptor (EGFR)/hepatocyte growth factor receptor (c-Met) antibody and a therapeutically effective amount of a compound of formula (I)

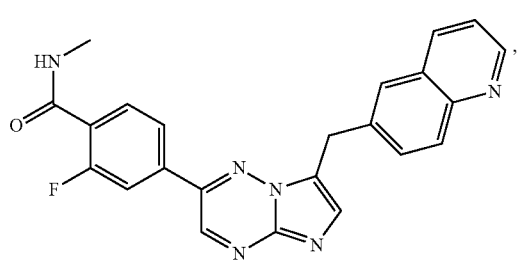
(I)

or solvate, hydrate, tautomer, or a pharmaceutically acceptable salt thereof, for the manufacture of a medicament for the treatment of a cancer, in particular for the treatment of a cancer comprising a c-Met exon 14 skipping mutation in a subject.

An embodiment of the disclosure provides a pharmaceutical combination comprising a therapeutically effective amount of an isolated bispecific anti-epidermal growth factor receptor (EGFR)/hepatocyte growth factor receptor (c-Met) antibody and a therapeutically effective amount of a compound of formula (I)

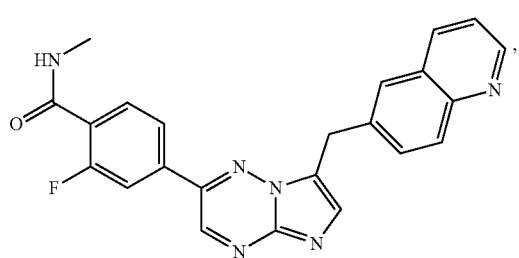
(I)

or solvate, hydrate, tautomer, or a pharmaceutically acceptable salt thereof.

An embodiment of the disclosure provides a product containing a therapeutically effective amount of an isolated bispecific anti-epidermal growth factor receptor (EGFR)/hepatocyte growth factor receptor (c-Met) antibody and a therapeutically effective amount of a compound of formula (I)

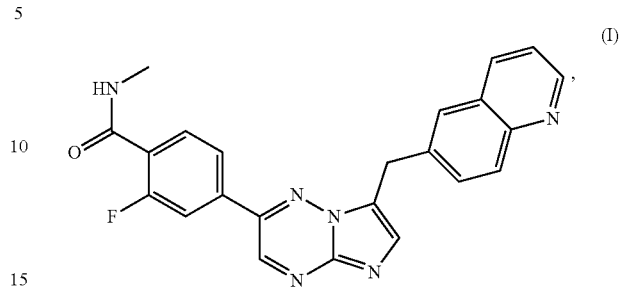
(I)

or solvate, hydrate, tautomer, or a pharmaceutically acceptable salt thereof, as a combined preparation for simultaneous, separate or sequential use in the treatment of cancer, in particular in the treatment of cancer in a subject.

An embodiment of the disclosure provides a product containing a therapeutically effective amount of an isolated bispecific anti-epidermal growth factor receptor (EGFR)/hepatocyte growth factor receptor (c-Met) antibody and a therapeutically effective amount of a compound of formula (I)

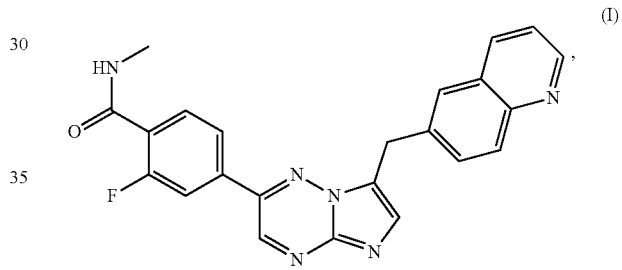
(I)

or solvate, hydrate, tautomer, or a pharmaceutically acceptable salt thereof, as a combined preparation for simultaneous, separate or sequential use in the treatment of cancer, in particular for the treatment of a cancer comprising a c-Met exon 14 skipping mutation in a subject.

An embodiment of the disclosure provides an isolated bispecific anti-epidermal growth factor receptor (EGFR)/hepatocyte growth factor receptor (c-Met) antibody, in particular a therapeutically effective amount of an isolated bispecific anti-epidermal growth factor receptor (EGFR)/hepatocyte growth factor receptor (c-Met) antibody, for use in combination with a compound of formula (I), in particular a therapeutically effective amount of a compound of formula (I),

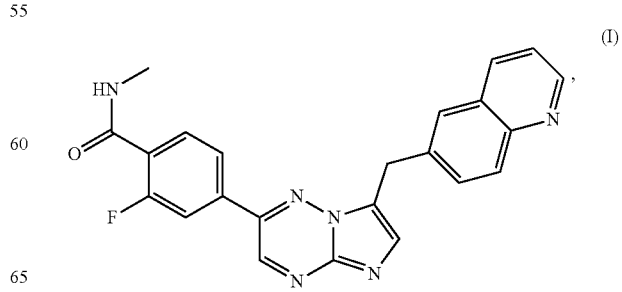
(I)

or solvate, hydrate, tautomer, or a pharmaceutically acceptable salt thereof, in the treatment of cancer, in particular in the treatment of cancer in a subject.

An embodiment of the disclosure provides an isolated bispecific anti-epidermal growth factor receptor (EGFR)/hepatocyte growth factor receptor (c-Met) antibody, in particular a therapeutically effective amount of an isolated bispecific anti-epidermal growth factor receptor (EGFR)/hepatocyte growth factor receptor (c-Met) antibody, for use in combination with a compound of formula (I), in particular a therapeutically effective amount of a compound of formula (I),

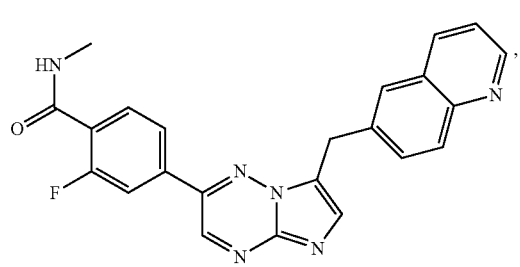

(I)

or solvate, hydrate, tautomer, or a pharmaceutically acceptable salt thereof, in the treatment of EGFR or c-Met expressing cancer, in particular in the treatment of a cancer comprising a c-Met exon 14 skipping mutation in a subject.

In each embodiment, the bispecific anti-EGFR/c-Met antibody and the capmatinib compound, or solvate, hydrate, tautomer, or a pharmaceutically acceptable salt thereof, may be administered at the same time (e.g., as part of the same pharmaceutical composition, or in separate pharmaceutical compositions) or at different times, as described herein.

Pharmaceutically acceptable salt forms include pharmaceutically acceptable acidic/anionic or basic/cationic salts. Pharmaceutically acceptable acidic/anionic salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, poly galacturonate, salicylate, stearate, subacetate, succinate, sulfate, hydrogensulfate, tannate, tartrate, teoclate, tosylate, and triethiodide salts. Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

A pharmaceutically acceptable acid salt is formed by reaction of the free base form of a compound of Formula (I) with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of Formula (I) can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

The free acid or free base forms of the compound of formula (I) may be prepared from the corresponding base addition salt or acid addition salt form, respectively. For example a compound of the invention in an acid addition salt form may be converted to the corresponding free base form by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

In some embodiments, the compound of formula (I) or solvate, hydrate, tautomer, or a pharmaceutically acceptable salt thereof is represented by a compound of formula (II)

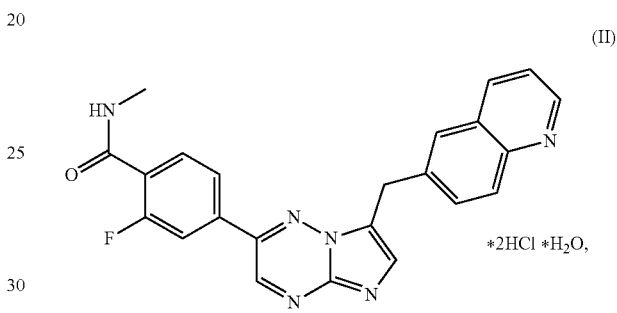

(II)

*2HCl *H$_2$O, a solvate, hydrate, or tautomer thereof.

In some embodiments, the cancer is c-Met expressing cancer.

In some embodiments, the cancer comprises a c-Met exon 14 skipping mutation.

Examplary c-Met exon 14 skipping mutations include mutations in the c-Met gene wherein at least a portion of exon 14 of c-Met is removed, or a c-Met transcript that is spliced to remove at least a portion of exon 14 of c-Met. The portion deleted may include a portion that encodes the negative regulation site Tyr 1003 in the juxtamembrane region of the c-Met protein. The exon 14 region of c-Met gene encompasses nucleotides 3284 to 3424 in the full-length nucleotide sequences of GenBank Accession No. NM_000245, or residues 964 to 1009 in the full-length c-Met amino acid sequences of GenBank Accession No. NP_000236. Various mutations at the DNA level can result in exon 14 skipping (see, e.g., Kong-Beltran et al. (2006) Cancer Res. 66; Dhanasekharan et al. (2014) Nature Communication 10:1038; Awad et al., J Clin Oncology 34: 721, 2016). Exon 14 of c-Met encodes 47 amino acids.

Methods for detecting c-Met mutations are well known.

In some embodiments, the bispecific anti-EGFR/c-Met antibody comprises a first domain that binds EGFR comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 and a second domain that binds c-Met comprising the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

In some embodiments, the first domain that binds EGFR comprises a heavy chain variable region (VH) of SEQ ID NO: 13 and a light chain variable region (VL) of SEQ ID NO: 14 and the second domain that binds c-Met comprises the VH of SEQ ID NO: 15 and the VL of SEQ ID NO: 16.

In some embodiments, the bispecific anti-EGFR/c-Met antibody is an IgG1 isotype. Some variation exists within the IgG1 constant domain (e.g. well-known allotypes), with variation at positions 214, 356, 358, 422, 431, 435 o 436 (residue numbering according to the EU numbering) (see e.g. IMGT Web resources; IMGT Repertoire (IG and TR); Proteins and alleles; allotypes). The bispecific anti-EGFR/c-Met antibody may be any IgG1 allotype, such as G1m17, G1m3, Glml, G1m2, G1m27 or Glm28.

In some embodiments, the bispecific anti-EGFR/c-Met antibody comprises the HC1 of SEQ ID NO: 17, the LC1 of SEQ ID NO: 18, the HC2 of SEQ ID NO: 19 and the LC2 of SEQ ID NO: 20.

In some embodiments, the subject has a newly diagnosed cancer.

In some embodiments, the subject has a newly diagnosed c-Met expressing cancer.

In some embodiments, the subject has a newly diagnosed cancer, comprising a c-Met exon 14 skipping mutation.

In some embodiments, the subject is tyrosine kinase inhibitor (TKI) treatment naïve.

In some embodiments, the subject is EGFR tyrosine kinase inhibitor (TKI) treatment naïve.

In some embodiments, the subject is resistant or relapsed to treatment with a EGFR TKI.

In some embodiments, the subject is resistant or has acquired resistance to treatment with a prior anti-cancer therapy.

In some embodiments, the prior anti-cancer therapy is chemotherapy, a targeted anti-cancer therapy or a kinase inhibitor.

In some embodiments, the TKI is an inhibitor of EGFR, c-Met, HER2, HER3, HER4, VEGFR or AXL.

In some embodiments, the TKI is erlotinib, gefitinib, lapatinib, vandetanib, afatinib, osimertinib, poziotinib, criotinib, cabozantinib, axitinib, lenvatinib, nintedanib, regorafenib, pazopanib, sorafenib or sunitinib.

In some embodiments, the cancer is a non-small cell lung cancer (NSCLC), an epithelial cell cancer, a breast cancer, an ovarian cancer, a lung cancer, a lung adenocarcinoma, a squamous ell lung cancer, a small cell lung cancer, a colorectal cancer, an anal cancer, a prostate cancer, a kidney cancer, a bladder cancer, a head and neck cancer, a pharynx cancer, a cancer of the nose, a pancreatic cancer, a skin cancer, an oral cancer, a cancer of the tongue, an esophageal cancer, a vaginal cancer, a cervical cancer, a cancer of the spleen, a testicular cancer, a gastric cancer, a cancer of the thymus, a colon cancer, a thyroid cancer, a liver cancer, a hepatocellular carcinoma (HCC) or sporadic or hereditary papillary renal cell carcinoma (PRCC). In some embodiments, the cancer is a metastatic cancer.

In some embodiments, the cancer is the NSCLC. In some embodiments, the cancer is the epithelial cell cancer. In some embodiments, the cancer is the breast cancer. In some embodiments, the cancer is the ovarian cancer. In some embodiments, the cancer is the lung cancer. In some embodiments, the cancer is the lung adenocarcinoma. In some embodiments, the cancer is the squamous cell lung cancer. In some embodiments, the cancer is the small cell lung cancer. In some embodiments, the cancer is the colorectal cancer. In some embodiments, the cancer is the anal cancer. In some embodiments, the cancer is the prostate cancer. In some embodiments, the cancer is the kidney cancer. In some embodiments, the cancer is the bladder cancer. In some embodiments, the cancer is the head and neck cancer. In some embodiments, the cancer is the pharynx cancer. In some embodiments, the cancer is the cancer of the nose. In some embodiments, the cancer is the pancreatic cancer. In some embodiments, the cancer is the skin cancer. In some embodiments, the cancer is the oral cancer. In some embodiments, the cancer is the cancer of the tongue. In some embodiments, the cancer is the esophageal cancer. In some embodiments, the cancer is the vaginal cancer. In some embodiments, the cancer is the cervical cancer. In some embodiments, the cancer is the cancer of the spleen. In some embodiments, the cancer is the testicular cancer. In some embodiments, the cancer is the gastric cancer. In some embodiments, the cancer is the cancer of the thymus. In some embodiments, the cancer is the colon cancer. In some embodiments, the cancer is the thyroid cancer. In some embodiments, the cancer is the liver cancer. In some embodiments, the cancer is the HCC. In some embodiments, the cancer is the PRCC.

In some embodiments, the NSCLC includes squamous cell carcinoma, adenocarcinoma, and large cell carcinoma. In some embodiments, cells of the NSCLC have an epithelial phenotype. In some embodiments, the NSCLC has acquired resistance to treatment with one or more EGFR inhibitors.

In some embodiments, the bispecific anti-EGFR/c-Met antibody is administered at a dose of between about 200 mg and about 2000 mg.

In some embodiments, the bispecific anti-EGFR/c-Met antibody is administered at a dose of between about 350 mg and about 1400 mg.

In some embodiments, the bispecific anti-EGFR/c-Met antibody is administered at a dose of about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, about 1000 mg, about 1010 mg, about 1020 mg, about 1030 mg, about 1040 mg, about 1050 mg, about 1060 mg, about 1070 mg, about 1080 mg, about 1090 mg, about 1100 mg, about 1110 mg, about 1120 mg, about 1130 mg, about 1140 mg, about 1150 mg, about 1160 mg, about 1170 mg, about 1180 mg, about 1190 mg, about 1200 mg, about 1210 mg, about 1220 mg, about 1230 mg, about 1240 mg, about 1250 mg, about 1260 mg, about 1270 mg, about 1280 mg, about 1290 mg, about 1300 mg, about 1310 mg, about 1320 mg, about 1330 mg, about 1340 mg, about 1350 mg, about 1360 mg, about 1370 mg, about 1380 mg, about 1390 mg, about 1400 mg, about 1410 mg, about 1420 mg, about 1430 mg, about 1440 mg, about 1450 mg, about 1460 mg, about 1470 mg, about 1480 mg, about 1490 mg, about 1500 mg, about 1510 mg, about 1520 mg, about 1530 mg, about 1540 mg, about 1550 mg, about 1560 mg, about 1570 mg, about 1580 mg, about 1590 mg, about 1600 mg, about 1610 mg, about 1620 mg, about 1630 mg, about 1640 mg, about 1650 mg, about 1660 mg, about 1670 mg, about 1680 mg, about 1690 mg, about 1700 mg, about 1710 mg, about 1720 mg, about 1730 mg, about 1740 mg, about 1750 mg, about 1760 mg, about 1770 mg, about 1780 mg, about 1790 mg, about 1800 mg, about 1810 mg, about 1820 mg, about 1830 mg, about 1840 mg, about 1850 mg, about 1860 mg, about 1870 mg, about 1880 mg, 1890 mg, about 1900 mg, about 1910 mg, about 1920 mg, about 1930 mg, about 1940 mg, about 1950 mg, about 1960 mg, about 1970 mg, about 9810 mg, about 1990 mg or about 2000 mg.

In some embodiments, the bispecific anti-EGFR/c-Met antibody is administered at a dose of about 350 mg, about 700 mg, about 1050 mg or about 1400 mg. In some embodiments, the bispecific anti-EGFR/c-Met antibody is administered at a dose of about 350 mg. In some embodiments, the bispecific anti-EGFR/c-Met antibody is administered at a dose of about 700 mg. In some embodiments, the bispecific anti-EGFR/c-Met antibody is administered at a dose of about 1050 mg. In some embodiments, the bispecific anti-EGFR/c-Met antibody is administered at a dose of about 1400 mg.

In some embodiments, the bispecific anti-EGFR/c-Met antibody is administered once a week.

In some embodiments, the bispecific anti-EGFR/c-Met antibody is administered once in two weeks.

In some embodiments, the compound of formula (I) or solvate, hydrate, tautomer, or a pharmaceutically acceptable salt thereof (e.g., the compound of formula (II), the capmatinib hydrochloride) is administered at a dose of between about 50 mg and about 500 mg. Doses of the compound of formula (I) or solvate, hydrate, tautomer, or a pharmaceutically acceptable salt thereof described herein refer to the amount of free base of the compound of formula (I) in the dose. For example, according to embodiments in which the dose comprises the hydrochloride of capmatinib (compound of formula (II)), the dose refers to the amount of capmatinib free base (compound of formula (I)).

In some embodiments, the compound of formula (I) or solvate, hydrate, tautomer, or a pharmaceutically acceptable salt thereof is administered at a dose of between about 50 mg and about 400 mg. In some embodiments, the compound of formula (I) or solvate, hydrate, tautomer, or a pharmaceutically acceptable salt thereof is administered at a dose of between about 100 mg and about 500 mg. In some embodiments, the compound of formula (I) or solvate, hydrate, tautomer, or a pharmaceutically acceptable salt thereof is administered at a dose of between about 200 mg and about 450 mg. In some embodiments, the compound of formula (I) or solvate, hydrate, tautomer, or a pharmaceutically acceptable salt thereof is administered at a dose of between about 250 mg and about 300 mg. In some embodiments, the compound of formula (I) or solvate, hydrate, tautomer, or a pharmaceutically acceptable salt thereof is administered at a dose of between about 100 mg and about 400 mg.

In some embodiments, the compound of formula (II) or solvate, hydrate, tautomer, or a pharmaceutically acceptable salt thereof is administered at a dose of between about 50 mg and about 400 mg. In some embodiments, the compound of formula (II) or solvate, hydrate, tautomer, or a pharmaceutically acceptable salt thereof is administered at a dose of between about 100 mg and about 500 mg. In some embodiments, the compound of formula (II) or solvate, hydrate, tautomer, or a pharmaceutically acceptable salt thereof is administered at a dose of between about 200 mg and about 450 mg. In some embodiments, the compound of formula (II) or solvate, hydrate, tautomer, or a pharmaceutically acceptable salt thereof is administered at a dose of between about 250 mg and about 300 mg. In some embodiments, the compound of formula (II) or solvate, hydrate, tautomer, or a pharmaceutically acceptable salt thereof is administered at a dose of between about 100 mg and about 400 mg.

In some embodiments, the compound of formula (I) or solvate, hydrate, tautomer, or a pharmaceutically acceptable salt thereof (e.g., the compound of formula (II), the capmatinib hydrochloride), is administered at a dose of at least about 50 mg, at least about 100 mg, at least about 150 mg, at least about 200 mg, at least about 250 mg, at least about 300 mg, at least about 350 mg, at least about 400 mg, at least about 450 mg, or at least about 500 mg.

In some embodiments, the compound of formula (I) or solvate, hydrate, tautomer, or a pharmaceutically acceptable salt thereof (e.g., the compound of formula (II), the capmatinib hydrochloride) is administered once a day.

In some embodiments, the compound of formula (I) or solvate, hydrate, tautomer, or a pharmaceutically acceptable salt thereof (e.g., the compound of formula (II), the capmatinib hydrochloride) is administered twice a day.

In some embodiments, the subject is further administered a third anti-cancer therapy.

In some embodiments, the third anti-cancer therapy is chemotherapy, a targeted anti-cancer therapy or a kinase inhibitor.

Anti-cancer therapies that may be administered in combination with the bispecific anti-EGFR/c-Met antibody and capmatinib in the methods of the disclosure include any one or more of the chemotherapeutic drugs or other anti-cancer therapeutics known to those of skill in the art. Chemotherapeutic agents are chemical compounds useful in the treatment of cancer and include growth inhibitory agents or other cytotoxic agents and include alkylating agents, anti-metabolites, anti-microtubule inhibitors, topoisomerase inhibitors, receptor tyrosine kinase inhibitors, angiogenesis inhibitors and the like. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-FU; folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; members of taxoid or taxane family, such as paclitaxel (TAXOL® docetaxel (TAXOTERE®) and analogues thereof; chlorambucil; gemcitabine; 6-thioguanine; mercaptopurine; methotrexate; platinum analogues such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; inhibitors of receptor tyrosine kinases and/or angiogenesis, including sorafenib (NEXAVAR®), sunitinib (SUTENT®), pazopanib (VOTRIENT™), toceranib (PALLADIA™), vandetanib (ZACTIMA™), cediranib (RECENTIN®), regorafenib (BAY 73-4506), axitinib (AG013736), lestaurtinib (CEP-701), erlotinib (TARCEVA®), gefitinib (IRESSA®), afatinib (BIBW 2992), lapatinib (TYKERB®), neratinib (HKI-272), and the like, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON®); and anti-androgens such as flutamide, nilutamide, bicalutamide, leuprolide, and goserelin; and pharmaceutically acceptable salts, acids or derivatives of any of the above. Other conventional cytotoxic chemical compounds as those disclosed in Wiemann et al., 1985, in Medical Oncology (Calabresi et aL, eds.), Chapter 10, McMillan Publishing, are also applicable to the methods of the present invention.

In some embodiments, the bispecific anti-EGFR/c-Met antibody is administered prior to administration of the compound of formula (I) or solvate, hydrate, tautomer or a pharmaceutically acceptable salt thereof.

In some embodiments, the bispecific anti-EGFR/c-Met antibody is administered prior to administration of the compound of formula (II) or solvate, hydrate, or tautomer thereof.

In some embodiments, the bispecific anti-EGFR/c-Met antibody is administered after administration of the compound of formula (I) or solvate, hydrate, tautomer or a pharmaceutically acceptable salt thereof.

In some embodiments, the bispecific anti-EGFR/c-Met antibody is administered after administration of the compound of formula (II) or solvate, hydrate, or tautomer thereof.

In some embodiments, the bispecific anti-EGFR/c-Met antibody is administered one or more times after administering the compound of formula (I) or solvate, hydrate, tautomer or a pharmaceutically acceptable salt thereof.

In some embodiments, the bispecific anti-EGFR/c-Met antibody is administered one or more times after administering the compound of formula (II) or solvate, hydrate, or tautomer thereof.

In some embodiments, the bispecific anti-EGFR/c-Met antibody is administered two, three, four, five, six, seven, eight, nine, ten or more times after administering the compound of formula (I) or solvate, hydrate, tautomer or a pharmaceutically acceptable salt thereof.

In some embodiments, the bispecific anti-EGFR/c-Met antibody is administered two, three, four, five, six, seven, eight, nine, ten or more times after administering the compound of formula (II) or solvate, hydrate, or tautomer thereof.

In some embodiments, the bispecific anti-EGFR/c-Met antibody is administered intermittently after administering the compound of formula (I) or solvate, hydrate, tautomer or a pharmaceutically acceptable salt thereof.

In some embodiments, the bispecific anti-EGFR/c-Met antibody is administered intermittently after administering the compound of formula (II) or solvate, hydrate, or tautomer thereof.

The length of time between administrations of the bispecific anti-EGFR/c-Met antibody and the compound of formula (I) or solvate, hydrate, tautomer or a pharmaceutically acceptable salt thereof, or formula (II) or solvate, hydrate, or tautomer thereof, or the third anti-cancer therapy may be a few minutes, such as about 1, 2, 5, 10, 30 or 60 minutes or several hours, such as about 2, 4, 6, 10, 12, 24 or 36 hours, or such as about 2, 4, 7, 14, 21, 28, 35, 42, 49, 56 days or more.

The bispecific anti-EGFR/c-Met antibody and the compound of formula (I) or solvate, hydrate, tautomer or a pharmaceutically acceptable salt thereof or the third anticancer agent may be administered as pharmaceutical compositions.

The bispecific anti-EGFR/c-Met antibody and the compound of formula (II) or solvate, hydrate, or tautomer thereof or the third anti-cancer agent may be administered as pharmaceutical compositions.

The bispecific anti-EGFR/c-Met antibody may be formulated into a pharmaceutical composition comprising the bispecific anti-EGFR/c-Met antibody and a pharmaceutically acceptable carrier. The pharmaceutically acceptable carrier may be one or more diluents, adjuvants, excipients, vehicles and the like. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used to formulate the bispecific anti-EGFR/c-Met antibody. These solutions are sterile and generally free of particulate matter. They may be sterilized by conventional, well-known sterilization techniques (e.g., filtration).

In some embodiments, the bispecific anti-EGFR/c-Met antibody is administered by an intravenous injection. In some embodiments, the bispecific anti-EGFR/c-Met antibody is administered by a subcutaneous injection.

In some embodiments, the compound of formula (I), or solvate, hydrate, tautomer or a pharmaceutically acceptable salt thereof, or the compound of formula (II) or solvate, hydrate, or tautomer thereof, is administered as an oral preparation, such as for example a solid oral preparation, such as a powder, capsule and tablet.

For solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated to modulate major site of absorption. For parenteral administration, the carrier may comprise sterile water and other excipients may be added to increase solubility or preservation. Injectable suspensions or solutions may also be prepared utilizing aqueous carriers along with appropriate additives. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The compositions may contain pharmaceutically acceptable auxiliary substances as required to approximate physiological conditions such as pH adjusting and buffering agents, stabilizing, thickening, lubricating and coloring agents, etc. The concentration of the bispecific anti-EGFR/c-Met antibody in the pharmaceutical formulation may vary, from less than about 0.5%, usually to at least about 1% to as much as 15%, 20%, 30%, 40% or 50% by weight and may be selected primarily based on required dose, fluid volumes, viscosities, etc., according to the particular mode of administration selected. Pharmaceutical compositions comprising solid forms may contain about 0.1 mg to about 2000 mg, such as about 1 mg, about 5 mg, about 10 mg, about 25 mg, about 50 mg, about 100 mg, about 150 mg, about 200 mg, about 300 mg, about 500 mg about 600 mg or about 1000 mg of active ingredient.

The mode of administration may be any suitable route that delivers the antibody to the host, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intratumoral, intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

The present invention will now be described with reference to the following specific, non-limiting examples.

EMBODIMENTS

The following clauses describe particular Embodiments of the present invention.

1) A method of treating a subject having cancer that is positive for a c-Met exon 14 skipping mutation, comprising administering a therapeutically effective amount of an isolated bispecific anti-epidermal growth factor receptor (EGFR)/hepatocyte growth factor receptor (c-Met) antibody to the subject having cancer that is positive for c-Met exon 14 skipping mutation.

2) A method of treating a subject having cancer with a bispecific anti-EGFR/c-Met antibody, comprising:
a) providing a biological sample from the subject;
b) determining presence or absence of a c-Met exon 14 skipping mutation in the sample;
c) administering or providing for administration the bispecific anti-EGFR/c-Met antibody to the subject determined to have c-Met exon 14 skipping mutation.

3) The method of Embodiment 1 or 2, wherein the bispecific anti-EGFR/c-Met antibody comprises a first domain that specifically binds EGFR and a second domain that specifically binds c-Met, wherein the first domain comprises a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 a second domain that binds c-Met, wherein the second domain comprises the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

4) The method of Embodiment 3, wherein the first domain that specifically binds EGFR comprises a heavy chain variable region (VH) of SEQ ID NO: 13 and a light chain variable region (VL) of SEQ ID NO: 14, and the second domain that specifically binds c-Met comprises the VH of SEQ ID NO: 15 and the VL of SEQ ID NO: 16.

5) The method of any one of Embodiments 1-4, wherein the bispecific anti-EGFR/c-Met antibody is an IgG1 isotype.

6) The method of any one of Embodiments 1-5, wherein the bispecific anti-EGFR/c-Met antibody comprises a first heavy chain (HC1) of SEQ ID NO: 17, a first light chain (LC1) of SEQ ID NO: 18, a second heavy chain (HC2) of SEQ ID NO: 19 and a second light chain (LC2) of SEQ ID NO: 20.

7) The method of any one of Embodiments 1-6, wherein the bispecific anti-EGFR/c-Met antibody comprises a biantennary glycan structure with a fucose content of about between 1% to about 15%.

8) The method of any one of Embodiments 1-7, wherein the subject is relapsed or resistant to treatment with one or more prior anti-cancer therapies.

9) The method of Embodiment 8, wherein the one or more prior anti-cancer therapies comprises one or more chemotherapeutic agents, checkpoint inhibitors, targeted anti-cancer therapies or kinase inhibitors, or any combination thereof.

10) The method of Embodiment 8, wherein the one or more prior anti-cancer thearpies comprises carboplatin, paclitaxel, gemcitabine, cisplatin, vinorelbine, docetaxel, palbociclib, crizotinib, PD-(L)1 axis inhibitor, an inhibitor of EGFR, an inhibitor of c-Met, an inhibitor of HER2, an inhibitor of HER3, an inhibitor of HER4, an inhibitor of VEGFR, an inhibitor of AXL, erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib, or any combination thereof.

11) The method of any one of Embodiments 1-7, wherein the subject is treatment naïve.

12) The method of any one of Embodiments 1-11, wherein cancer that is positive for c-Met exon 14 skipping mutation is positive for CDK4 amplification, EGFR amplification, KRAS amplification, MDM2 amplification, TERT amplification, NF1 R2450*; RAD50 L597Vfs*5, MET c.3082+3A>G, EGFR, wild-type EGFR, an EGFR activating mutation, increased levels of circulating HGF, c-MET amplification or a mutant KRAS, or any combination thereof.

13) The method of Embodiment 12, wherein the EGFR activating mutation comprises L718Q, G719A, G719X (X being any amino acid), L861X (X being any amino acid), L858R, E746K, L747S, E749Q, A750P, A755V, V765M, C797S, L858P or T790M substitution, deletion of E746-A750, deletion of R748-P753, insertion of Ala (A) between M766 and A767, insertion of Ser, Val and Ala (SVA) between S768 and V769, insertion of Asn and Ser (NS) between P772 and H773, insertion of one or more amino acids between D761 and E762, A763 and Y764, Y764 and Y765, M766 and A767, A767 and V768, S768 and V769, V769 and D770, D770 and N771, N771 and P772, P772 and H773, H773 and V774, V774 and C775, one or more deletions in EGFR exon 20, or one or more insertions in EGFR exon 20, or any combination thereof.

14) The method of Embodiment 12, wherein the mutant KRAS comprises a G12V, G12C, G12A or G12D substitution, or any combination thereof.

15) The method of any one of Embodiments 1-14, wherein the cancer is lung cancer, gastric cancer, colorectal cancer, brain cancer, cancer derived from epithelial cells, breast cancer, ovarian cancer, colorectal cancer, anal cancer, prostate cancer, kidney cancer, bladder cancer, head and neck cancer, pharynx cancer, cancer of the nose, pancreatic cancer, skin cancer, oral cancer, cancer of the tongue, esophageal cancer, vaginal cancer, cervical cancer, cancer of the spleen, testicular cancer, gastric cancer, cancer of the thymus, colon cancer, thyroid cancer, liver cancer, hepatocellular carcinoma (HCC) or sporadic or hereditary papillary renal cell carcinoma (PRCC), or any combination thereof.

16) The method of Embodiment 15, wherein lung cancer is non-small cell lung cancer (NSCLC), small cell lung cancer (SCLC) or lung adenocarcinoma, pulmonary sarcomatoid carcinoma or any combination thereof.

17) The method of any one of Embodiments 1-16, comprising further administering one or more anti-cancer therapies to the subject.

18) The method of Embodiment 17, wherein the one or more anti-cancer therapies comprises chemotherapy, radiation therapy, surgery, a targeted anti-cancer therapy or a kinase inhibitor, or any combination thereof.

19) The method of Embodiment 18, wherein the kinase inhibitor is an inhibitor of EGFR, an inhibitor of c-Met, an inhibitor of HER2, an inhibitor of HER3, an inhibitor of HER4, an inhibitor of VEGFR or an inhibitor of AXL.

20) The method of Embodiment 19, wherein the kinase inhibitor is erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib.

21) The method of any one of Embodiments 1-20, wherein the c-Met exon 14 skipping mutation is a de novo mutation.

22) The method of any one of Embodiments 1-21, wherein the c-Met exon 14 skipping mutation is an acquired mutation.

23) The method of any one of Embodiments 1-22, wherein the bispecific anti-EGFR/c-Met antibody is administered at a dose of between about 140 mg to about 1750 mg.

24) The method of any one of Embodiments 1-23, wherein the bispecific anti-EGFR/c-Met antibody is administered at a dose of about 700 mg, about 750 mg, about 800 mg, about 850 mg, 900 mg, 950 mg, 1000 mg, 1050 mg, 1100 mg, 1150 mg, 1200 mg, 1250 mg, 1300 mg, 1350 mg or 1400 mg.

25) The method of any one of Embodiments 1-24, wherein the bispecific anti-EGFR/c-Met antibody is administered twice a week, once a week, once in two weeks, once in three weeks or once in four weeks.

26) A method of treating a subject having cancer that is positive for a c-Met exon 14 skipping mutation, comprising administering to the subject a combination therapy, wherein the combination therapy comprises a therapeutically effective amount of an isolated bispecific anti-epidermal growth factor receptor (EGFR)/hepatocyte growth factor receptor (c-Met) antibody and a therapeutically effective amount of a compound of formula (II)

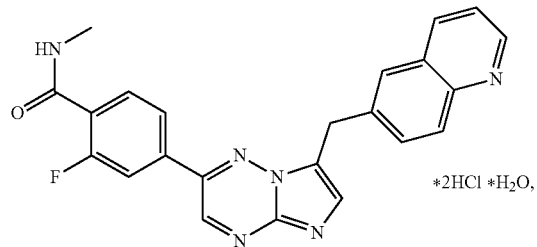

or solvate, hydrate, tautomer, or a pharmaceutically acceptable salt thereof.

27) The method of Embodiment 26, wherein the bispecific anti-EGFR/c-Met antibody comprises a first domain that binds EGFR comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 and a second domain that binds c-Met comprising the HCDR1 of SEQ ID NO: 7, the HCDR2 of SEQ ID NO: 8, the HCDR3 of SEQ ID NO: 9, the LCDR1 of SEQ ID NO: 10, the LCDR2 of SEQ ID NO: 11 and the LCDR3 of SEQ ID NO: 12.

28) The method of Embodiment 27, wherein the first domain that binds EGFR comprises a heavy chain variable region (VH) of SEQ ID NO: 13 and a light chain variable region (VL) of SEQ ID NO: 14 and the second domain that binds c-Met comprises the VH of SEQ ID NO: 15 and the VL of SEQ ID NO: 16.

29) The method of any one of Embodiments 26-28, wherein the bispecific anti-EGFR/c-Met antibody is an IgG1 isotype.

30) The method of any one of Embodiments 26-29, wherein the bispecific anti-EGFR/c-Met antibody comprises a first heavy chain (HC1) of SEQ ID NO: 17, a first light chain (LC1) of SEQ ID NO: 18, a second heavy chain (HC2) of SEQ ID NO: 19 and a second light chain (LC2) of SEQ ID NO: 20.

31) The method of any one of Embodiments 26-30, wherein the bispecific anti-EGFR/c-Met antibody has a biantennary glycan structure with a fucose content of between about 1% to about 15%.

32) The method of any one of Embodiments 26-31, wherein the compound of formula (II) or solvate, hydrate, tautomer, or a pharmaceutically acceptable salt thereof is 2-Fluoro-N-methyl-4-[7-(quinolin-6-ylmethyl)imidazo[1,2-b][1,2,4]triazin-2-yl]benzamide-hydrogen chloride-water (1/2/1).

33) The method of any one of Embodiments 26-32, wherein the subject is relapsed or resistant to treatment with one or more prior anti-cancer therapies.

34) The method of Embodiment 33, wherein the one or more prior anti-cancer therapies comprises one or more chemotherapeutic agents, checkpoint inhibitors, targeted anti-cancer therapies or kinase inhibitors, or any combination thereof.

35) The method of Embodiment 33, wherein the one or more prior anti-cancer thearpies comprises carboplatin, paclitaxel, gemcitabine, cisplatin, vinorelbine, docetaxel, palbociclib, crizotinib, PD-(L)1 axis inhibitor, an inhibitor of EGFR, an inhibitor of c-Met, an inhibitor of HER2, an inhibitor of HER3, an inhibitor of HER4, an inhibitor of VEGFR, an inhibitor of AXL, erlotinib, gefitinib, lapatinib, vandetanib, afatinib, osimertinib, lazertinib, poziotinib, criotinib, cabozantinib, axitinib, lenvatinib, nintedanib, regorafenib, pazopanib, sorafenib or sunitinib, or any combination thereof.

36) The method of any one of Embodiments 26-32, wherein the subject is treatment naïve.

37) The method of any one of Embodiments 26-36, wherein cancer that is positive for c-Met exon 14 skipping mutation is positive for CDK4 amplification, EGFR amplification, KRAS amplification, MDM2 amplification, TERT amplification, NF1 R2450*; RAD50 L597Vfs*5, MET c.3082+3A>G, EGFR, wild-type EGFR, an EGFR activating mutation, increased levels of circulating HGF, c-MET amplification or a mutant KRAS, or any combination thereof.

38) The method of Embodiment 37, wherein the EGFR activating mutation comprises L718Q, G719A, G719X (X being any amino acid), L861X (X being any amino acid), L858R, E746K, L747S, E749Q, A750P, A755V, V765M, C797S, L858P or T790M substitution, deletion of E746-A750, deletion of R748-P753, insertion of Ala (A) between M766 and A767, insertion of Ser, Val and Ala (SVA) between S768 and V769, insertion of Asn and Ser (NS) between P772 and H773, insertion of one or more amino acids between D761 and E762, A763 and Y764, Y764 and Y765, M766 and A767, A767 and V768, S768 and V769, V769 and D770, D770 and N771, N771 and P772, P772 and H773, H773 and V774, V774 and C775, one or more deletions in EGFR exon 20, or one or more insertions in EGFR exon 20, or any combination thereof.

39) The method of Embodiment 37, wherein the mutant KRAS comprises a G12V, G12C, G12A or G12D substitution, or any combination thereof.

40) The method of any one of Embodiments 26-39, wherein the cancer is lung cancer, gastric cancer, colorectal cancer, brain cancer, cancer derived from epithelial cells, breast cancer, ovarian cancer, colorectal cancer, anal cancer, prostate cancer, kidney cancer, bladder cancer, head and neck cancer, pharynx cancer, cancer of the nose, pancreatic cancer, skin cancer, oral cancer, cancer of the tongue, esophageal cancer, vaginal cancer, cervical cancer, cancer of the spleen, testicular cancer, gastric cancer, cancer of the thymus, colon cancer, thyroid cancer, liver cancer, hepatocellular carcinoma (HCC) or sporadic or hereditary papillary renal cell carcinoma (PRCC), or any combination thereof.

41) The method of Embodiment 40, wherein lung cancer is non-small cell lung cancer (NSCLC), small cell lung cancer (SCLC) or lung adenocarcinoma, pulmonary sarcomatoid carcinoma or any combination thereof.

42) The method of any one of Embodiments 26-41, comprising further administering one or more anti-cancer therapies to the subject.

43) The method of Embodiment 42, wherein the one or more anti-cancer therapies comprises chemotherapy, radiation therapy, surgery, a targeted anti-cancer therapy or a kinase inhibitor, or any combination thereof.

44) The method of Embodiment 43, wherein the kinase inhibitor is an inhibitor of EGFR, an inhibitor of c-Met, an inhibitor of HER2, an inhibitor of HER3, an inhibitor of HER4, an inhibitor of VEGFR or an inhibitor of AXL.

45) The method of Embodiment 44, wherein the kinase inhibitor is erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib or sunitinib.

46) The method of any one of Embodiments 26-45, wherein the c-Met exon 14 skipping mutation is a de novo mutation.

47) The method of any one of Embodiments 26-46, wherein the c-Met exon 14 skipping mutation is an acquired mutation.

48) The method of any one of Embodiments 26-47, wherein the bispecific anti-EGFR/c-Met antibody is administered at a dose of between about 140 mg to about 1750 mg.

49) The method of any one of Embodiments 26-48, wherein the bispecific anti-EGFR/c-Met antibody is administered at a dose of about 700 mg, about 750 mg, about 800 mg, about 850 mg, 900 mg, 950 mg, 1000 mg, 1050 mg, 1100 mg, 1150 mg, 1200 mg, 1250 mg, 1300 mg, 1350 mg or 1400 mg.

50) The method of any one of Embodiments 26-49, wherein the bispecific anti-EGFR/c-Met antibody is administered twice a week, once a week, once in two weeks, once in three weeks or once in four weeks.

Example 1. JNJ-372 was Effective in c-Met Driven PDX Models

Efficacy of JNJ-372 was tested in a PDX model harboring c-Met exon 14 skipping mutation. As comparator, erlotinib and cetuximab were used. For these experiments, JNJ-372 was expressed in wild-type CHO cells and hence exhibited fucose content characteristics of a wild-type CHO cell.

Tumor fragments from stock mice inoculated with selected primary human NSCLC tissues were harvested and used for inoculation into BALB/c nude mice. Each mouse was inoculated subcutaneously at the right flank with primary human NSCLC model (LU2503) fragment (passage 5, 2-4 mm in diameter) for tumor development. The treatment was started when the average tumor size reached about 151.5 mm$^3$. Mice were allocated randomly into four experimental groups according to their tumor sizes. Each group consisted of 10 mice, 5 mice per cage. The day was denoted as day 0. The test articles were administrated to the tumor-bearing mice from day 0 through day 25, according to predetermined regimen shown in Table 1.

TABLE 1

| Group | N | Treatment | Dose (mg/kg) | Dosing route | Schedule |
|---|---|---|---|---|---|
| 1 | 10 | PBS | — | ip | Day 1, 4/wk × 4 |
| 2 | 10 | Erlotinib | 50 | po | QD (5 d on, 2 d off) × 4 wks |
| 3 | 10 | Cetuximab | 10 | ip | Day 1, 4/wk × 4 |
| 4 | 10 | JNJ-372 | 10 | ip | Day 1, 4/wk × 4 | ip: intraperitoneal; po: oral administration

The major endpoint was to see if the tumor growth could be delayed or tumor bearing mice could be cured. Tumor size was measured twice weekly in two dimensions using a caliper, and the volume was expressed in mm$^3$ using the formula: V=0.5 a×b$^2$ where a and b were the long and short diameters of the tumor, respectively. The tumor size was then used for calculations of both T-C and T/C values. T-C was calculated with T as the time (in days) required for the mean tumor size of the treatment group to reach a predetermined size (e.g., 1000 mm$^3$), and C was the time (in days) for the mean tumor size of the control group to reach the same size. The T/C value (in percent) was an indication of anti-tumor effectiveness; T and C were the mean volume of the treated and control groups, respectively, on a given day. The study was terminated when the scheduled dosing was completed and the mean tumor burden in the vehicle treated control group reaches a value of 2000 mm$^3$. The differences between the mean values of tumor size for comparing groups were analyzed for significance using SPSS software. P<0.05 was considered to be statistically significant.

Tumor sizes (expressed as mean±SEM) within the treatment groups at different time points during treatment are shown in Table 2. Tumor growth inhibition is summarized in Table 3. The T-C was calculated as tumors reached the predetermined size (1000 mm$^3$). FIG. 1 shows the tumor volume over time.

TABLE 2

| | Tumor volume (mm$^3$) | | | |
|---|---|---|---|---|
| Days | PBS | Erlotinib (50 mg/kg, 5 d on 2 d off) | Cetuximab (10 mg/kg, BIW × 4) | JNJ-372 (10 mg/kg, BIW × 4) |
|---|---|---|---|---|
| 0 | 153.06 ± 72.01 | 145.51 ± 79.04 | 161.49 ± 65.31 | 146.09 ± 40.62 |
| 3 | 283.26 ± 105.3 | 300.92 ± 126.54 | 277.61 ± 122.14 | 88.1 ± 31.92 |
| 7 | 497.39 ± 165.91 | 445.11 ± 204.59 | 379.81 ± 161.78 | 46.93 ± 33.78 |
| 10 | 683.77 ± 242.47 | 623.87 ± 267.31 | 501.39 ± 201.06 | 33.91 ± 23.17 |
| 14 | 900.76 ± 401.66 | 960.92 ± 607.83 | 534.57 ± 214.89 | 33.65 ± 23.85 |
| 17 | 1248.59 ± 677.29 | 1256.11 ± 874.73 | 683.98 ± 288.02 | 36.14 ± 26.93 |
| 21 | 1574.54 ± 1072.1 | 1418.86 ± 599.79 | 973.67 ± 540.43 | 41.71 ± 38.89 |
| 27 | 2160.5 ± 1586.17 | 1790.79 ± 871.41 | 1378.12 ± 798.39 | 48.35 ± 55.86 |

TABLE 3

| Treatment | Tumor Size (mm$^3$)[a] on day 0 of treatment | Tumor Size (mm$^3$)[a] on day 27 of treatment | T-C[b] (day) | T/C (%) | P value[c] |
|---|---|---|---|---|---|
| PBS | 153.06 ± 72.01 | 2160.5 ± 1586.17 | — | — | — |
| Erlotinib (50 mg/kg) | 145.51 ± 79.04 | 1790.79 ± 871.41 | 0 | 82.9 | 0.837 |
| Cetuximab (10 mg/kg) | 161.49 ± 65.31 | 1378.12 ± 798.39 | 10 | 63.8 | 0.305 |
| JNJ-372 (10 mg/kg) | 138.42 ± 66.33 | 48.35 ± 55.86 | NA[d] | 2.2 | <0.0001** |

[a]Mean ± SEM;
[b]Predetermined size: 1000 mm$^3$
[c]compared with the vehicle by one-way ANOVA and Turkey multiple comparison test.
[d]T-C value was not available due to the shrinkage of tumors In group 2 (Erlotinib 50 mg/kg, 5d on 2d off), group 3 (Cetuximab 10 mg/kg, BIW×4) and group 4 (JNJ-372 10 mg/kg, BIW×4) the body weight change on day 27 of treatment was −8%, 3.6%, and 6.6% respectively (data not shown).

The mean tumor size of the vehicle treated mice reached 2160.5 mm$^3$ on day 27 and this study was terminated on day 28. JNJ-372 treatment with 10 mg/kg, BIW×4 produced significant anti-tumor response compared with vehicle treatment (P<0.0001). JNJ-372 treatment at 10 mg/kg, BIW×4, produced a mean tumor size of 48.35 mm$^3$ and its T-C could not be calculated because of the shrinkage of tumors. In summary, JNJ-372 at 10 mg/kg, BIW×4 produced significant anti-tumor activity against the primary human NSCLC tumor xenograft model LU2503 in this study.

Example 2. JNJ-372 Suppressed Tumor Growth in Patients Harboring c-Met Exon 14 Skipping Mutations The potential clinical benefit of JNJ-372 in NSCLC with MET driver alterations was evaluated. JNJ-372 used in clinical studies was produced in a cell line resulting in antibody fucose content of below 15%.

Eligible patients with metastatic NSCLC received escalating doses (from 140 mg to 1750 mg) of JNJ-372 in Part 1 or at the RP2D in Part 2 expansion cohorts. JNJ-372 was administered intravenously (IV) in 28-day cycles on days 1, 2, 8, 15 and 22 of cycle 1 and days 1 and 15 during subsequent cycles. Disease response was evaluated every 6 weeks by investigator assessment according to RECIST v. 1.1 criteria.

Figure 2:
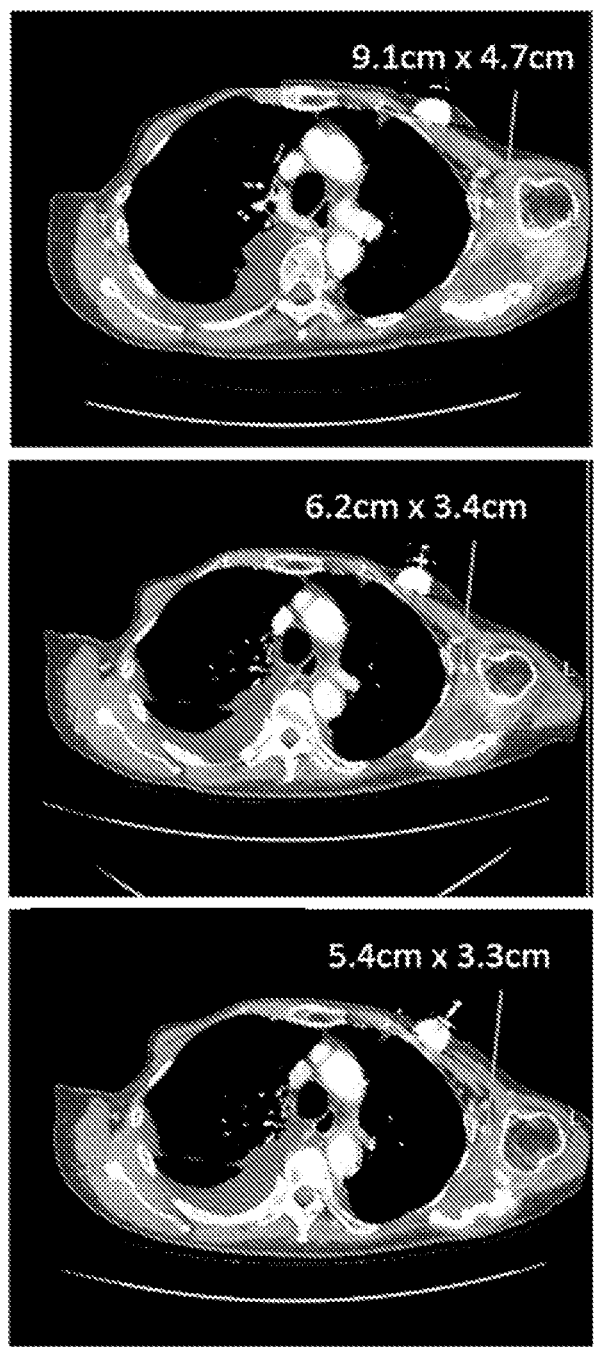
FIG. 2 shows a CT scan at baseline (top panel), at 6 weeks of treatment (middle panel) and at 12 weeks of treatment (bottom panel) with 1050 mg JNJ-372. Tumor size is indicated in each panel.

Patient 1: A 76-year-old with heavily pre-treated metastatic adenosquamous NSCLC with a MET exon 14 skipping mutation was first diagnosed with metastatic disease. Following multiple chemotherapy regimens (carboplatin and paclitaxel, carboplatin and gemcitabine, cisplatin and vinorelbine, docetaxel), local radiation and nivolumab, next generation sequencing (NGS) revealed MET ex14 deletion; NF1 R2450; CDK4 amplification; MDM2 amplification; EPHB1 amplification; FRS2 amplification; RAD50 N598fs*4. The patient received palbociclib on trial without response followed by crizotinib for 11 months with stable disease as best response. Post crizotinib biopsy of the left axillary lymph node revealed metastatic lung adenosquamous carcinoma and next-generation sequencing (HopeSeq) demonstrated CDK4 amplification; EGFR amplification; KRAS amplification; MET ex14 deletion, MET c.3082+ 3A>G; MDM2 amplification; NF1 R2450*; RAD50 L597Vfs*5; TERT amplification; PD-L1 5%. This suggested EGFR and KRAS amplification as potential mechanisms of resistance to crizotinib as have been previously reported. The patient started JNJ-372 at 1050 mg in the Phase 1 portion of the study. Restaging CT scan at 6 weeks showed partial response (PR) with 32% decrease in the tumor compared with the baseline CT scan (9.1 to 6.2 cm). CT scan at 12 weeks confirmed continued PR at 41% reduction of the tumor (5.4 cm). At the last visit, the patient was tolerating the treatment well with mild toxicity through 4 cycles and remained on the 1050 mg dose. FIG. 2 shows a CT scan that indicated partial response at 6 weeks and 12 weeks post treatment.

Reported herein a first case of primary MET ex14 deletion NSCLC with resistance to crizotinib to experience confirmed partial response to JNJ-372 in the Phase 1 study after multiple lines of therapy. This suggests a potential new therapeutic option for patients with MET ex14 deletion.

Example 3. JNJ-372 was Efficacious in the Inhibition of c-Met Driven NSCLC PDX Tumor Growth in LU2503

The efficacy of JNJ-372 and a small molecule c-MET inhibitor capmatinib (Selleck, 52788) was evaluated in a NSCLC PDX model LU2503 harboring c-Met exon 14 skipping mutation. LU2503 PDX model was established by CrownBio and described in Yang M, Shan B, Li Q, Song X, Cai J, Deng J, et al. Overcoming erlotinib resistance with tailored treatment regimen in patient-derived xenografts from naive Asian NSCLC patients. International journal of cancer. 2013; 132:E74-84. LU2503 tumor fragments from stock tumor bearing mice (passage R17P12) were harvested and used for inoculation into BALB/c nude mice. Each mouse was inoculated subcutaneously in the right rear flank with PDX LU2503 tumor fragments (approximately 2-3 mm in diameter) for tumor development.

After establishment of palpable lesions, the tumor growth was measured twice weekly. Once the tumor volume reached approximately 200 mm3, animals were randomly allocated to relevant study groups with 8 mice each group. The randomization was performed according to the tumor size of each group and the day of randomization was denoted as day 0. The treatments were started on the same day of randomization per study design in Table 4.

TABLE 4

Figure 3A:
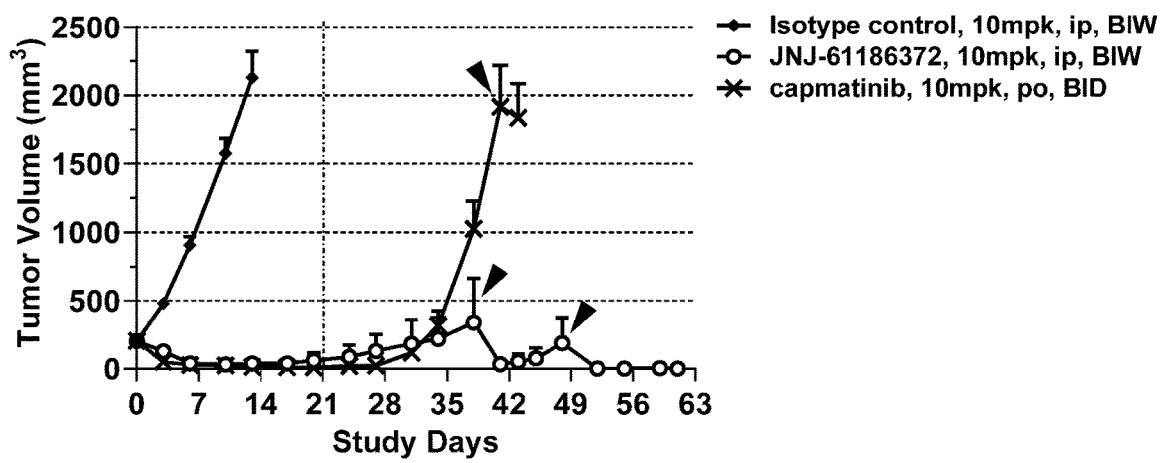
FIGS. 3A-3B show mean tumor volumes (FIG. 3A) and mean body weights (FIG. 3B) in mice with tumors harboring c-Met exon 14 skipping mutation (LU2503), treated with JNJ-61186372 (JNJ-372), capmatinib, or Isotype control; arrowheads indicate individual animal termination due to tumor size; vertical dashed line represents end of dosing.

| Group | N | Treatment | Dosing (mg/kg) | Dosing Route | Dosing Schedule |
|---|---|---|---|---|---|
| 1 | 8 | Isotype Control | 10 | i.p. | BIW (Day 0, 3 each week) × 2 weeks |
| 2 | 8 | JNJ-61186372 | 10 | i.p. | BIW (Day 0, 3 each week) × 3 weeks Then keep observation (till Day 61) |
| 3 | 8 | capmatinib | 10 | p.o. | BID × 3 weeks Then keep observation (till Day 43) | i.p.: intraperitoneal; p.o.: oral administration; BIW: bi-weekly; BID: twice a day The study endpoints were to compare the tumor growth in each group at the end of treatments and the subsequent tumor outgrowth after dosing stopped. The tumor size was measured twice weekly in two dimensions using a caliper, and the volume was expressed in mm$^3$ using the formula: V=(L×W×W)/2, where V was tumor volume, L was tumor length (the longest tumor dimension) and W was tumor width (the longest tumor dimension perpendicular to L). Tumor sizes (expressed as mean+SEM) within the treatment groups at different time points during treatment are shown in Table 5 and the tumor growth curves over time are shown in FIG. 3A.

TABLE 5

| | Tumor Volume[a] (mm³) | | |
|---|---|---|---|
| Study Days | Isotype Control (10 mg/kg, BIW) 2 weeks | JNJ-61186372 (10 mg/kg, BIW) 3 weeks | Capmatinib (10 mg/kg, BID) 3 weeks |
| 0 | 202.01 ± 16.05 | 202.45 ± 19.68 | 202.15 ± 18.52 |
| 3 | 477.94 ± 45.45 | 128.88 ± 27.33 | 50.62 ± 6.60 |
| 6 | 904.64 ± 64.00 | 39.09 ± 19.01 | 27.34 ± 6.51 |
| 10 | 1576.12 ± 111.22 | 31.43 ± 26.79 | 23.95 ± 7.35 |
| 13 | 2127.17 ± 195.64 | 39.97 ± 32.01 | 13.92 ± 4.73 |
| 17 | | 39.94 ± 34.86 | 10.17 ± 4.30 |
| 20 | | 59.99 ± 54.92 | 10.94 ± 3.88 |
| 24 | | 86.77 ± 86.77 | 19.28 ± 4.97 |
| 27 | | 130.09 ± 122.34 | 22.14 ± 7.17 |
| 31 | | 184.26 ± 173.62 | 116.24 ± 25.06 |
| 34 | | 217.73 ± 207.39 | 316.12 ± 61.34 |
| 38 | | 340.36 ± 324.37 | 1025.51 ± 204.62 |
| 41 | | 33.55 ± 33.55 | 1916.81 ± 302.93 |
| 43 | | 53.73 ± 53.73 | 1835.58 ± 250.86 |
| 45 | | 76.66 ± 76.66 | |
| 48 | | 187.88 ± 187.88 | |
| 52 | | 0.00 ± 0.00 | |
| 55 | | 0.00 ± 0.00 | |
| 59 | | 5.17 ± 5.17 | |
| 61 | | 0.00 ± 0.00 | |

[a]Data represent Mean tumor volume ± Standard Error of Mean (SEM).

Figure 3B:
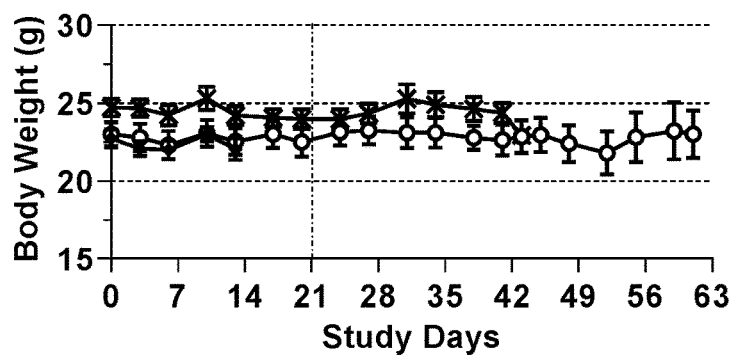

Tumor growth inhibition (TGI %) was an indication of antitumor activity and calculated as %ΔInhibition=100× ((C–C0)–(T–T0))/(C–C0), T and C were the mean tumor volume of the treated and control groups, respectively on the day when mean tumor volume (TV) of vehicle group reached the humane endpoints (>2000 mm3, day 13). Tumor growth inhibition is summarized in Table 6. To compare the mean tumor volumes of treatment groups with vehicle control group, we first used Bartlett's test to check the assumption of homogeneity of variance across all groups. The p-value of Bartlett's test was <0.05, we ran Kruskal-Wallis test for overall equality of medians among all groups (<0.05). Then we further performed post hoc testing by running Conover's non-parametric test with single-step p-value adjustment (P<0.05 was considered to be statistically significant). The body weight changes were monitored and are shown in FIG. 3B.

As shown in FIG. 3A, both JNJ-372 at 10 mg/kg, BIW×3 and capmatinib at 10 mg/kg, BID×21 produced significant anti-tumor activity (108.44% and 109.78% TGI respectively) against the primary LU2503 human NSCLC tumor xenograft in this study. During the dose-free monitoring phase after day 21, all 8 capmatinib-treated animals showed faster tumor regrowth comparing to JNJ-372-treated animals (6 out of 8 animals showed no measurable tumors till study end).

Example 4. JNJ-372 in Combination with MET-TKI (Capmatinib) Showed Deeper and More Durable Tumor Inhibition in LU2503

A follow up study in LU2503 included the combination treatment of JNJ-372 and capmatinib to see whether there is any additional benefit when JNJ-372 is combined with MET-TKI. Tumor fragments from stock mice (passage R18P2) were subcutaneously implanted into the right rear flank of BALB/c nude mice for tumor propagation.

Figure 4A:
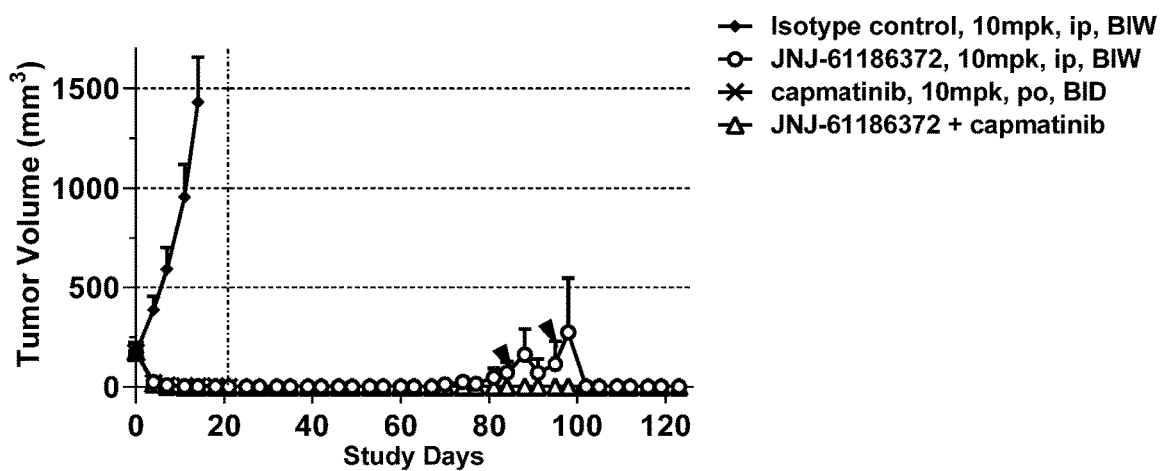
FIGS. 4A-4B show mean tumor volumes (FIG. 4A) and mean body weights (FIG. 4B) in mice with tumors harboring c-Met exon 14 skipping mutation (LU2503), treated with JNJ-61186372 (JNJ-372), capmatinib, JNJ-61186372 and capmatinib, or Isotype control; arrowheads indicate individual animal termination due to tumor size; vertical dashed line represents end of dosing.
Figure 4B:
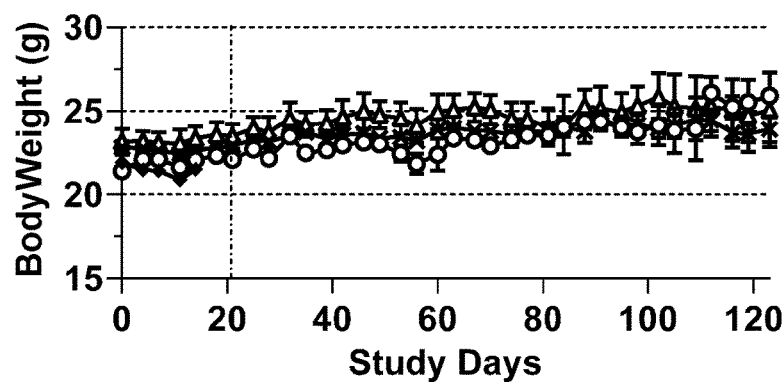

Treatments were started in the efficacy study according to the following design (Table 7) when the average tumor size reached about 150-200 mm³. Animals were randomly allocated into four experimental groups according to their tumor sizes with 8 mice each group. The tumor size was measured and body weight monitored twice per week asdescribed in Example 3. Tumor sizes (expressed as mean+SEM) within the treatment groups at different time points during treatment are shown in Table 8, the tumor growth curve over time is shown in FIG. 4A, and the body weight change was graphed in FIG. 4B.

TABLE 7

| Group | N | Treatment | Dosing (mg/kg) | Dosing Route | Dosing Schedule |
|---|---|---|---|---|---|
| 1 | 8 | Isotype Control vehicle | 10 — | i.p. p.o. | BIW (Day 0, 3/wk) × 2 weeks BID × 3 weeks |

TABLE 6

| Treatment | Tumor Volume[a] (mm³) on Day 0 | Tumor Volume (mm³) on Day 13 | % ΔInhibition[b] | P value[c] |
|---|---|---|---|---|
| Isotype Control | 202.01 ± 16.05 | 2127.17 ± 195.64 | — | — |
| JNJ-372 | 202.45 ± 19.68 | 39.97 ± 32.01 | 108.44% | 2.43 × 10⁻⁶ (***) |
| Capmatinib | 202.15 ± 18.52 | 13.92 ± 4.73 | 109.78% | 1.85 × 10⁻⁵ (***) |

[a]Data represent Mean tumor volume ± SEM.

[b]% ΔInhibition calculated as below:

$$\% \Delta \text{Inhibition} = \frac{(C13 - C0) - (T13 - T0)}{(C13 - C0)} \times 100$$

C (13 or 0): Mean tumor volume of Control group on indicated Study Day.

T (13 or 0): Mean tumor volume of Treatment group on indicated Study Day.

[c]P value were calculated by performing Conover's non-parametric many-to-one comparison test.

TABLE 7-continued

| Group | N | Treatment | Dosing (mg/kg) | Dosing Route | Dosing Schedule |
|---|---|---|---|---|---|
| 2 | 8 | JNJ-61186372 | 10 | i.p. | BIW (Day 0, 3/wk) × 3 weeks Then keep observation (till Day 123) |
| 3 | 8 | capmatinib | 10 | p.o. | BID × 3 weeks |
| 4 | 8 | JNJ-61186372 | 10 | i.p. | BIW (Day 0, 3/wk) × 3 weeks Then keep observation (till Day 123) |
|   |   | capmatinib | 10 | p.o. | BID × 3 weeks Then keep observation (till Day 123) | i.p.: intraperitoneal; p.o.: oral administration; BIW: bi-weekly; BID: twice a day

TABLE 8

| | Tumor Volume[a] (mm$^3$) | | | |
|---|---|---|---|---|
| Study Days | Isotype Control (10 mg/kg, BIW) 2 weeks | JNJ-61186372 (10 mg/kg, BIW) 3 weeks | Capmatinib (10 mg/kg, BID) 3 weeks | JNJ-61186372 + Capmatinib 3 weeks |
| 0 | 172.57 ± 17.38 | 172.47 ± 15.85 | 172.90 ± 17.67 | 172.89 ± 16.70 |
| 4 | 387.19 ± 66.70 | 24.13 ± 6.31 | 20.89 ± 4.14 | 15.14 ± 5.16 |
| 7 | 589.54 ± 113.57 | 8.38 ± 3.34 | 8.31 ± 3.29 | 3.78 ± 2.49 |
| 11 | 955.40 ± 162.67 | 2.87 ± 2.87 | 4.51 ± 2.26 | 0.00 ± 0.00 |
| 14 | 1431.11 ± 225.13 | 1.73 ± 1.73 | 4.65 ± 2.27 | 0.00 ± 0.00 |
| 18 | | 0.00 ± 0.00 | 3.79 ± 2.67 | 0.00 ± 0.00 |
| 21 | | 0.00 ± 0.00 | 0.00 ± 0.00 | 0.00 ± 0.00 |
| 25 | | 0.00 ± 0.00 | | 0.00 ± 0.00 |
| 28 | | 0.00 ± 0.00 | | 0.00 ± 0.00 |
| 32 | | 0.00 ± 0.00 | | 0.00 ± 0.00 |
| 35 | | 0.00 ± 0.00 | | 0.00 ± 0.00 |
| 39 | | 0.00 ± 0.00 | | 0.00 ± 0.00 |
| 42 | | 0.00 ± 0.00 | | 0.00 ± 0.00 |
| 46 | | 0.00 ± 0.00 | | 0.00 ± 0.00 |
| 49 | | 0.00 ± 0.00 | | 0.00 ± 0.00 |
| 53 | | 0.00 ± 0.00 | | 0.00 ± 0.00 |
| 56 | | 0.00 ± 0.00 | | 0.00 ± 0.00 |
| 60 | | 0.00 ± 0.00 | | 0.00 ± 0.00 |
| 63 | | 0.00 ± 0.00 | | 0.00 ± 0.00 |
| 67 | | 0.00 ± 0.00 | | 0.00 ± 0.00 |
| 70 | | 12.56 ± 12.56 | | 0.00 ± 0.00 |
| 74 | | 25.65 ± 25.65 | | 0.00 ± 0.00 |
| 77 | | 14.65 ± 14.65 | | 0.00 ± 0.00 |
| 81 | | 46.18 ± 46.18 | | 0.00 ± 0.00 |
| 84 | | 71.83 ± 54.81 | | 0.00 ± 0.00 |
| 88 | | 161.34 ± 127.73 | | 0.00 ± 0.00 |
| 91 | | 70.18 ± 70.18 | | 0.00 ± 0.00 |
| 95 | | 113.99 ± 113.99 | | 0.00 ± 0.00 |
| 98 | | 273.30 ± 273.30 | | 0.00 ± 0.00 |
| 102 | | 0.00 ± 0.00 | | 0.00 ± 0.00 |
| 105 | | 0.00 ± 0.00 | | 0.00 ± 0.00 |
| 109 | | 0.00 ± 0.00 | | 0.00 ± 0.00 |
| 112 | | 0.00 ± 0.00 | | 0.00 ± 0.00 |
| 116 | | 0.00 ± 0.00 | | 0.00 ± 0.00 |
| 119 | | 0.00 ± 0.00 | | 0.00 ± 0.00 |
| 123 | | 0.00 ± 0.00 | | 0.00 ± 0.00 |

[a]Data represent Mean tumor volume ± SEM; BIW: bi-weekly; BID: twice a day

The isotype and vehicle control group was terminated when the average tumor size reached 1400 mm3 on day 14. The tumor growth inhibition (TGI %) in each treatment group was calculated using the formula %ΔInhibition=100×((C−C0)−(T−T0))/(C−C0), and is shown in Table 9, T and C were the mean tumor volumes of the treated and control groups, respectively. Statistical analysis was performed using the same methods as in Example 3.

TABLE 9

| Treatment | Tumor Volume[a] (mm³) on Day 0 | Tumor Volume (mm³) on Day 14 | % ΔInhibition[b] | P value[c] |
|---|---|---|---|---|
| Isotype Control | 172.57 ± 17.38 | 1431.11 ± 225.13 | — | — |
| JNJ-61186372 | 172.47 ± 15.85 | 1.73 ± 1.73 | 113.57% | 4.44 × 10⁻⁸ (***) |
| Capmatinib | 172.90 ± 17.67 | 4.65 ± 2.27 | 113.37% | 1.21 × 10⁻⁶ (***) |
| JNJ-61186372 + Capmatinib | 172.89 ± 16.70 | 0.00 ± 0.00 | 113.74% | 5.94 × 10⁻⁹ (***) |

[a]Data represent Mean tumor volume ± SEM.
[b]% ΔInhibition calculated as below:

$$\% \; \Delta\text{Inhibition} = \frac{(C14 - C0) - (T14 - T0)}{(C14 - C0)} \times 100$$

C (14 or 0): Mean tumor volume of Control group on indicated Study Day.
T (14 or 0): Mean tumor volume of Treatment group on indicated Study Day.
[c]P value were calculated by performing Conover's non-parametric many-to-one comparison test.

While all three treatment groups induced rapid tumor regression, the combination of JNJ-372 and capmatinib produced longer and more durable response compared to mono-therapy in this study. 2 out of 8 animals in JNJ-372 group regrew around day 70 and all animals in the combo group remained tumor-free till study end (over 120 days).

Figure 5:
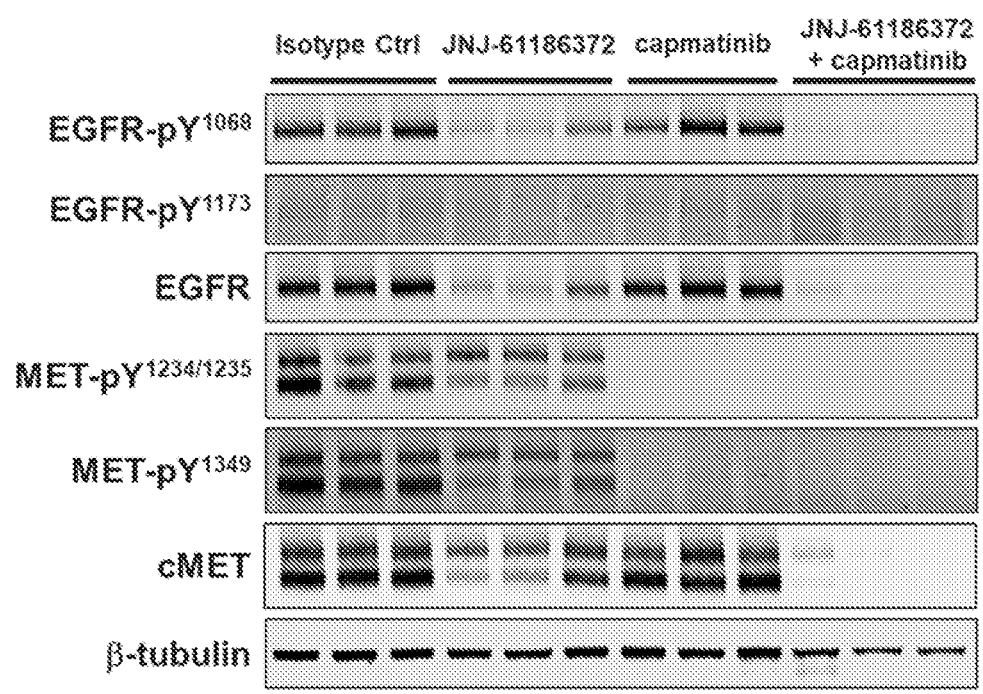
FIG. 5 shows protein levels determined by western blot, in LU2503 tumors grown in mice treated with JNJ-61186372 (JNJ-372), capmatinib, JNJ-61186372 and capmatinib, or Isotype control.
Figure 6A:
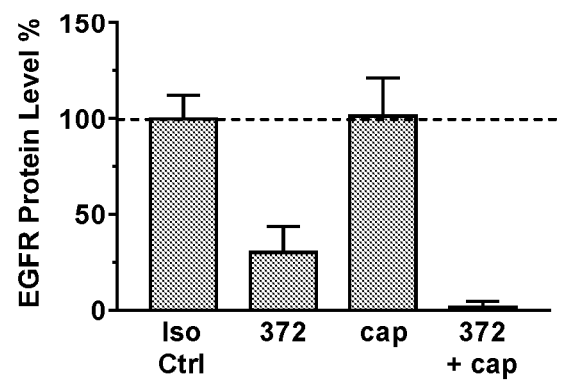
FIGS. 6A-6B show protein levels determined by western blot and quantified by using Image J software and normalized to β-tubulin, in LU2503 tumors grown in mice treated with JNJ-61186372 ("372"), capmatinib ("cap"), JNJ-61186372 and capmatinib ("372+cap"), or Isotype control ("Iso Ctrl").
Figure 6B:
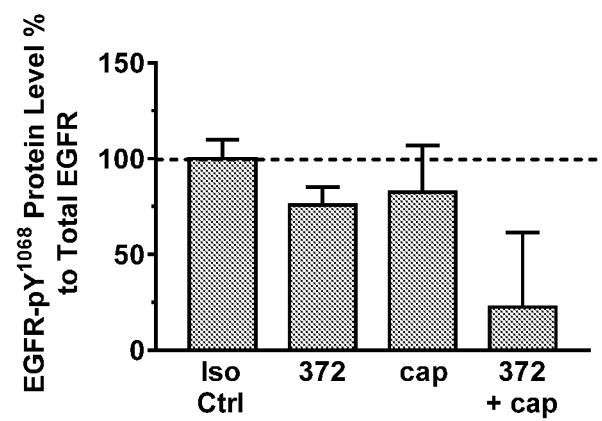
Figure 7A:
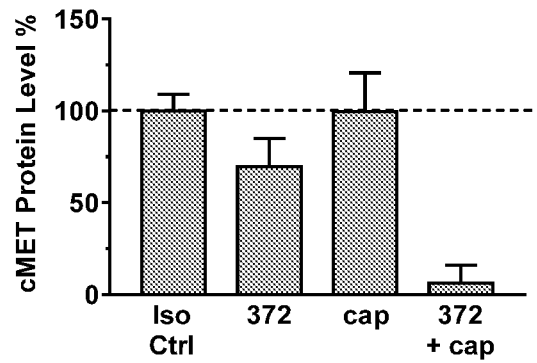
FIGS. 7A-7C show protein levels determined by western blot and quantified by using Image J software and normalized to β-tubulin, in LU2503 tumors grown in mice treated with JNJ-61186372 ("372"), capmatinib ("cap"), JNJ-61186372 and capmatinib ("372+cap"), or Isotype control ("Iso Ctrl").
Figure 7B:
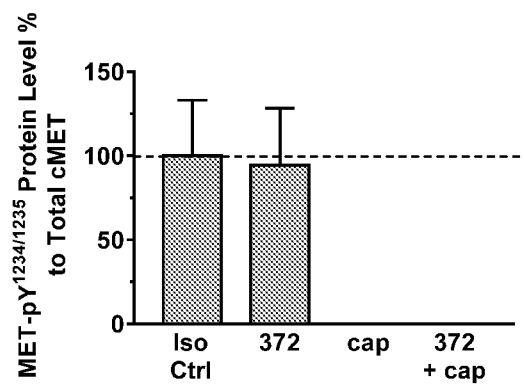
Figure 7C:
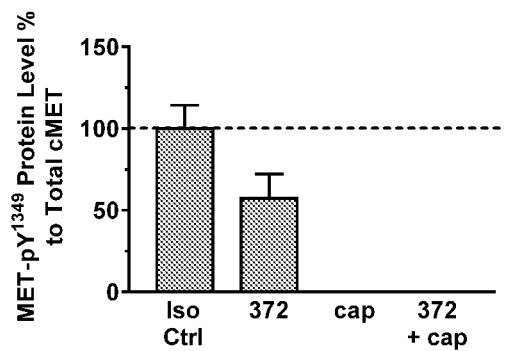

A concomitant study evaluating the pharmacodynamic parameters in LU2503 was conducted and the treatments were initiated when the tumors reached about 450-500 mm3. Samples were collected in all treatment groups at timepoints according to the design in Table 10. Snap-frozen tumors were homogenized in RIPA buffer containing protease and phosphatase inhibitor cocktails. 50 mg total protein (100 mg for phospho-EGFR) were loaded per lane for western blotting (see FIG. 5). Total MET (Cell Signaling, 8198S), EGFR (Cell Signaling, 4267S), phosphoMET-Tyr1234/1235 (Cell Signaling, 3077S), phosphoMET-Tyr1349 (Cell Signaling, 3133S), PhosphoEGFR-Tyr1068 (Cell Signaling, 3777S), and phospho EGFR-Tyr1173 (Cell Signaling, 4407S) protein levels were detected using the indicated primary antibodies, and the following secondary antibodies: IRDye800CW goat anti-rabbit (Li-Cor, 925-32211) and IRDye680RD goat anti-mouse (Li-Cor, 925-68070), using methods recommended by the manufactureres. The protein levels were quantified using Image J software and normalized to loading control β-tubulin in FIGS. 6A-6B and FIGS. 7A-7C.

TABLE 10

| Group | N | Treatment | Dosing (mg/kg) | Dosing Route | Dosing Schedule | Sampling Timepoint |
|---|---|---|---|---|---|---|
| 1 | 3 | Isotype Control vehicle | 10 — | i.p. p.o. | BIW (Day 0, 3) x 2 doses BID (Day 0-4) x 8 doses | 24-hr post 2nd dose 6-hr post last dose |
| 2 | 3 | JNJ-61186372 | 10 | i.p. | BIW (Day 0, 3) x 2 doses | 24-hr post 2nd dose |
| 3 | 3 | capmatinib | 10 | p.o. | BID x 1 dose | 6-hr post 1 dose |
| 4 | 3 | JNJ-61186372 capmatinib | 10 10 | i.p. p.o. | BIW (Day 0, 3) x 2 doses BID (Day 0-4) x 8 doses | 24-hr post 2nd dose 6-hr post last dose | i.p.: intraperitoneal; p.o.: oral administration; BIW: bi-weekly; BID: twice a day Consistent with the published mechanism of action, JNJ-372 caused total EGFR and MET receptor downmodulation. Unexpectedly, the JNJ-372/capmatinib combo group decreased both EGFR and MET receptor level further Similar synergistic effect in the phospho-EGFR and phospho-MET signaling inhibition was also observed in the combination group. In summary, the more robust PD marker inhibition in the combination treatment is consistent with the observed efficacy and warrant further investigation.

Example 5. JNJ-372 was Efficacious in the Inhibition of Tumor Growth in DFCI-440 MET Exon14 Skipping NSCLC PDX Model The efficacy of JNJ-372, the small molecule MET inhibitor capmatinib (Advanced ChemBlocks, Burlingame, Calif.), and their combination was compared in a NSCLC PDX model DFCI-440, a NSCLC patient explant (PDX) model harboring a MET exon14 skipping mutation developed at Dana Farber Cancer Institute (Boston, Mass.). Tumor fragments from stock tumor bearing mice were harvested and used for inoculation into female NSG™ mice. Each mouse was inoculated subcutaneously in the right rear flank with PDX DFCI-440 tumor fragments (approximately 2-3 mm in diameter) for tumor development.

After establishment of palpable lesions, the tumor growth was measured twice weekly. Once the tumor volume reached 150-250 mm3, animals were randomly allocated to relevant study groups with 8 mice each group. The day of randomization was denoted as day 0; treatments were started on day 0 and followed dosing schedule in Table 11.

TABLE 11

| Group | N | Treatment | Dosing Route | Dosing Schedule |
|---|---|---|---|---|
| 1 | 8 | Vehicle control (LFI control 10 mg/kg + vehicle (HPMC)) | i.p. (LFI) + p.o. (HPMC) | 2x per week for 3 weeks (LFI) + daily × 21 days (vehicle) |
| 2 | 8 | JNJ-61186372 (10 mg/kg) | i.p. | 2x per week for 3 weeks |
| 3 | 8 | Capmatinib (30 mg/kg) | p.o. | Daily × 21 days |
| 4 | 8 | JNJ-61186372 (10 mg/kg) + capmatinib (30 mg/kg) | i.p. (JNJ-372) + p.o. (capmatinib) | 2x per week for 3 weeks (JNJ-372) + daily × 21 days (capmatinib) |

LFI: low fucose isotype; HPMC: hydroxypropyl-methylcellulose; i.p.: intraperitoneal; p.o.: oral administration;

The study endpoints were to compare the tumor growth in each group at the end of treatments and the subsequent tumor outgrowth after dosing stopped. The tumor size was measured twice weekly in two dimensions using a caliper, and the volume was expressed in mm3 using the formula: V=(L×W×W)/2, where V was tumor volume, L was tumor length (the longest tumor dimension) and W was tumor width (the longest tumor dimension perpendicular to L). Tumor sizes (expressed as mean+SEM) for each group over time is shown in FIG. 8.

Figure 8:
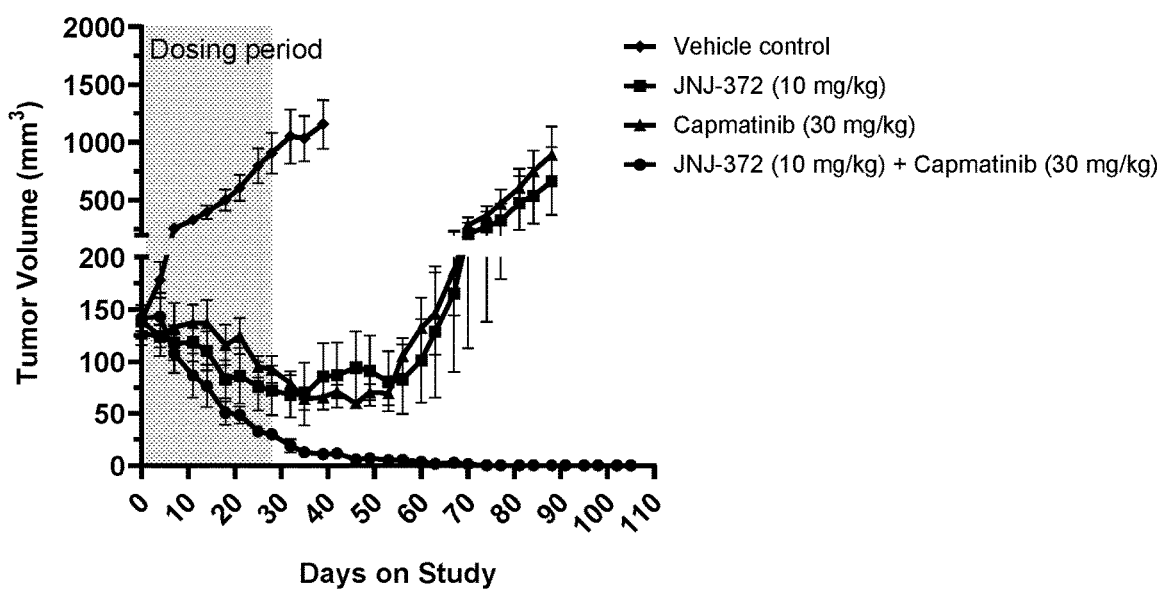
FIG. 8 shows mean tumor volumes in mice with tumors harboring c-Met exon 14 skipping mutation (DFCI-440), treated with JNJ-61186372 (JNJ-372), capmatinib, JNJ-61186372 and capmatinib, or Isotype control.

As shown in FIG. 8, both JNJ-372 and capmatinib as single agents significantly inhibited DFCI-440 tumor growth and caused these tumors to regress. After cessation of treatment, the tumors in mice treated with JNJ-372 or capmatinib as single agents resumed growth. However, Treatment with the combination of JNJ-372+capmatinib also effectively inhibited tumor growth and resulted in tumor regression, however, the combination treatment eliminated completely the tumors in 8 out of 8 mice, even after cessation of treatment.

We claim:

1. A method of treating a subject having a cancer that is positive for a c-Met exon 14 skipping mutation, the method comprising administering to the subject a combination therapy comprising:
   a therapeutically effective amount of an isolated bispecific anti-epidermal growth factor receptor (EGFR)/hepatocyte growth factor receptor (c-Met) antibody; and
   a therapeutically effective amount of a compound of formula (I)

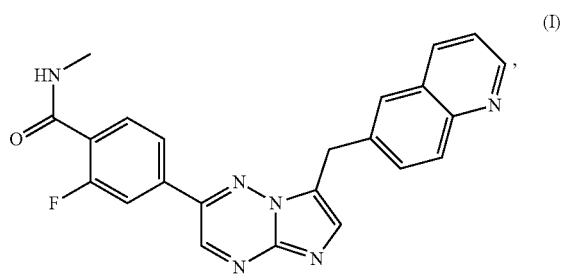 [SMILES: CNC(=O)c1ccc(-c2cnc3ncc(Cc4ccc5ncccc5c4)n3n2)cc1F]

or a pharmaceutically acceptable solvate, hydrate, tautomer, or salt thereof, wherein the bispecific anti-EGFR/c-Met antibody comprises:
   a first domain that binds EGFR, the first domain comprising a heavy chain complementarity determining region 1 (HCDR1) comprising the amino acid sequence of SEQ ID NO: 1, a HCDR2 comprising the amino acid sequence of SEQ ID NO: 2, a HCDR3 comprising the amino acid sequence of SEQ ID NO: 3, a light chain complementarity determining region 1 (LCDR1) comprising the amino acid sequence of SEQ ID NO: 4, a LCDR2 comprising the amino acid sequence of SEQ ID NO: 5, and a LCDR3 comprising the amino acid sequence of SEQ ID NO: 6; and
   a second domain that binds c-Met, the second domain comprising a HCDR1 comprising the amino acid sequence of SEQ ID NO: 7, a HCDR2 comprising the amino acid sequence of SEQ ID NO: 8, a HCDR3 comprising the amino acid sequence of SEQ ID NO: 9, a LCDR1 comprising the amino acid sequence of SEQ ID NO: 10, a LCDR2 comprising the amino acid sequence of SEQ ID NO: 11, and a LCDR3 comprising the amino acid sequence of SEQ ID NO: 12.

2. The method of claim 1, wherein the first domain that binds EGFR comprises a heavy chain variable region (VH) comprising the amino acid sequence of SEQ ID NO: 13 and a light chain variable region (VL) comprising the amino acid sequence of SEQ ID NO: 14, and the second domain that binds c-Met comprises a VH comprising the amino acid sequence of SEQ ID NO: 15 and a VL comprising the amino acid sequence of SEQ ID NO: 16.

3. The method of claim 1, wherein the bispecific anti-EGFR/c-Met antibody is an IgG1 isotype.

4. The method of claim 2, wherein the first domain that binds EGFR comprises a heavy chain (HC1) comprising the amino acid sequence of SEQ ID NO: 17 and a light chain (LC1) comprising the amino acid sequence of SEQ ID NO: 18, and the second domain that binds c-Met comprises a heavy chain (HC2) comprising the amino acid sequence of SEQ ID NO: 19 and a light chain (LC2) comprising the amino acid sequence of SEQ ID NO: 20.

5. The method of claim 1, wherein the bispecific anti-EGFR/c-Met antibody has a biantennary glycan structure with a fucose content of about 1% to about 15%.

6. The method of claim 1, wherein the compound of formula (I) or the solvate, hydrate, tautomer, or pharmaceutically acceptable salt thereof is 2-Fluoro-N-methyl-4-[7-(quinolin-6-ylmethyl) imidazo[1,2-b][1,2,4]triazin-2-yl]benzamide-hydrogen chloride-water (1/2/1).

7. The method of claim 1, wherein the subject is relapsed or resistant to treatment with one or more prior anti-cancer therapies.

8. The method of claim 7, wherein the one or more prior anti-cancer therapies comprise one or more chemotherapeutic agents, one or more checkpoint inhibitors, one or more targeted anti-cancer therapies, one or more kinase inhibitors, or any combination thereof.

9. The method of claim 7, wherein the one or more prior anti-cancer therapies comprise carboplatin, paclitaxel, gemcitabine, cisplatin, vinorelbine, docetaxel, palbociclib, crizotinib, a PD-(L) 1 axis inhibitor, an inhibitor of EGFR, an inhibitor of c-Met, an inhibitor of HER2, an inhibitor of HER3, an inhibitor of HER4, an inhibitor of VEGFR, an inhibitor of AXL, erlotinib, gefitinib, lapatinib, vandetanib, afatinib, osimertinib, lazertinib, poziotinib, criotinib, cabozantinib, axitinib, lenvatinib, nintedanib, regorafenib, pazopanib, sorafenib, sunitinib, or any combination thereof.

10. The method of claim 1, wherein the subject is treatment naïve.

11. The method of claim 1, wherein the cancer is positive for a CDK4 amplification, an EGFR amplification, a KRAS amplification, a MDM2 amplification, a TERT amplification, NF1 R2450*, RAD50 L597Vfs*5, MET c.3082+3A>G, EGFR, wild-type EGFR, an EGFR activating mutation, increased levels of circulating HGF, a c-MET amplification, a mutant KRAS, or any combination thereof.

12. The method of claim 11, wherein the EGFR activating mutation comprises a L718Q, G719A, G719X (X being any amino acid), L861X (X being any amino acid), L858R, E746K, L747S, E749Q, A750P, A755V, V765M, C797S, L858P, or T790M substitution, deletion of E746-A750, deletion of R748-P753, insertion of Ala (A) between M766 and A767, insertion of Ser, Val, and Ala (SVA) between S768 and V769, insertion of Asn and Ser (NS) between P772 and H773, insertion of one or more amino acids between D761 and E762, A763 and Y764, Y764 and Y765, M766 and A767, A767 and V768, S768 and V769, V769 and D770, D770 and N771, N771 and P772, P772 and H773, H773 and V774, V774 and C775, one or more deletions in EGFR exon 20, one or more insertions in EGFR exon 20, or any combination thereof.

13. The method of claim 11, wherein the mutant KRAS comprises a G12V, G12C, G12A, or G12D substitution, or any combination thereof.

14. The method of claim 1, wherein the cancer is lung cancer, gastric cancer, colorectal cancer, brain cancer, cancer derived from epithelial cells, breast cancer, ovarian cancer, anal cancer, prostate cancer, kidney cancer, bladder cancer, head and neck cancer, pharynx cancer, cancer of the nose, pancreatic cancer, skin cancer, oral cancer, cancer of the tongue, esophageal cancer, vaginal cancer, cervical cancer, cancer of the spleen, testicular cancer, cancer of the thymus, colon cancer, thyroid cancer, liver cancer, hepatocellular carcinoma (HCC), sporadic or hereditary papillary renal cell carcinoma (PRCC), or any combination thereof.

15. The method of claim 14, wherein the lung cancer is non-small cell lung cancer (NSCLC), small cell lung cancer (SCLC), lung adenocarcinoma, pulmonary sarcomatoid carcinoma, or any combination thereof.

16. The method of claim 1, comprising further administering one or more anti-cancer therapies to the subject.

17. The method of claim 16, wherein the one or more anti-cancer therapies comprise a chemotherapy, radiation therapy, surgery, targeted anti-cancer therapy, kinase inhibitor, or any combination thereof.

18. The method of claim 17, wherein the kinase inhibitor is an inhibitor of EGFR, an inhibitor of c-Met, an inhibitor of HER2, an inhibitor of HER3, an inhibitor of HER4, an inhibitor of VEGFR, or an inhibitor of AXL.

19. The method of claim 18, wherein the kinase inhibitor is erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib, or sunitinib.

20. The method of claim 1, wherein the c-Met exon 14 skipping mutation is a de novo mutation.

21. The method of claim 1, wherein the c-Met exon 14 skipping mutation is an acquired mutation.

22. The method of claim 1, wherein the bispecific anti-EGFR/c-Met antibody is administered at a dose of about 140 mg to about 1750 mg.

23. The method of claim 1, wherein the bispecific anti-EGFR/c-Met antibody is administered at a dose of about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, or about 1400 mg.

24. The method of claim 22, wherein the bispecific anti-EGFR/c-Met antibody is administered twice a week, once a week, once in two weeks, once in three weeks, or once in four weeks.

25. The method of claim 1, wherein the pharmaceutically acceptable salt of formula (I) is the compound of formula (II):

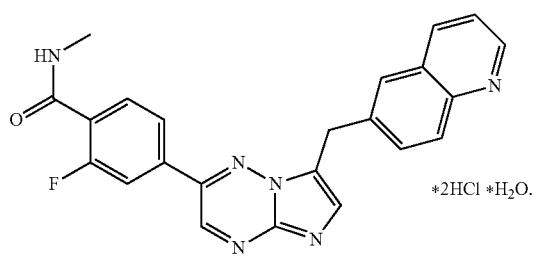 [SMILES: CNC(=O)c1ccc(-c2cnc3ncc(Cc4ccc5ncccc5c4)n3n2)cc1F]

26. A method of treating a subject having a cancer that is positive for a c-Met exon 14 skipping mutation, the method comprising administering to the subject a combination therapy comprising:

a therapeutically effective amount of an isolated bispecific anti-epidermal growth factor receptor (EGFR)/hepatocyte growth factor receptor (c-Met) antibody; and
and a therapeutically effective amount of the compound of formula (II)

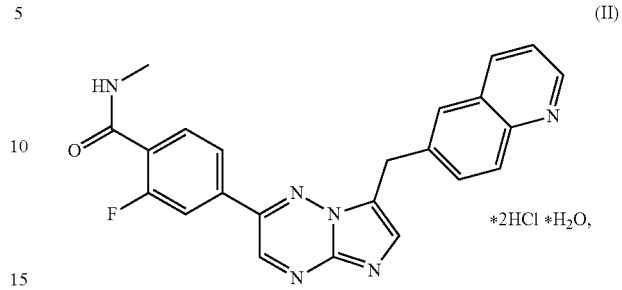

wherein the bispecific anti-EGFR/c-Met antibody comprises:
a first domain that binds EGFR, the first domain comprising a heavy chain complementarity determining region 1 (HCDR1) comprising the amino acid sequence of SEQ ID NO: 1, a HCDR2 comprising the amino acid sequence of SEQ ID NO: 2, a HCDR3 comprising the amino acid sequence of SEQ ID NO: 3, a light chain complementarity determining region 1 (LCDR1) comprising the amino acid sequence of SEQ ID NO: 4, a LCDR2 comprising the amino acid sequence of SEQ ID NO: 5, and a LCDR3 comprising the amino acid sequence of SEQ ID NO: 6; and
a second domain that binds c-Met, the second domain comprising a HCDR1 comprising the amino acid sequence of SEQ ID NO: 7, a HCDR2 comprising the amino acid sequence of SEQ ID NO: 8, a HCDR3 comprising the amino acid sequence of SEQ ID NO: 9, a LCDR1 comprising the amino acid sequence of SEQ ID NO: 10, a LCDR2 comprising the amino acid sequence of SEQ ID NO: 11, and a LCDR3 comprising the amino acid sequence of SEQ ID NO: 12.

27. The method of claim 26, wherein the first domain that binds EGFR comprises a heavy chain variable region (VH) comprising the amino acid sequence of SEQ ID NO: 13 and a light chain variable region (VL) comprising the amino acid sequence of SEQ ID NO: 14, and the second domain that binds c-Met comprises a VH comprising the amino acid sequence of SEQ ID NO: 15 and a VL comprising the amino acid sequence of SEQ ID NO: 16.

28. The method of claim 27, wherein the first domain that binds EGFR comprises a heavy chain (HC1) comprising the amino acid sequence of SEQ ID NO: 17 and a light chain (LC1) comprising the amino acid sequence of SEQ ID NO: 18, and the second domain that binds c-Met comprises a heavy chain (HC2) comprising the amino acid sequence of SEQ ID NO: 19 and a light chain (LC2) comprising the amino acid sequence of SEQ ID NO: 20.

29. The method of claim 26, wherein the bispecific anti-EGFR/c-Met antibody is an IgG1 isotype.

30. The method of claim 26, wherein the subject is relapsed or resistant to treatment with one or more prior anti-cancer therapies.

31. The method of claim 30, wherein the one or more prior anti-cancer therapies comprise one or more chemotherapeutic agents, one or more checkpoint inhibitors, one or more targeted anti-cancer therapies, one or more kinase inhibitors, or any combination thereof.

32. The method of claim 30, wherein the one or more prior anti-cancer therapies comprise carboplatin, paclitaxel, gemcitabine, cisplatin, vinorelbine, docetaxel, palbociclib, crizotinib, a PD-(L)1 axis inhibitor, an inhibitor of EGFR, an inhibitor of c-Met, an inhibitor of HER2, an inhibitor of HER3, an inhibitor of HER4, an inhibitor of VEGFR, an inhibitor of AXL, erlotinib, gefitinib, lapatinib, vandetanib, afatinib, osimertinib, lazertinib, poziotinib, criotinib, cabozantinib, axitinib, lenvatinib, nintedanib, regorafenib, pazopanib, sorafenib, sunitinib, or any combination thereof.

33. The method of claim 26, wherein the subject is treatment naïve.

34. The method of claim 26, wherein the cancer is positive for a CDK4 amplification, an EGFR amplification, a KRAS amplification, a MDM2 amplification, a TERT amplification, NF1 R2450*, RAD50 L597Vfs*5, MET c.3082+3A>G, EGFR, wild-type EGFR, an EGFR activating mutation, increased levels of circulating HGF, a c-MET amplification, a mutant KRAS, or any combination thereof.

35. The method of claim 34, wherein the EGFR activating mutation comprises a L718Q, G719A, G719X (X being any amino acid), L861X (X being any amino acid), L858R, E746K, L747S, E749Q, A750P, A755V, V765M, C797S, L858P, or T790M substitution, deletion of E746-A750, deletion of R748-P753, insertion of Ala (A) between M766 and A767, insertion of Ser, Val, and Ala (SVA) between S768 and V769, insertion of Asn and Ser (NS) between P772 and H773, insertion of one or more amino acids between D761 and E762, A763 and Y764, Y764 and Y765, M766 and A767, A767 and V768, S768 and V769, V769 and D770, D770 and N771, N771 and P772, P772 and H773, H773 and V774, V774 and C775, one or more deletions in EGFR exon 20, one or more insertions in EGFR exon 20, or any combination thereof.

36. The method of claim 34, wherein the mutant KRAS comprises a G12V, G12C, G12A, or G12D substitution, or any combination thereof.

37. The method of claim 26, wherein the cancer is lung cancer, gastric cancer, colorectal cancer, brain cancer, cancer derived from epithelial cells, breast cancer, ovarian cancer, anal cancer, prostate cancer, kidney cancer, bladder cancer, head and neck cancer, pharynx cancer, cancer of the nose, pancreatic cancer, skin cancer, oral cancer, cancer of the tongue, esophageal cancer, vaginal cancer, cervical cancer, cancer of the spleen, testicular cancer, cancer of the thymus, colon cancer, thyroid cancer, liver cancer, hepatocellular carcinoma (HCC), sporadic or hereditary papillary renal cell carcinoma (PRCC), or any combination thereof.

38. The method of claim 37, wherein the lung cancer is non-small cell lung cancer (NSCLC), small cell lung cancer (SCLC), lung adenocarcinoma, pulmonary sarcomatoid carcinoma, or any combination thereof.

39. The method of claim 26, comprising further administering one or more anti-cancer therapies to the subject.

40. The method of claim 39, wherein the one or more anti-cancer therapies comprise a chemotherapy, radiation therapy, surgery, targeted anti-cancer therapy, kinase inhibitor, or any combination thereof.

41. The method of claim 40, wherein the kinase inhibitor is an inhibitor of EGFR, an inhibitor of c-Met, an inhibitor of HER2, an inhibitor of HER3, an inhibitor of HER4, an inhibitor of VEGFR, or an inhibitor of AXL.

42. The method of claim 41, wherein the kinase inhibitor is erlotinib, gefitinib, lapatinib, vandetanib, afatinib, osimertinib, lazertinib, poziotinib, criotinib, cabozantinib, capmatinib, axitinib, lenvatinib, nintedanib, regorafenib, pazopanib, sorafenib, or sunitinib.

43. The method of claim 26, wherein the c-Met exon 14 skipping mutation is a de novo mutation.

44. The method of claim 26, wherein the c-Met exon 14 skipping mutation is an acquired mutation.

45. The method of claim 26, wherein the bispecific anti-EGFR/c-Met antibody is administered at a dose of about 140 mg to about 1750 mg.

46. The method of claim 45, wherein the bispecific anti-EGFR/c-Met antibody is administered at a dose of about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, or about 1400 mg.

47. The method of claim 45, wherein the bispecific anti-EGFR/c-Met antibody is administered twice a week, once a week, once in two weeks, once in three weeks, or once in four weeks.

* * * * *

UNITED STATES PATENT AND TRADEMARK OFFICE
CERTIFICATE OF CORRECTION

PATENT NO. : 12,215,160 B2
APPLICATION NO. : 17/174386
DATED : February 4, 2025
INVENTOR(S) : Roland Knoblauch et al.

It is certified that error appears in the above-identified patent and that said Letters Patent is hereby corrected as shown below:

On the Title Page

In Other Publications,

Column 1, Page 2, Line 33, Replace:
"TK1"
With:
--TKI--

Column 2, Page 2, Line 4, Replace:
"TK1"
With:
--TKI--

Column 2, Page 3, Line 46, Replace:
"retreived"
With:
--retrieved--

Column 2, Page 3, Line 59, Replace:
"IgGI"
With:
--IgG1--

In the Claims

Column 78, Claim 9, Line 21, Replace:
"PD-(L) 1"
With:
--PD-(L)1--

Signed and Sealed this
Ninth Day of December, 2025

John A. Squires
*Director of the United States Patent and Trademark Office*

CERTIFICATE OF CORRECTION (continued)
U.S. Pat. No. 12,215,160 B2

Column 78, Claim 9, Line 25, Replace:
"criotinib,"
With:
--crizotinib,--

Column 79, Claim 19, Line 18, Replace:
"criotinib,"
With:
--crizotinib,--

Column 80, Claim 26, Line 1, Replace:
"and a"
With:
--a--

Column 81, Claim 32, Line 6, Replace:
"criotinib,"
With:
--crizotinib,--

Column 82, Claim 42, Line 21, Replace:
"criotinib,"
With:
--crizotinib,--